US010071984B2

(12) United States Patent
Chen et al.

(10) Patent No.: US 10,071,984 B2
(45) Date of Patent: Sep. 11, 2018

(54) HISTONE DEMETHYLASE INHIBITORS

(71) Applicant: Celgene Quanticel Research, Inc., San Diego, CA (US)

(72) Inventors: Young K. Chen, San Marcos, CA (US); Zhe Nie, San Diego, CA (US); Jeffrey Alan Stafford, San Diego, CA (US); James Marvin Veal, Apex, NC (US)

(73) Assignee: Celgene Quanticel Research, Inc., San Diego, CA (US)

( * ) Notice: Subject to any disclaimer, the term of this patent is extended or adjusted under 35 U.S.C. 154(b) by 0 days.

(21) Appl. No.: 15/588,495

(22) Filed: May 5, 2017

(65) Prior Publication Data

US 2017/0240529 A1    Aug. 24, 2017

Related U.S. Application Data

(62) Division of application No. 14/855,269, filed on Sep. 15, 2015, now Pat. No. 9,676,770.

(60) Provisional application No. 62/051,268, filed on Sep. 16, 2014.

(51) Int. Cl.
   *C07D 401/14* (2006.01)
   *C07D 405/14* (2006.01)

(52) U.S. Cl.
   CPC ......... *C07D 401/14* (2013.01); *C07D 405/14* (2013.01)

(58) Field of Classification Search
   CPC .................................................. C07D 401/14
   See application file for complete search history.

(56) References Cited

U.S. PATENT DOCUMENTS

| 6,846,834 | B2 | 1/2005 | Browner et al. |
| 7,186,841 | B2 | 3/2007 | Browner et al. |
| 7,977,334 | B2 | 7/2011 | Trieselmann et al. |
| 9,107,916 | B2 | 8/2015 | Nie et al. |
| 9,133,166 | B2 | 9/2015 | Kanouni et al. |
| 9,676,770 | B2 * | 6/2017 | Chen .................... C07D 401/14 |
| 9,896,436 | B2 * | 2/2018 | Chen .................... C07D 471/04 |
| 2004/0127733 | A1 | 7/2004 | Trieselmann et al. |
| 2005/0245526 | A1 | 11/2005 | Trieselmann et al. |
| 2006/0074244 | A1 | 4/2006 | Gellibert |
| 2007/0135464 | A1 | 6/2007 | Browner et al. |
| 2009/0221589 | A1 | 9/2009 | Trieselmann et al. |
| 2011/0111046 | A1 | 5/2011 | Bagley et al. |
| 2012/0053178 | A1 | 3/2012 | Dorsch et al. |
| 2014/0194469 | A1 | 7/2014 | Nie et al. |
| 2014/0275084 | A1 | 9/2014 | Kanouni et al. |
| 2015/0038534 | A1 | 2/2015 | Baloglu et al. |
| 2016/0009711 | A1 | 1/2016 | Wu et al. |
| 2016/0108033 | A1 | 4/2016 | Chen et al. |

FOREIGN PATENT DOCUMENTS

WO   2000/039108 A1   7/2000
WO   2009/045992 A2   4/2009
WO   2014/151945 A1   9/2014

OTHER PUBLICATIONS

England et al., "Optimisation of a triazolopyridine-based histone demethylase inhibitor yields a potent and selective KDM2A (FBXL11) inhibitor," Medicinal Chemistry Communication., (Sep. 15, 2014), vol. 5, pp. 1879-1886, XP055419167 [S] 1-15, entire document, especially: p. 1881, Table 2, Structure 14a.
Extended European Search Report dated Jan. 24, 2018, in related European Patent Application No. 15842092.7, filed Sep. 15, 2015.
Search Report and Written Opinion dated Nov. 22, 2017, in related Singapore Patent Application No. 11201702108P, filed Sep. 15, 2015.
Berge et al., "Pharmaceutical Salts." Journal of Pharmaceutical Sciences 66(1):1-19 (Jan. 1977).
Bundgard et al., Design of Prodrugs, pp. 7-9, 21-24 (1985).
Co-pending U.S. Appl. No. 14/852,079, filed Sep. 11, 2015.
Klose et al., "JmjC-domain-containing proteins and histone demethylation." Nature Reviews Genetics 7:715-727 (Sep. 2006).
Lachner et al., "An epigenetic road map for histone lysine methylation." Journal of Cell Science 116:2117-2124 (Jun. 1, 2003).
Lin et al., Loss of the retinoblastoma binding protein 2 (RBP2) histone demethylase suppresses tumorgenesis in mice lacking RB1 or Men1.PNAS108(33):13379-13386 (2011).
Mangueron et al., "The key to development: interpreting the histone code?" Current Opinion Genet. Dev. 15:163-176 (2005).
International Preliminary Report on Patentability, dated Sep. 24, 2015, issued in International Patent Application No. PCT/US2014/26710, filed Mar. 13, 2014.
International Search Report and Written Opinion, dated Jul. 14, 2014, issued in International Patent Application No. PCT/US2014/26710, filed Mar. 13, 2014.
Pubchem SureCN11168572, CID 70529681, pp. 1-3, Create DAte: Dec. 1, 2012; p. 1; [retrieved on Jun. 4, 2014]. Retrieved from the Internet: < URL: http://pubchem.ncbi.nlm.nih.gov/summary/summary.cgi?cid=70529681&loc=ec_rcs>.
Pubchem SureCN12075252, CID 13320858, pp. 1-5, Create Date: Feb. 8, 2007; page 1;[retrieved on Jun. 4, 2014]. Retrieved from the Internet: <URL: http://pubchem.ncbi.nlm.nih.gov/summary/summary.cgi?cid=13320858&loc=ec_rcs>.
Pubchem SureCN12427208, CID 60046595, pp. 1-5, Create Date: Aug. 20, 2012; p. 1; [retrieved on Jun. 4, 2014]. Retrieved from the Internet: < URL: http://pubchem.ncbi.nlm.nih.gov/summary/summary.cgi?cid=60046595&loc=ec_rcs>.
Pubchem SureCN14499331, CID 20753075, pp. 1-6, Create Date: Dec. 5, 2007; p. 1; [retrieved on Jun. 4, 2014]. Retrieved from the Internet: <URL: http://pubchem.ncbi.nlm.nih.gov/summary/summary.cgi?cid-20753075&loc=ec_rcs>.
Pubchem SureCN1899117, CID 57525825, pp. 1-6, Create Date: Aug. 16, 2012; p. 1; [retrieved on Jun. 4, 2014]. Retrieved from the Internet: <URL: http://pubchem.ncbi.nlm.nih.gov/summary/summary.cgi?cid=57525825&loc=ec_rcs>.

(Continued)

*Primary Examiner* — Nizal S Chandrakumar
(74) *Attorney, Agent, or Firm* — Wiley Rein LLP

(57) ABSTRACT

The present invention relates generally to compositions and methods for treating cancer and neoplastic diseases. Provided herein are substituted imidazole-pyridine derivative compounds and pharmaceutical compositions comprising said compounds. The subject compounds and compositions are useful for inhibition of histone demethylase enzymes. Furthermore, the subject compounds and compositions are useful for the treatment of cancer, such as pancreatic cancer, prostate cancer, breast cancer, bladder cancer, lung cancer, gastric cancer, leukemia and/or melanoma and the like.

28 Claims, No Drawings

(56) References Cited

OTHER PUBLICATIONS

Pubchem SureCN6808551, CID 9859560, pp. 1-3, Create Date: Oct. 25, 2006; p. 1; [retrieved on Jun. 4, 2014]. Retrieved from the Internet: <URL: http://pubchem.ncbi.nlm.nih.govisummary/summary.cgi?cid=9855608Jocrec_rcs>.
Stahl et al., Handbook of Pharmaceutical Salts. Verlag Helvetica Chimica Acta, Zurich, 2002.
Office Action, dated Feb. 5, 2015, issued in U.S. Appl. No. 14/210,006, filed Mar. 13, 2014, issued as U.S. Patent No. 9,133,166, dated Sep. 15, 2015.
International Search Report and Written Opinion dated Dec. 17, 2015, in related International Patent Application No. PCT/US2015/050289, filed Sep. 15, 2015.
International Preliminary Report on Patentability dated Mar. 30, 2017, in related International Patent Application No. PCT/US2015/050289, filed Sep. 15, 2015.
International Search Report and Written Opinion dated Jun. 7, 2017, in related International Application No. PCT/US2017/022570, filed Mar. 15, 2017.

\* cited by examiner

HISTONE DEMETHYLASE INHIBITORS

CROSS-REFERENCE

This application is a division of U.S. patent application Ser. No. 14/855,269, filed Sep. 15, 2015 (now U.S. Pat. No. 9,676,770), which claims the benefit of U.S. Provisional Application 62/051,268, filed Sep. 16, 2014, which is incorporated herein by reference in its entirety.

BACKGROUND

A need exists in the art for an effective treatment of cancer and neoplastic diseases.

BRIEF SUMMARY OF THE INVENTION

Provided herein are substituted imidazole-pyridine derivative compounds and pharmaceutical compositions comprising said compounds. The subject compounds and compositions are useful for the inhibition of histone demethylases. Furthermore, the subject compounds and compositions are useful for the treatment of cancer, such as pancreatic cancer, prostate cancer, breast cancer, bladder cancer, lung cancer, gastric cancer, leukemia and/or melanoma and the like. The substituted imidazole-pyridine derivative compounds described herein are based upon a substituted 2-(1H-imidazol-4-yl)pyridine ring system bearing a fused or linked triazole ring system.

One embodiment provides a compound having the structure of Formula (I),

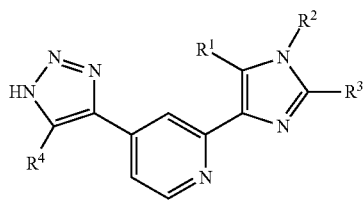

(I)

or a pharmaceutically acceptable salt thereof, wherein
$R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
$R^2$ is alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —NH$_2$, —NH(C$_1$-C$_3$alkyl) or C$_1$-C$_3$alkyl;
$R^4$ is hydrogen, C$_1$-C$_4$alkyl, C$_1$-C$_4$alkene, C$_1$-C$_4$alkyne, halogen, or —CN; and
each $R^5$ is independently hydrogen, alkyl, carbocyclyl, heterocyclyl, aryl, heteroaryl, carbocyclylalkyl, heterocyclylalkyl, aralkyl, or heteroarylalkyl.

One embodiment provides a compound having the structure of Formula (II),

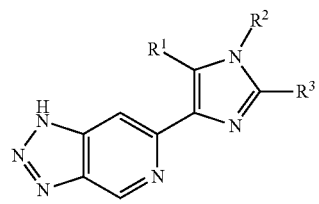

(II)

or a pharmaceutically acceptable salt thereof, wherein
$R^1$ is hydrogen, halogen, —OH, —OR$^4$, —N(R$^4$)$_2$, alkyl, carbocyclyl, heterocyclyl, aryl, heteroaryl, carbocyclylalkyl, heterocyclylalkyl, aralkyl, or heteroarylalkyl;
$R^2$ is alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —NH$_2$, —NH(C1-C3alkyl) or C1-C3alkyl; and
each $R^4$ is independently hydrogen, alkyl, carbocyclyl, heterocyclyl, aryl, heteroaryl, carbocyclylalkyl, heterocyclylalkyl, aralkyl, or heteroarylalkyl.

One embodiment provides a pharmaceutical composition comprising a compound of Formula (I), or a pharmaceutically acceptable salt thereof, and a pharmaceutically acceptable excipient. One embodiment provides a pharmaceutical composition comprising a compound of Formula (II), or a pharmaceutically acceptable salt thereof, and a pharmaceutically acceptable excipient.

One embodiment provides a method for inhibiting a histone demethylase enzyme comprising contacting the histone demethylase enzyme with a compound of Formula (I). One embodiment provides a method for inhibiting a histone demethylase enzyme comprising contacting the histone demethylase enzyme with a compound of Formula (II).

One embodiment provides a method of treating cancer in a patient in need thereof, comprising administering to the patient a compound of Formula (I), or a pharmaceutically acceptable salt thereof. One embodiment provides a method of treating cancer in a patient in need thereof, comprising administering to the patient a compound of Formula (II), or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

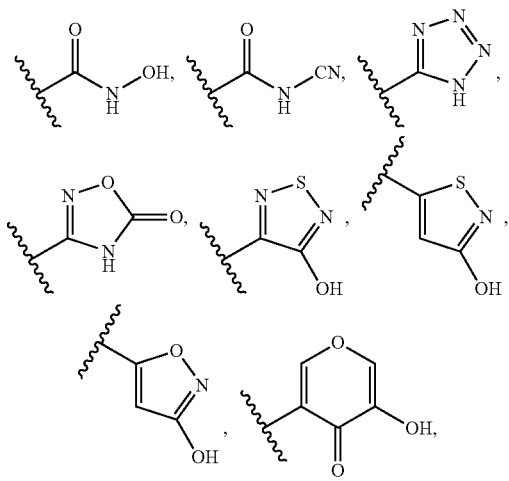

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para- isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

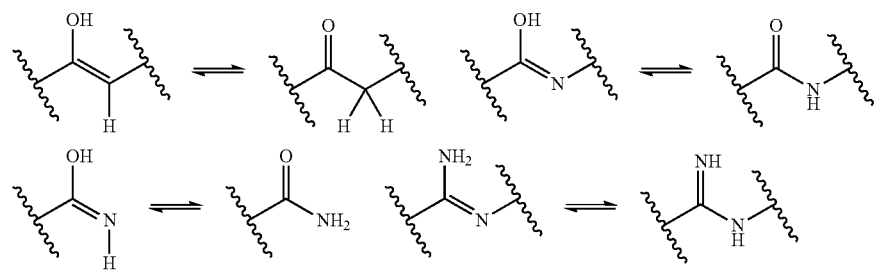

-continued

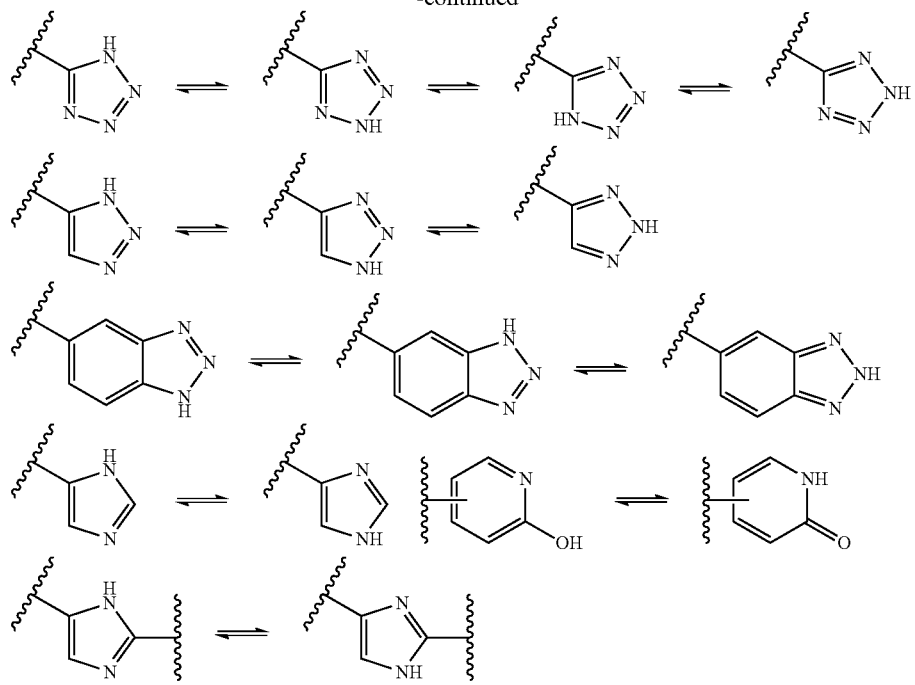

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted imidazole-pyridine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Imidazole-Pyridine Derivative Compounds

Substituted imidazole-pyridine derivative compounds are described herein that inhibit a histone demethylase enzyme. These compounds, and compositions comprising these compounds, are useful for the treatment of cancer and neoplastic diseases. The compounds described herein may, therefore, be useful for treating pancreatic cancer, prostate cancer, breast cancer, bladder cancer, lung cancer, gastric cancer, leukemia and/or melanoma and the like.

One embodiment provides a compound having the structure of Formula (I),

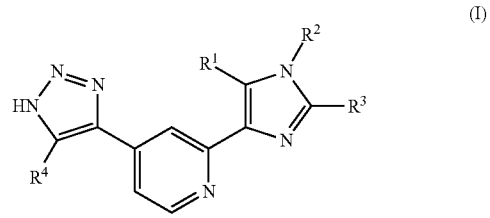

or a pharmaceutically acceptable salt thereof, wherein
$R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
$R^2$ is alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —NH$_2$, —NH(C1-C3alkyl) or C1-C3alkyl;
$R^4$ is hydrogen, $C_1$-$C_4$alkyl, $C_1$-$C_4$alkene, $C_1$-$C_4$alkyne, halogen, or —CN; and
each $R^5$ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides a compound of Formula (I), or a pharmaceutically acceptable salt thereof, wherein $R^3$ is hydrogen.

Another embodiment provides a compound of Formula (I), or a pharmaceutically acceptable salt thereof, wherein $R^2$ is alkyl. Another embodiment provides a compound of Formula (I), or a pharmaceutically acceptable salt thereof, wherein $R^2$ is methyl.

Another embodiment provides a compound of Formula (I), or a pharmaceutically acceptable salt thereof, wherein $R^2$ is carbocyclyl or carbocyclylalkyl. Another embodiment provides a compound of Formula (I), or a pharmaceutically acceptable salt thereof, wherein $R^2$ is —($C_1$-$C_6$alkylene)carbocyclyl. Another embodiment provides a compound of Formula (I), or a pharmaceutically acceptable salt thereof, wherein $R^2$ is —($C_1$-$C_6$alkylene)carbocyclyl and the ($C_1$-$C_6$alkylene) is a $C_1$alkylene, or a $C_2$alkylene.

Another embodiment provides a compound of Formula (I), or a pharmaceutically acceptable salt thereof, wherein $R^2$ is —($C_1$-$C_6$alkylene)carbocyclyl and the carbocyclyl is 1,2,3,4-tetrahydronaphthyl optionally substituted with one or more groups selected from halogen, hydroxy, —CN, alkyl, alkoxy, alkylamino, aryl, carbocyclyl, heterocyclyl, carbocyclylalkyl, and heterocyclylalkyl.

Another embodiment provides a compound of Formula (I), or a pharmaceutically acceptable salt thereof, wherein $R^2$ is heterocyclyl or heterocyclylalkyl.

Another embodiment provides a compound of Formula (I), or a pharmaceutically acceptable salt thereof, wherein $R^2$ is heteroaryl or heteroarylalkyl.

Another embodiment provides a compound of Formula (I), or a pharmaceutically acceptable salt thereof, wherein $R^2$ is aryl or aralkyl. Another embodiment provides a compound of Formula (I), or a pharmaceutically acceptable salt thereof, wherein $R^2$ is aralkyl, and the aralkyl is —($C_1$-$C_6$alkylene)aryl. Another embodiment provides a compound of Formula (I), or a pharmaceutically acceptable salt thereof, wherein $R^2$ is aralkyl, the aralkyl is —($C_1$-$C_6$alkylene)aryl and the ($C_1$-$C_6$alkylene) is $C_1$alkylene, or a $C_2$alkylene.

Another embodiment provides a compound of Formula (I), or a pharmaceutically acceptable salt thereof, wherein $R^2$ is aryl or aralkyl, and the aryl is a phenyl optionally substituted with one or more groups selected from halogen, hydroxy, —CN, alkyl, alkoxy, alkylamino, aryl, carbocyclyl, heterocyclyl, carbocyclylalkyl, and heterocyclylalkyl.

Another embodiment provides a compound of Formula (I), or a pharmaceutically acceptable salt thereof, wherein $R^2$ is aryl or aralkyl, and the aryl is naphthyl optionally substituted with one or more groups selected from halogen, hydroxy, —CN, alkyl, alkoxy, alkylamino, aryl, carbocyclyl, heterocyclyl, carbocyclylalkyl, and heterocyclylalkyl.

Another embodiment provides a compound of Formula (I), or a pharmaceutically acceptable salt thereof, wherein $R^4$ is hydrogen, halogen, —CN, or an alkyl optionally substituted with at least one fluoro. Another embodiment provides a compound of Formula (I), or a pharmaceutically acceptable salt thereof, wherein $R^4$ is hydrogen. Another embodiment provides a compound of Formula (I), or a pharmaceutically acceptable salt thereof, wherein $R^4$ is fluoro. Another embodiment provides a compound of Formula (I), or a pharmaceutically acceptable salt thereof, wherein $R^4$ is chloro. Another embodiment provides a compound of Formula (I), or a pharmaceutically acceptable salt thereof, wherein $R^4$ is iodo. Another embodiment provides a compound of Formula (I), or a pharmaceutically acceptable salt thereof, wherein $R^4$ is —CN. Another embodiment provides a compound of Formula (I), or a pharmaceutically acceptable salt thereof, wherein $R^4$ is —CF$_3$.

Another embodiment provides a compound of Formula (I), or a pharmaceutically acceptable salt thereof, wherein $R^1$ is hydrogen or aryl. Another embodiment provides a compound of Formula (I), or a pharmaceutically acceptable salt thereof, wherein $R^1$ is hydrogen. Another embodiment provides a compound of Formula (I), or a pharmaceutically acceptable salt thereof, wherein $R^1$ is aryl. Another embodiment provides a compound of Formula (I), or a pharmaceutically acceptable salt thereof, wherein $R^1$ is aryl and the aryl is a phenyl optionally substituted with one or more groups selected from halogen, hydroxy, —CN, alkyl, alkoxy, —O-(cycloalkylalkyl), alkylamino, aryl, carbocyclyl, heterocyclyl, carbocyclylalkyl, and heterocyclylalkyl. Another embodiment provides a compound of Formula (I), or a pharmaceutically acceptable salt thereof, wherein $R^1$ is aryl, and the aryl is a phenyl is substituted with one or more groups selected from halogen, alkoxy, or —O-(cycloalkylalkyl).

One embodiment provides a compound having the structure of Formula (Ia),

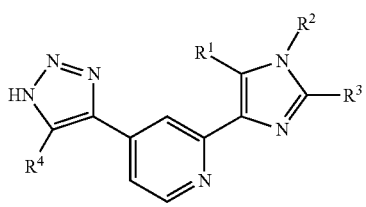

(Ia)

or a pharmaceutically acceptable salt thereof, wherein
$R^1$ is aryl, or heteroaryl; wherein $R^1$ is optionally substituted with halogen, —OH, —CN, alkyl, carbocyclyl, heterocyclyl, aryl, heteroaryl, carbocyclylalkyl, heterocyclylalkyl, aralkyl, heteroarylalkyl, alkyl-O—, carbocyclyl-O—, heterocyclyl-O—, aryl-O—, heteroaryl-O—, carbocyclylalkyl-O—, heterocyclylalkyl-O—, aralkyl-O—, or heteroarylalkyl-O—;

$R^2$ is methyl;
$R^3$ is hydrogen; and
$R^4$ is hydrogen, C$_1$-C$_4$alkyl, C$_1$-C$_4$alkene, C$_1$-C$_4$alkyne, halogen, or —CN.

Another embodiment provides the compound of Formula (Ia), or a pharmaceutically acceptable salt thereof, wherein $R^4$ is C$_1$-C$_4$alkyl. Another embodiment provides the compound of Formula (Ia), or a pharmaceutically acceptable salt thereof, wherein $R^4$ is C$_1$-C$_4$alkyl, and the alkyl is substituted with at least one fluoro. Another embodiment provides the compound of Formula (Ia), or a pharmaceutically acceptable salt thereof, wherein $R^4$ is CH$_2$F, CHF$_2$, or CF$_3$. Another embodiment provides the compound of Formula (Ia), or a pharmaceutically acceptable salt thereof, wherein $R^4$ is CF$_3$.

Another embodiment provides the compound of Formula (Ia), or a pharmaceutically acceptable salt thereof, wherein $R^1$ is aryl. Another embodiment provides the compound of Formula (Ia), or a pharmaceutically acceptable salt thereof, wherein $R^1$ is heteroaryl. Another embodiment provides the compound of Formula (Ia), or a pharmaceutically acceptable salt thereof, wherein $R^1$ is aryl, and the aryl is optionally substituted with halogen, alkyl-O—, carbocyclyl-O—, heterocyclyl-O—, aryl-O—, heteroaryl-O—, carbocyclylalkyl-O—, heterocyclylalkyl-O—, aralkyl-O—, or heteroarylalkyl-O—. Another embodiment provides the compound of Formula (Ia), or a pharmaceutically acceptable salt thereof, wherein $R^1$ is aryl, and the aryl is optionally substituted with halogen, alkyl-O—, carbocyclyl-O—, heterocyclyl-O—, aryl-O—, heteroaryl-O—, carbocyclylalkyl-O—, heterocyclylalkyl-O—, aralkyl-O—, or heteroarylalkyl-O—.

One embodiment provides a compound having the structure of Formula (Ib),

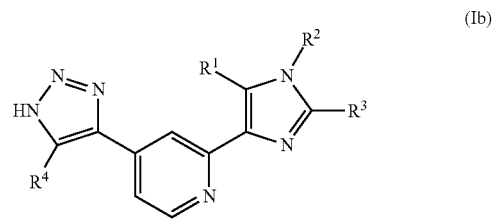

(Ib)

or a pharmaceutically acceptable salt thereof, wherein
$R^1$ is hydrogen;
$R^2$ is chosen from —(C$_1$-C$_6$alkylene)-(1,2,3,4-tetrahydronaphthyl), —(C$_1$-C$_6$alkylene)-(indanyl), —(C$_1$-C$_6$alkylene)-(chromanyl), —(C$_1$-C$_6$alkylene)-(dihydrobenzofuranyl)
$R^3$ is hydrogen; and
$R^4$ is hydrogen, C$_1$-C$_4$alkyl, C$_1$-C$_4$alkene, C$_1$-C$_4$alkyne, halogen, or —CN.

Another embodiment provides the compound of Formula (Ib), or a pharmaceutically acceptable salt thereof, wherein $R^2$ is chosen from —(C$_1$-C$_6$alkylene)-(1,2,3,4-tetrahydronaphthyl), optionally substituted with one or more groups selected from halogen, hydroxy, —CN, alkyl, alkoxy, alkylamino, aryl, carbocyclyl, carbocyclyloxy, heterocyclyl, carbocyclylalkyl, carbocyclylalkyloxy, and heterocyclylalkyl.

Another embodiment provides the compound of Formula (Ib), or a pharmaceutically acceptable salt thereof, wherein $R^2$ is chosen from —(C$_1$-C$_6$alkylene)-(indanyl), optionally substituted with one or more groups selected from halogen, hydroxy, —CN, alkyl, alkoxy, alkylamino, aryl, carbocyclyl, carbocyclyloxy, heterocyclyl, carbocyclylalkyl, carbocyclylalkyloxy, and heterocyclylalkyl.

Another embodiment provides the compound of Formula (Ib), or a pharmaceutically acceptable salt thereof, wherein $R^2$ is chosen from —($C_1$-$C_6$alkylene)-(chromanyl), optionally substituted with one or more groups selected from halogen, hydroxy, —CN, alkyl, alkoxy, alkylamino, aryl, carbocyclyl, carbocyclyloxy, heterocyclyl, carbocyclylalkyl, carbocyclylalkyloxy, and heterocyclylalkyl.

Another embodiment provides the compound of Formula (Ib), or a pharmaceutically acceptable salt thereof, wherein $R^2$ is chosen from —($C_1$-$C_6$alkylene)-(dihydrobenzofuranyl), optionally substituted with one or more groups selected from halogen, hydroxy, —CN, alkyl, alkoxy, alkylamino, aryl, carbocyclyl, carbocyclyloxy, heterocyclyl, carbocyclylalkyl, carbocyclylalkyloxy, and heterocyclylalkyl.

Another embodiment provides the compound of Formula (Ib), or a pharmaceutically acceptable salt thereof, wherein $R^4$ is $C_1$-$C_4$alkyl. Another embodiment provides the compound of Formula (Ib), or a pharmaceutically acceptable salt thereof, wherein $R^4$ is $C_1$-$C_4$alkyl, and the alkyl is substituted with at least one fluoro. Another embodiment provides the compound of Formula (Ib), or a pharmaceutically acceptable salt thereof, wherein $R^4$ is $CH_2F$, $CHF_2$, or $CF_3$. Another embodiment provides the compound of Formula (Ib), or a pharmaceutically acceptable salt thereof, wherein $R^4$ is $CF_3$.

One embodiment provides a compound having the structure of Formula (Ic),

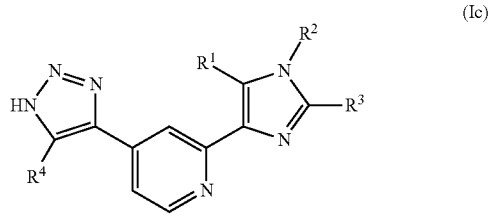

(Ic)

or a pharmaceutically acceptable salt thereof, wherein
$R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^2$ is alkyl, carbocyclyl, heterocyclyl, aryl, heteroaryl, carbocyclylalkyl, heterocyclylalkyl, aralkyl, or heteroarylalkyl;
$R^3$ is hydrogen;
$R^4$ is hydrogen, $C_1$-$C_4$alkyl, $C_1$-$C_4$alkene, $C_1$-$C_4$alkyne, halogen, or —CN; and
each $R^5$ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides the compound of Formula (Ic), or a pharmaceutically acceptable salt thereof, wherein $R^2$ is alkyl. Another embodiment provides the compound of Formula (Ic), or a pharmaceutically acceptable salt thereof, wherein $R^2$ is methyl.

Another embodiment provides the compound of Formula (Ic), or a pharmaceutically acceptable salt thereof, wherein $R^2$ is carbocyclyl or carbocyclylalkyl. Another embodiment provides the compound of Formula (Ic), or a pharmaceutically acceptable salt thereof, wherein $R^2$ is —($C_1$-$C_6$alkylene)carbocyclyl. Another embodiment provides the compound of Formula (Ic), or a pharmaceutically acceptable salt thereof, wherein carbocyclyl is 1,2,3,4-tetrahydronaphthyl optionally substituted with one or more groups selected from halogen, hydroxy, —CN, alkyl, alkoxy, alkylamino, aryl, carbocyclyl, heterocyclyl, carbocyclylalkyl, and heterocyclylalkyl. Another embodiment provides the compound of Formula (Ic), or a pharmaceutically acceptable salt thereof, wherein the ($C_1$-$C_6$alkylene) is a $C_1$alkylene, or a $C_2$alkylene. Another embodiment provides the compound of Formula (Ic), or a pharmaceutically acceptable salt thereof, wherein $R^2$ is heterocyclyl or heterocyclylalkyl. Another embodiment provides the compound of Formula (Ic), or a pharmaceutically acceptable salt thereof, wherein $R^2$ is heteroaryl or heteroarylalkyl. Another embodiment provides the compound of Formula (Ic), or a pharmaceutically acceptable salt thereof, wherein $R^2$ is aryl or aralkyl. Another embodiment provides the compound of Formula (Ic), or a pharmaceutically acceptable salt thereof, wherein the aralkyl is —($C_1$-$C_6$alkylene)aryl.

Another embodiment provides the compound of Formula (Ic), or a pharmaceutically acceptable salt thereof, wherein the aryl is a phenyl optionally substituted with one or more groups selected from halogen, hydroxy, —CN, alkyl, alkoxy, alkylamino, aryl, carbocyclyl, heterocyclyl, carbocyclylalkyl, and heterocyclylalkyl. Another embodiment provides the compound of Formula (Ic), or a pharmaceutically acceptable salt thereof, wherein ($C_1$-$C_6$alkylene) is $C_1$alkylene, or a $C_2$alkylene. Another embodiment provides the compound of Formula (Ic), or a pharmaceutically acceptable salt thereof, wherein aryl is naphthyl optionally substituted with one or more groups selected from halogen, hydroxy, —CN, alkyl, alkoxy, alkylamino, aryl, carbocyclyl, heterocyclyl, carbocyclylalkyl, and heterocyclylalkyl. Another embodiment provides the compound of Formula (Ic), or a pharmaceutically acceptable salt thereof, wherein ($C_1$-$C_6$alkylene) is $C_1$alkylene, or a $C_2$alkylene.

Another embodiment provides the compound of Formula (Ic), or a pharmaceutically acceptable salt thereof, wherein $R^1$ is hydrogen or aryl. Another embodiment provides the compound of Formula (Ic), or a pharmaceutically acceptable salt thereof, wherein $R^1$ is hydrogen. Another embodiment provides the compound of Formula (Ic), or a pharmaceutically acceptable salt thereof, wherein $R^1$ is aryl. Another embodiment provides the compound of Formula (Ic), or a pharmaceutically acceptable salt thereof, wherein the aryl is a phenyl optionally substituted with one or more groups selected from halogen, hydroxy, —CN, alkyl, alkoxy, —O-(cycloalkylalkyl), alkylamino, aryl, carbocyclyl, heterocyclyl, carbocyclylalkyl, and heterocyclylalkyl. Another embodiment provides the compound of Formula (Ic), or a pharmaceutically acceptable salt thereof, wherein the phenyl is substituted with one or more groups selected from halogen, alkoxy, or —O-(cycloalkylalkyl).

Another embodiment provides the compound of Formula (Ic), or a pharmaceutically acceptable salt thereof, wherein $R^4$ is hydrogen. Another embodiment provides the compound of Formula (Ic), or a pharmaceutically acceptable salt thereof, wherein $R^4$ is —CN. Another embodiment provides the compound of Formula (Ic), or a pharmaceutically acceptable salt thereof, wherein $R^4$ is $C_1$-$C_4$alkene, or $C_1$-$C_4$alkyne. Another embodiment provides the compound of Formula (Ic), or a pharmaceutically acceptable salt thereof, wherein $R^4$ is halogen. Another embodiment provides the compound of Formula (Ic), or a pharmaceutically acceptable salt thereof, wherein $R^4$ is $C_1$-$C_4$alkyl. Another embodiment provides the compound of Formula (Ic), or a pharmaceutically acceptable salt thereof, wherein $R^4$ is $C_1$-$C_4$alkyl, and the alkyl is substituted with at least one fluoro. Another embodiment provides the compound of Formula (Ic), or a pharmaceutically acceptable salt thereof, wherein $R^4$ is $CH_2F$, $CHF_2$, or $CF_3$. Another embodiment provides the compound of Formula (Ic), or a pharmaceutically acceptable salt thereof, wherein $R^4$ is $CF_3$.

One embodiment provides a compound having the structure of Formula (II),

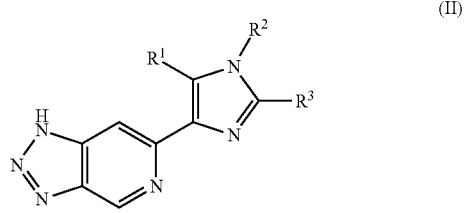

(II)

or a pharmaceutically acceptable salt thereof, wherein
$R^1$ is hydrogen, halogen, —OH, —$OR^4$, —$N(R^4)_2$, alkyl, carbocyclyl, heterocyclyl, aryl, heteroaryl, carbocyclylalkyl, heterocyclylalkyl, aralkyl, or heteroarylalkyl;
$R^2$ is alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —$NH_2$, —NH(C1-C3alkyl) or $C_1$-$C_3$alkyl; and
each $R^4$ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides a compound of Formula (II), or a pharmaceutically acceptable salt thereof, wherein $R^3$ is hydrogen.

Another embodiment provides a compound of Formula (II), or a pharmaceutically acceptable salt thereof, wherein $R^2$ is alkyl. Another embodiment provides a compound of Formula (II), or a pharmaceutically acceptable salt thereof, wherein $R^2$ is methyl.

Another embodiment provides a compound of Formula (II), or a pharmaceutically acceptable salt thereof, wherein $R^2$ is carbocyclyl or carbocyclylalkyl. Another embodiment provides a compound of Formula (II), or a pharmaceutically acceptable salt thereof, wherein $R^2$ is —($C_1$-$C_6$alkylene)carbocyclyl. Another embodiment provides a compound of Formula (II), or a pharmaceutically acceptable salt thereof, wherein $R^2$ is —($C_1$-$C_6$alkylene)carbocyclyl, and the ($C_1$-$C_6$alkylene) is a $C_1$alkylene, or a $C_2$alkylene.

Another embodiment provides a compound of Formula (II), or a pharmaceutically acceptable salt thereof, wherein $R^2$ is —($C_1$-$C_6$alkylene)carbocyclyl, and the carbocyclyl is 1,2,3,4-tetrahydronaphthyl optionally substituted with one or more groups selected from halogen, hydroxy, —CN, alkyl, alkoxy, —O-(cycloalkylalkyl), alkylamino, aryl, carbocyclyl, heterocyclyl, carbocyclylalkyl, and heterocyclylalkyl.

Another embodiment provides a compound of Formula (II), or a pharmaceutically acceptable salt thereof, wherein $R^2$ is heterocyclyl or heterocyclylalkyl. Another embodiment provides a compound of Formula (II), or a pharmaceutically acceptable salt thereof, wherein $R^2$ is —($C_1$-$C_6$alkylene)heterocyclyl.

Another embodiment provides a compound of Formula (II), or a pharmaceutically acceptable salt thereof, wherein $R^2$ is heteroaryl or heteroarylalkyl.

Another embodiment provides a compound of Formula (II), or a pharmaceutically acceptable salt thereof, wherein $R^2$ is heteroaryl or heteroarylalkyl, and the heteroaryl is pyridine or pyrimidine optionally substituted with one or more groups selected from halogen, hydroxy, —CN, alkyl, alkoxy, —O-(cycloalkylalkyl), alkylamino, aryl, carbocyclyl, heterocyclyl, carbocyclylalkyl, and heterocyclylalkyl.

Another embodiment provides a compound of Formula (II), or a pharmaceutically acceptable salt thereof, wherein $R^2$ is heteroaryl, and the heteroaryl is a chromanyl optionally substituted with one or more groups selected from halogen, hydroxy, —CN, alkyl, alkoxy, —O-(cycloalkylalkyl), alkylamino, aryl, carbocyclyl, heterocyclyl, carbocyclylalkyl, and heterocyclylalkyl.

Another embodiment provides a compound of Formula (II), or a pharmaceutically acceptable salt thereof, wherein $R^2$ is heteroarylalkyl, and the heteroarylalkyl comprises a chromanyl optionally substituted with one or more groups selected from halogen, hydroxy, —CN, alkyl, alkoxy, —O-(cycloalkylalkyl), alkylamino, aryl, carbocyclyl, heterocyclyl, carbocyclylalkyl, and heterocyclylalkyl; and a $C_1$alkylene, or a $C_2$alkylene.

Another embodiment provides a compound of Formula (II), or a pharmaceutically acceptable salt thereof, wherein $R^2$ is aryl or aralkyl.

Another embodiment provides a compound of Formula (II), or a pharmaceutically acceptable salt thereof, wherein $R^2$ is aryl or aralkyl, and the aryl is a phenyl optionally substituted with one or more groups selected from halogen, hydroxy, —CN, alkyl, alkoxy, —O-(cycloalkylalkyl), alkylamino, aryl, carbocyclyl, heterocyclyl, carbocyclylalkyl, and heterocyclylalkyl. Another embodiment provides a compound of Formula (II), or a pharmaceutically acceptable salt thereof, wherein $R^2$ is aryl or aralkyl, and the aryl is phenyl optionally substituted with one or more groups selected from halogen, alkoxy, and alkyl.

Another embodiment provides a compound of Formula (II), or a pharmaceutically acceptable salt thereof, wherein $R^2$ is aralkyl, and the aralkyl is a —($C_1$-$C_6$alkylene)aryl.

Another embodiment provides a compound of Formula (II), or a pharmaceutically acceptable salt thereof, wherein $R^2$ is aralkyl, the aralkyl is a —($C_1$-$C_6$alkylene)aryl, and the aryl is a phenyl optionally substituted with one or more groups selected from halogen, hydroxy, —CN, alkyl, alkoxy, —O-(cycloalkylalkyl), alkylamino, aryl, carbocyclyl, heterocyclyl, carbocyclylalkyl, and heterocyclylalkyl.

Another embodiment provides a compound of Formula (II), or a pharmaceutically acceptable salt thereof, wherein $R^2$ is aralkyl, the aralkyl is a —($C_1$-$C_6$alkylene)aryl, and the ($C_1$-$C_6$alkylene) is a $C_1$alkylene, or a $C_2$alkylene.

Another embodiment provides a compound of Formula (II), or a pharmaceutically acceptable salt thereof, wherein $R^2$ is aralkyl, and the aralkyl comprises a naphthyl optionally substituted with one or more groups selected from halogen, hydroxy, —CN, alkyl, alkoxy, —O-(cycloalkylalkyl), alkylamino, aryl, carbocyclyl, heterocyclyl, carbocyclylalkyl, and heterocyclylalkyl. Another embodiment provides a compound of Formula (II), or a pharmaceutically acceptable salt thereof, wherein the aralkyl further comprises a $C_1$alkylene, or a $C_2$alkylene.

Another embodiment provides a compound of Formula (II), or a pharmaceutically acceptable salt thereof, wherein $R^1$ is hydrogen or aryl. Another embodiment provides a compound of Formula (II), or a pharmaceutically acceptable salt thereof, wherein $R^1$ is hydrogen.

Another embodiment provides a compound of Formula (II), or a pharmaceutically acceptable salt thereof, wherein $R^1$ is aryl.

Another embodiment provides a compound of Formula (II), or a pharmaceutically acceptable salt thereof, wherein $R^1$ is aryl, and the aryl is a phenyl optionally substituted with one or more groups selected from halogen, hydroxy, —CN, alkyl, alkoxy, —O-(cycloalkylalkyl), alkylamino, aryl, carbocyclyl, heterocyclyl, carbocyclylalkyl, and heterocyclylalkyl. Another embodiment provides a compound of Formula (II), or a pharmaceutically acceptable salt thereof, wherein $R^1$ is aryl, and the aryl is a phenyl optionally substituted with one or more groups selected from halogen, alkoxy, or —O-(cycloalkylalkyl).

In some embodiments, the compound disclosed herein has the structure provided in Table 1.

TABLE 1

| Chemical Synthesis Example | Structure | Name |
|---|---|---|
| 1 | 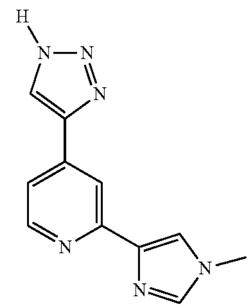 [SMILES: Cn1cnc(-c2cc(-c3c[nH]nn3)ccn2)c1] | 2-(1-methylimidazol-4-yl)-4-(1H-triazol-4-yl)pyridine |
| 2 | 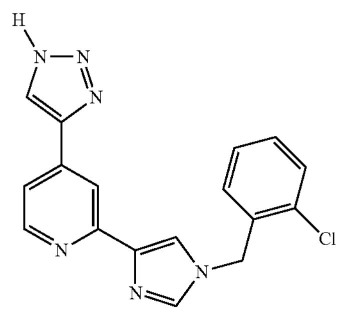 [SMILES: Clc1ccccc1Cn1cnc(-c2cc(-c3c[nH]nn3)ccn2)c1] | 2-[1-[(2-chlorophenyl)methyl]imidazol-4-yl]-4-(1H-triazol-4-yl)pyridine |
| 3 | 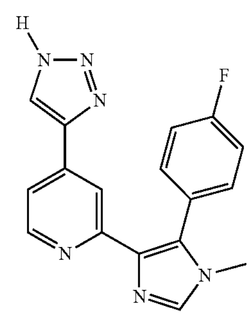 [SMILES: Cn1cnc(-c2cc(-c3c[nH]nn3)ccn2)c1-c1ccc(F)cc1] | 2-[5-(4-fluorophenyl)-1-methylimidazol-4-yl]-4-(1H-triazol-4-yl)pyridine |
| 4 | 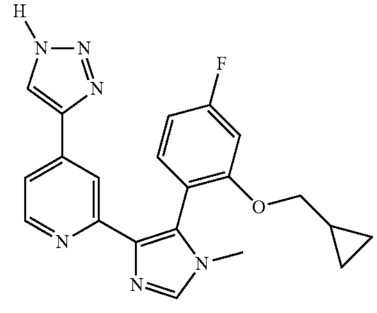 [SMILES: Cn1cnc(-c2cc(-c3c[nH]nn3)ccn2)c1-c1ccc(F)cc1OCC1CC1] | 2-[5-[2-(cyclopropylmethoxy)-4-fluorophenyl]-1-methylimidazol-4-yl]-4-(1H-triazol-4-yl)pyridine |

TABLE 1-continued

| Chemical Synthesis Example | Structure | Name |
|---|---|---|
| 5 | 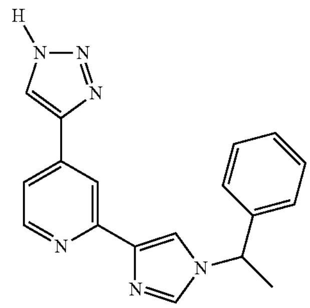 [SMILES: CC(c1ccccc1)n1cnc(-c2cc(-c3c[nH]nn3)ccn2)c1] | 2-[1-(1-phenylethyl)imidazol-4-yl]-4-(1H-triazol-4-yl)pyridine |
| 6 | 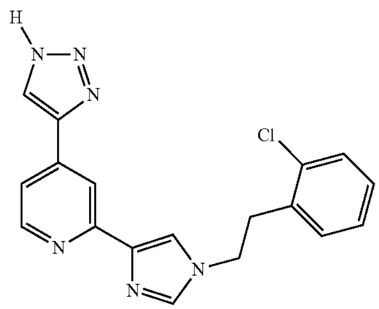 [SMILES: Clc1ccccc1CCn1cnc(-c2cc(-c3c[nH]nn3)ccn2)c1] | 2-[1-[2-(2-chlorophenyl)ethyl]imidazol-4-yl]-4-(1H-triazol-4-yl)pyridine |
| 7 | 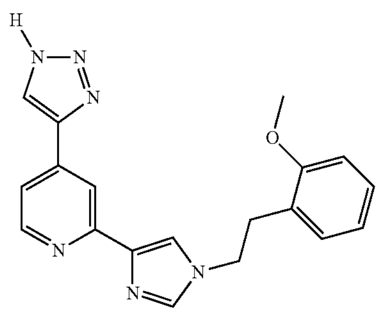 [SMILES: COc1ccccc1CCn1cnc(-c2cc(-c3c[nH]nn3)ccn2)c1] | 2-[1-[2-(2-methoxyphenyl)ethyl]imidazol-4-yl]-4-(1H-triazol-4-yl)pyridine |
| 8 | 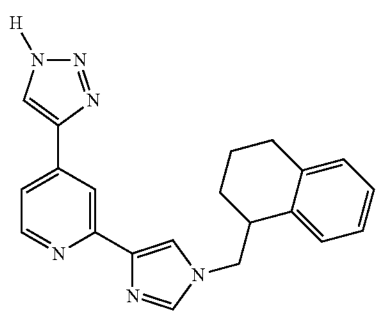 [SMILES: c1ccc2c(c1)CCCC2Cn1cnc(-c2cc(-c3c[nH]nn3)ccn2)c1] | 2-[1-(1,2,3,4-tetrahydronaphthalen-1-ylmethyl)imidazol-4-yl]-4-(1H-triazol-4-yl)pyridine |
| 9 | 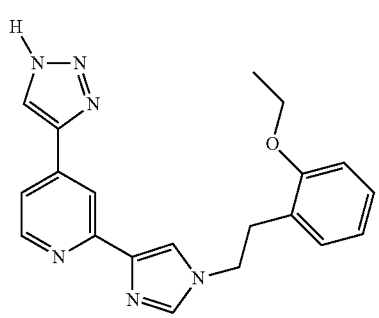 [SMILES: CCOc1ccccc1CCn1cnc(-c2cc(-c3c[nH]nn3)ccn2)c1] | 2-[1-[2-(2-ethoxyphenyl)ethyl]imidazol-4-yl]-4-(1H-triazol-4-yl)pyridine |

TABLE 1-continued

| Chemical Synthesis Example | Structure | Name |
|---|---|---|
| 10 | 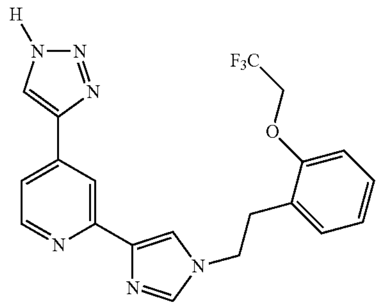 [SMILES: FC(F)(F)COc1ccccc1CCn1cnc(-c2cc(-c3c[nH]nn3)ccn2)c1] | 4-(1H-triazol-4-yl)-2-[1-[2-[2-(2,2,2-trifluoroethoxy)phenyl]ethyl]imidazol-4-yl]pyridine |
| 11 | 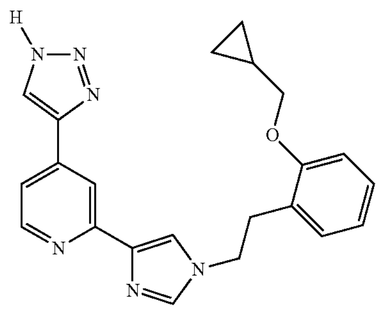 [SMILES: c1ccc(OCC2CC2)c(CCn2cnc(-c3cc(-c4c[nH]nn4)ccn3)c2)c1] | 2-[1-[2-[2-(cyclopropylmethoxy)phenyl]ethyl]imidazol-4-yl]-4-(1H-triazol-4-yl)pyridine |
| 12 | 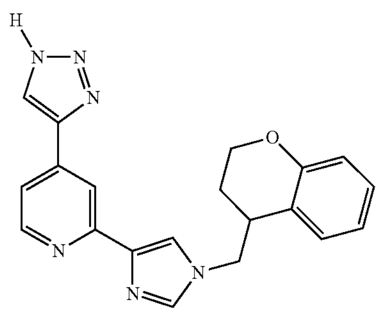 [SMILES: c1ccc2c(c1)OCCC2Cn1cnc(-c2cc(-c3c[nH]nn3)ccn2)c1] | 2-[1-(3,4-dihydro-2H-chromen-4-ylmethyl)imidazol-4-yl]-4-(1H-triazol-4-yl)pyridine |
| 13 | 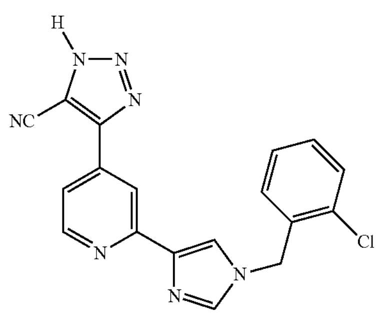 [SMILES: N#Cc1[nH]nnc1-c1ccnc(-c2cn(Cc3ccccc3Cl)cn2)c1] | 4-[2-[1-[(2-chlorophenyl)methyl]imidazol-4-yl]pyridin-4-yl]-1H-triazole-5-carbonitrile |
| 14 | 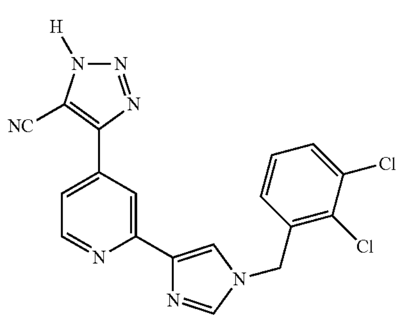 [SMILES: N#Cc1[nH]nnc1-c1ccnc(-c2cn(Cc3cccc(Cl)c3Cl)cn2)c1] | 4-[2-[1-[(2,3-dichlorophenyl)methyl]imidazol-4-yl]pyridin-4-yl]-1H-triazole-5-carbonitrile |

TABLE 1-continued

| Chemical Synthesis Example | Structure | Name |
|---|---|---|
| 15 | 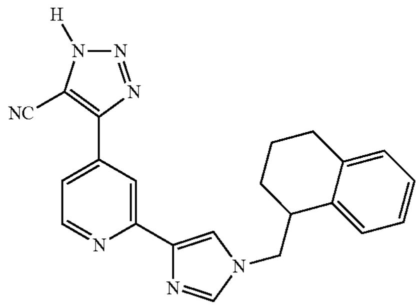 [SMILES: N#Cc1[nH]nnc1-c1ccnc(-c2cn(CC3CCCc4ccccc43)cn2)c1] | 4-[2-[1-(1,2,3,4-tetrahydronaphthalen-1-ylmethyl)imidazol-4-yl]pyridin-4-yl]-1H-triazole-5-carbonitrile |
| 16 | 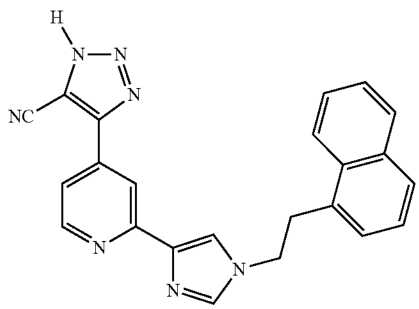 [SMILES: N#Cc1[nH]nnc1-c1ccnc(-c2cn(CCc3cccc4ccccc34)cn2)c1] | 4-[2-[1-(2-naphthalen-1-ylethyl)imidazol-4-yl]pyridin-4-yl]-1H-triazole-5-carbonitrile |
| 17 | 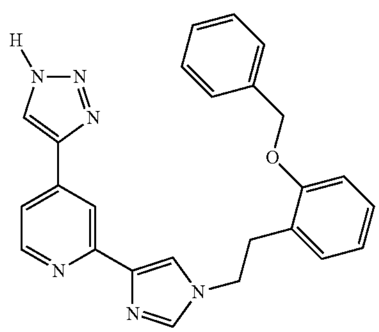 [SMILES: c1ccc(COc2ccccc2CCn2cnc(-c3cc(-c4c[nH]nn4)ccn3)c2)cc1] | 2-[1-[2-(2-phenylmethoxyphenyl)ethyl]imidazol-4-yl]-4-(1H-triazol-4-yl)pyridine |
| 18 | 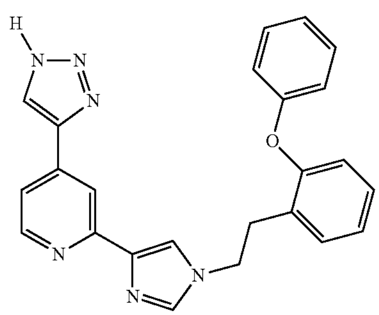 [SMILES: c1ccc(Oc2ccccc2CCn2cnc(-c3cc(-c4c[nH]nn4)ccn3)c2)cc1] | 2-[1-[2-(2-phenoxyphenyl)ethyl]imidazol-4-yl]-4-(1H-triazol-4-yl)pyridine |
| 19 | 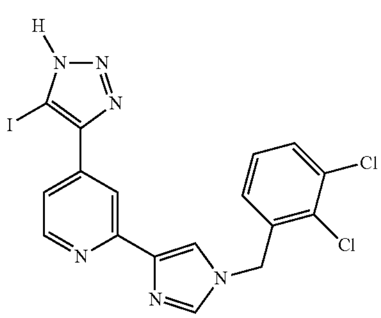 [SMILES: Clc1cccc(Cn2cnc(-c3cc(-c4nn[nH]c4I)ccn3)c2)c1Cl] | 2-[1-[(2,3-dichlorophenyl)methyl]imidazol-4-yl]-4-(5-iodo-1H-triazol-4-yl)pyridine |

TABLE 1-continued

| Chemical Synthesis Example | Structure | Name |
|---|---|---|
| 20 | 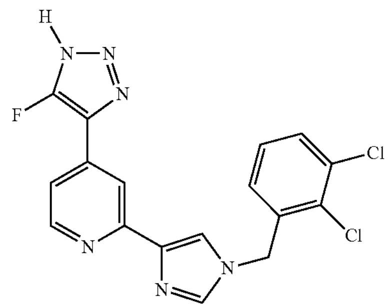 [SMILES: Fc1[nH]nnc1-c1ccnc(-c2cn(Cc3cccc(Cl)c3Cl)cn2)c1] | 2-[1-[(2,3-dichlorophenyl)methyl]imidazol-4-yl]-4-(5-fluoro-1H-triazol-4-yl)pyridine |
| 21 | 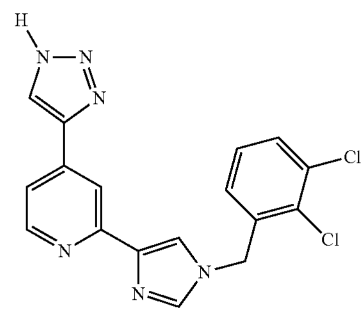 [SMILES: Clc1cccc(Cn2cnc(-c3cc(-c4c[nH]nn4)ccn3)c2)c1Cl] | 2-[1-[(2,3-dichlorophenyl)methyl]imidazol-4-yl]-4-(1H-triazol-4-yl)pyridine |
| 22 | 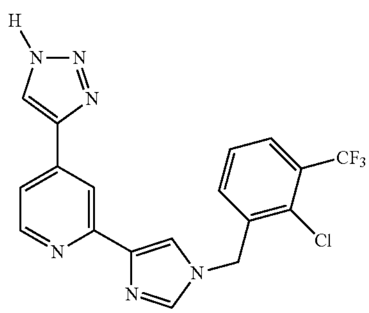 [SMILES: FC(F)(F)c1cccc(Cn2cnc(-c3cc(-c4c[nH]nn4)ccn3)c2)c1Cl] | 2-[1-[[2-chloro-3-(trifluoromethyl)phenyl]methyl]imidazol-4-yl]-4-(1H-triazol-4-yl)pyridine |
| 23 | 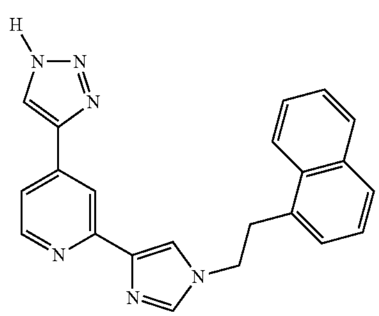 [SMILES: c1ccc2c(CCn3cnc(-c4cc(-c5c[nH]nn5)ccn4)c3)cccc2c1] | 2-[1-(2-naphthalen-1-ylethyl)imidazol-4-yl]-4-(1H-triazol-4-yl)pyridine |
| 24 | 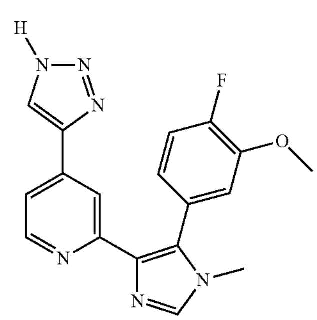 [SMILES: COc1cc(-c2c(-c3cc(-c4c[nH]nn4)ccn3)ncn2C)ccc1F] | 2-[5-(4-fluoro-3-methoxyphenyl)-1-methylimidazol-4-yl]-4-(1H-triazol-4-yl)pyridine |

TABLE 1-continued

| Chemical Synthesis Example | Structure | Name |
|---|---|---|
| 25 | 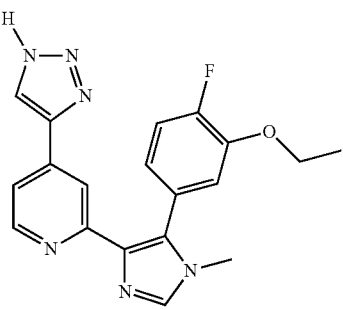 [SMILES: CCOc1cc(-c2c(-c3cc(-c4c[nH]nn4)ccn3)ncn2C)ccc1F] | 2-[5-(3-ethoxy-4-fluorophenyl)-1-methylimidazol-4-yl]-4-(1H-triazol-4-yl)pyridine |
| 26 | 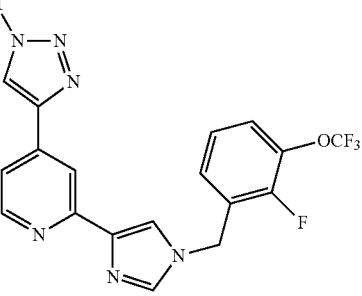 | 2-[1-[[2-fluoro-3-(trifluoromethoxy)phenyl]methyl]imidazol-4-yl]-4-(1H-triazol-4-yl)pyridine |
| 27 | 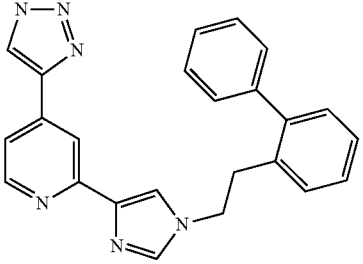 | 2-[1-[2-(2-phenylphenyl)ethyl]imidazol-4-yl]-4-(1H-triazol-4-yl)pyridine |
| 28 | 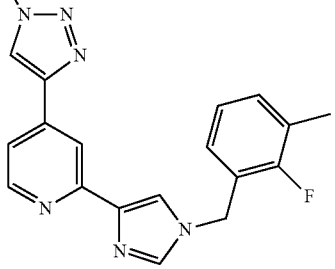 | 2-[1-[(2-fluoro-3-methylphenyl)methyl]imidazol-4-yl]-4-(1H-triazol-4-yl)pyridin |
| 29 | 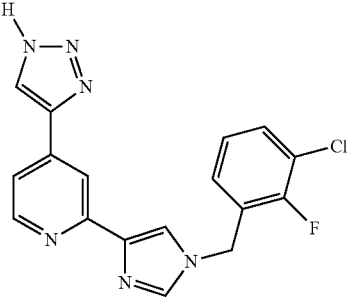 [SMILES: Fc1c(Cl)cccc1Cn1cnc(-c2cc(-c3c[nH]nn3)ccn2)c1] | 2-[1-[(3-chloro-2-fluorophenyl)methyl]imidazol-4-yl]-4-(1H-triazol-4-yl)pyridine |

TABLE 1-continued

| Chemical Synthesis Example | Structure | Name |
|---|---|---|
| 30 | 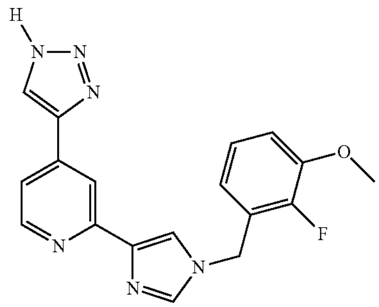 [SMILES: COc1cccc(Cn2cnc(-c3cc(-c4c[nH]nn4)ccn3)c2)c1F] | 2-[1-[(2-fluoro-3-methoxyphenyl)methyl]imidazol-4-yl]-4-(1H-triazol-4-yl)pyridine |
| 31 | 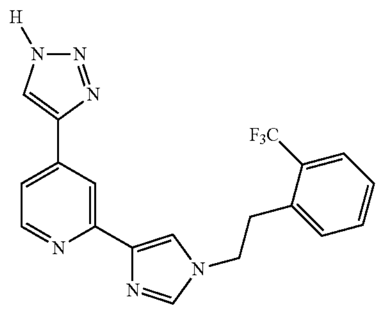 | 4-(1H-triazol-4-yl)-2-[1-[2-[2-(trifluoromethyl)phenyl]ethyl]imidazol-4-yl]pyridine |
| 32 | 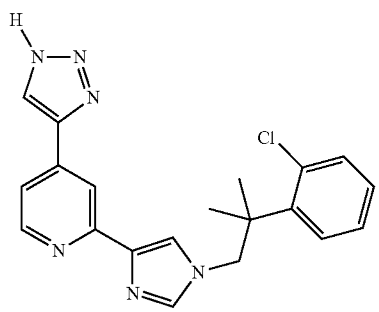 [SMILES: CC(C)(Cn1cnc(-c2cc(-c3c[nH]nn3)ccn2)c1)c1ccccc1Cl] | 2-[1-[2-(2-chlorophenyl)-2-methylpropyl]imidazol-4-yl]-4-(1H-triazol-4-yl)pyridine |
| 33 | 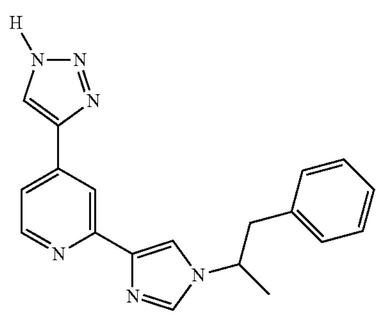 [SMILES: CC(Cc1ccccc1)n1cnc(-c2cc(-c3c[nH]nn3)ccn2)c1] | 2-[1-(1-phenylpropan-2-yl)imidazol-4-yl]-4-(1H-triazol-4-yl)pyridine |
| 34 | 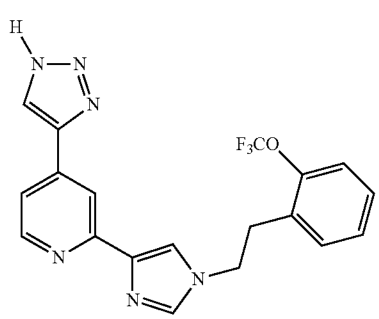 [SMILES: FC(F)(F)Oc1ccccc1CCn1cnc(-c2cc(-c3c[nH]nn3)ccn2)c1] | 4-(1H-triazol-4-yl)-2-[1-[2-[2-(trifluoromethoxy)phenyl]ethyl]imidazol-4-yl]pyridine |

TABLE 1-continued

| Chemical Synthesis Example | Structure | Name |
|---|---|---|
| 35 | 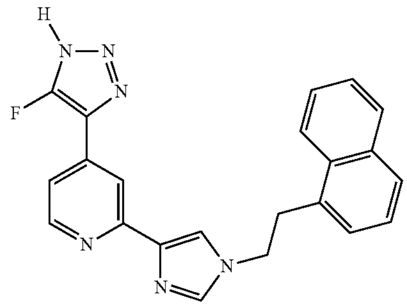 [SMILES: Fc1[nH]nnc1-c1ccnc(-c2cn(CCc3cccc4ccccc34)cn2)c1] | 4-(5-fluoro-1H-triazol-4-yl)-2-[1-(2-naphthalen-1-ylethyl)imidazol-4-yl]pyridine |
| 36 | 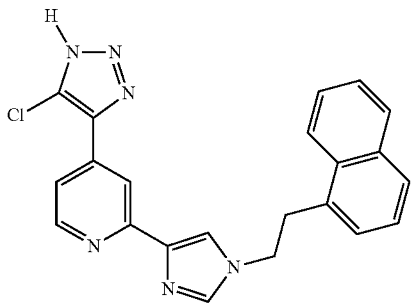 [SMILES: Clc1[nH]nnc1-c1ccnc(-c2cn(CCc3cccc4ccccc34)cn2)c1] | 4-(5-chloro-1H-triazol-4-yl)-2-[1-(2-naphthalen-1-ylethyl)imidazol-4-yl]pyridine |
| 37 | 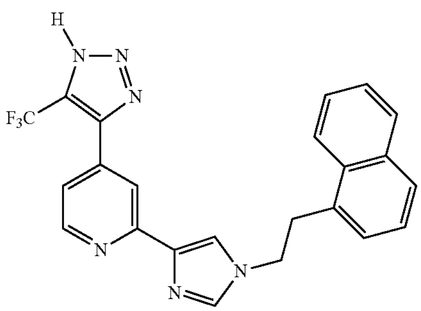 [SMILES: FC(F)(F)c1[nH]nnc1-c1ccnc(-c2cn(CCc3cccc4ccccc34)cn2)c1] | 2-[1-(2-naphthalen-1-ylethyl)imidazol-4-yl]-4-[5-(trifluoromethyl)-1H-triazol-4-yl]pyridine |
| 38 | 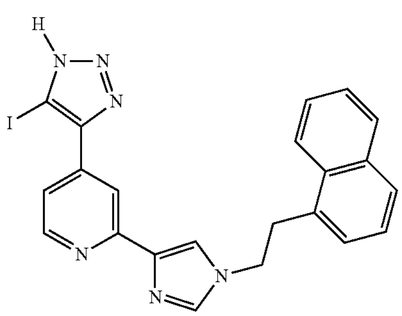 [SMILES: Ic1[nH]nnc1-c1ccnc(-c2cn(CCc3cccc4ccccc34)cn2)c1] | 4-(5-iodo-1H-triazol-4-yl)-2-[1-(2-naphthalen-1-ylethyl)imidazol-4-yl]pyridine |
| 39 | 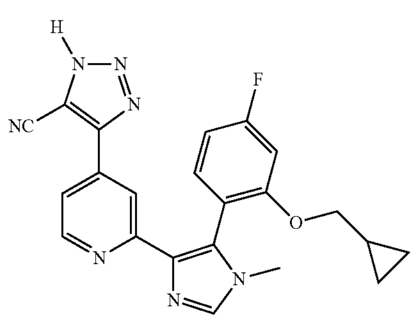 [SMILES: Cn1cnc(-c2cc(-c3nn[nH]c3C#N)ccn2)c1-c1ccc(F)cc1OCC1CC1] | 4-[2-[5-[2-(cyclopropylmethoxy)-4-fluorophenyl]-1-methylimidazol-4-yl]pyridin-4-yl]-1H-triazole-5-carbonitrile |

TABLE 1-continued

| Chemical Synthesis Example | Structure | Name |
|---|---|---|
| 40 | 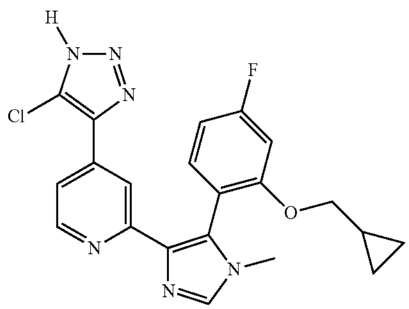 [SMILES: Cn1cnc(-c2cc(-c3nn[nH]c3Cl)ccn2)c1-c1ccc(F)cc1OCC1CC1] | 4-(5-chloro-1H-triazol-4-yl)-2-[5-[2-(cyclopropylmethoxy)-4-fluorophenyl]-1-methylimidazol-4-yl]pyridine |
| 41 | 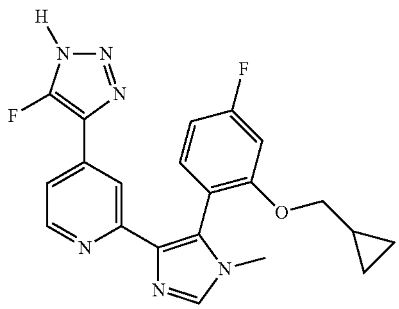 [SMILES: Cn1cnc(-c2cc(-c3nn[nH]c3F)ccn2)c1-c1ccc(F)cc1OCC1CC1] | 2-[5-[2-(cyclopropylmethoxy)-4-fluorophenyl]-1-methylimidazol-4-yl]-4-(5-fluoro-1H-triazol-4-yl)pyridine |
| 42 | 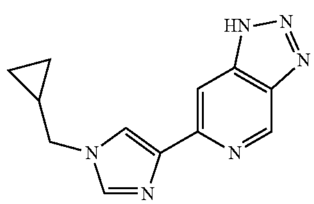 [SMILES: c1nc(-c2cn(CC3CC3)cn2)cc2[nH]nnc12] | 1-(cyclopropylmethyl)-4-{1H-[1,2,3]triazolo[4,5-c]pyridin-6-yl}-1H-imidazole |
| 43 | 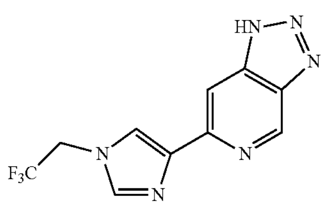 [SMILES: FC(F)(F)Cn1cnc(-c2cc3[nH]nnc3cn2)c1] | 4-{1H-[1,2,3]triazolo[4,5-c]pyridin-6-yl}-1-(2,2,2-trifluoroethyl)-1H-imidazole |
| 44 | 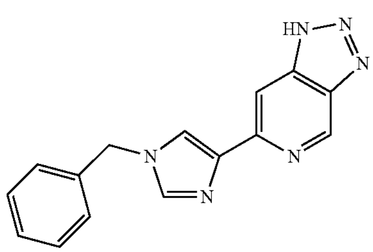 [SMILES: c1ccc(Cn2cnc(-c3cc4[nH]nnc4cn3)c2)cc1] | 1-benzyl-4-{1H-[1,2,3]triazolo[4,5-c]pyridin-6-yl}-1H-imidazole |
| 45 | 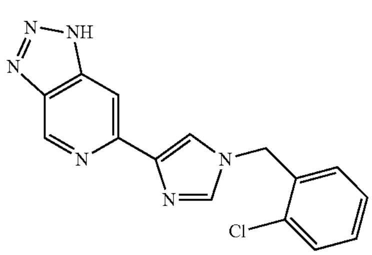 [SMILES: Clc1ccccc1Cn1cnc(-c2cc3[nH]nnc3cn2)c1] | 1-[(2-chlorophenyl)methyl]-4-{1H-[1,2,3]triazolo[4,5-c]pyridin-6-yl}-1H-imidazole |

TABLE 1-continued

| Chemical Synthesis Example | Structure | Name |
|---|---|---|
| 46 | 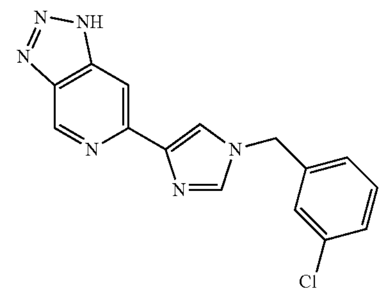 [SMILES: Clc1cccc(Cn2cnc(-c3cc4[nH]nnc4cn3)c2)c1] | 1-[(3-chlorophenyl)methyl]-4-{1H-[1,2,3]triazolo[4,5-c]pyridin-6-yl}-1H-imidazole |
| 47 | 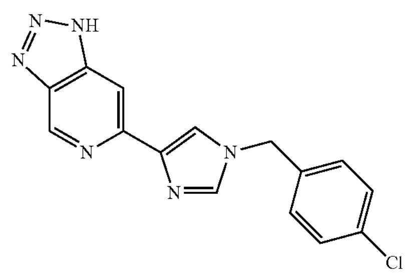 [SMILES: Clc1ccc(Cn2cnc(-c3cc4[nH]nnc4cn3)c2)cc1] | 1-[(4-chlorophenyl)methyl]-4-{1H-[1,2,3]triazolo[4,5-c]pyridin-6-yl}-1H-imidazole |
| 48 | 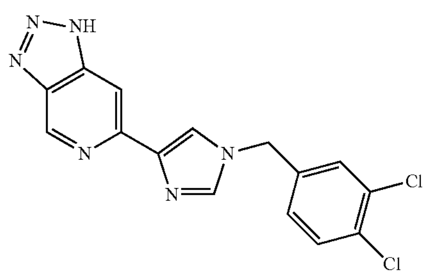 [SMILES: Clc1ccc(Cn2cnc(-c3cc4[nH]nnc4cn3)c2)cc1Cl] | 1-[(3,4-dichlorophenyl)methyl]-4-{1H-[1,2,3]triazolo[4,5-c]pyridin-6-yl}-1H-imidazole |
| 49 | 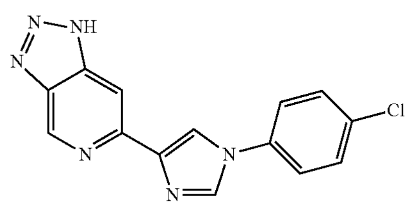 [SMILES: Clc1ccc(-n2cnc(-c3cc4[nH]nnc4cn3)c2)cc1] | 1-(4-chlorophenyl)-4-{1H-[1,2,3]triazolo[4,5-c]pyridin-6-yl}-1H-imidazole |
| 50 | 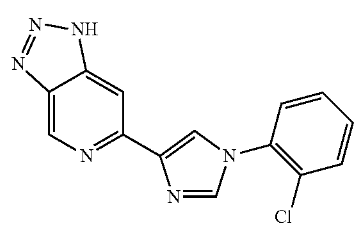 [SMILES: Clc1ccccc1-n1cnc(-c2cc3[nH]nnc3cn2)c1] | 1-(2-chlorophenyl)-4-{1H-[1,2,3]triazolo[4,5-c]pyridin-6-yl}-1H-imidazole |
| 51 | 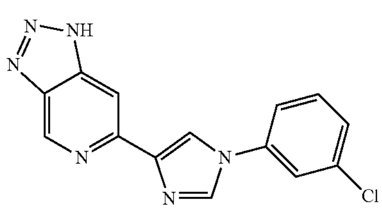 [SMILES: Clc1cccc(-n2cnc(-c3cc4[nH]nnc4cn3)c2)c1] | 1-(3-chlorophenyl)-4-{1H-[1,2,3]triazolo[4,5-c]pyridin-6-yl}-1H-imidazole |

TABLE 1-continued

| Chemical Synthesis Example | Structure | Name |
|---|---|---|
| 52 | 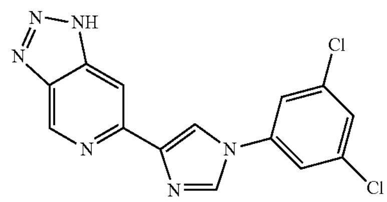 [SMILES: Clc1cc(Cl)cc(-n2cnc(-c3cc4[nH]nnc4cn3)c2)c1] | 1-(3,5-dichlorophenyl)-4-{1H-[1,2,3]triazolo[4,5-c]pyridin-6-yl}-1H-imidazole |
| 53 | 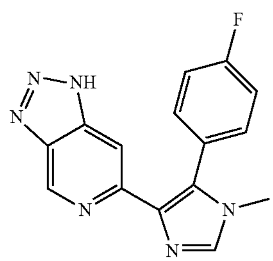 [SMILES: Cn1cnc(-c2cc3[nH]nnc3cn2)c1-c1ccc(F)cc1] | 5-(4-fluorophenyl)-1-methyl-4-{1H-[1,2,3]triazolo[4,5-c]pyridin-6-yl}-1H-imidazole |
| 54 | 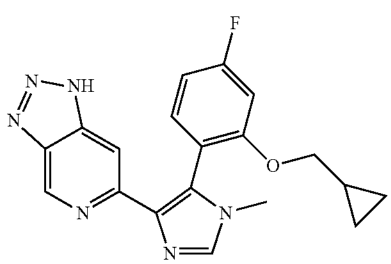 [SMILES: Cn1cnc(-c2cc3[nH]nnc3cn2)c1-c1ccc(F)cc1OCC1CC1] | 5-[2-(cyclopropylmethoxy)-4-fluorophenyl]-1-methyl-4-{1H-[1,2,3]triazolo[4,5-c]pyridin-6-yl}-1H-imidazole |
| 55 | 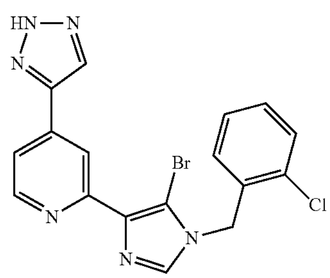 [SMILES: Clc1ccccc1Cn1cnc(-c2cc(-c3cn[nH]n3)ccn2)c1Br] | 2-(5-bromo-1-(2-chlorobenzyl)-1H-imidazol-4-yl)-4-(2H-1,2,3-triazol-4-yl)pyridine |
| 56 | 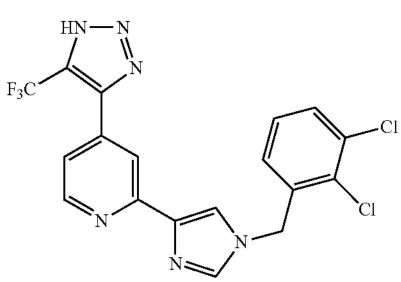 [SMILES: FC(F)(F)c1[nH]nnc1-c1ccnc(-c2cn(Cc3cccc(Cl)c3Cl)cn2)c1] | 2-[1-[(2,3-dichlorophenyl)methyl]imidazol-4-yl]-4-(5-trifluoromethyl-1H-triazol-4-yl)pyridine |

In some embodiments, the compound disclosed herein has the structure provided in Table 2.
TABLE 2
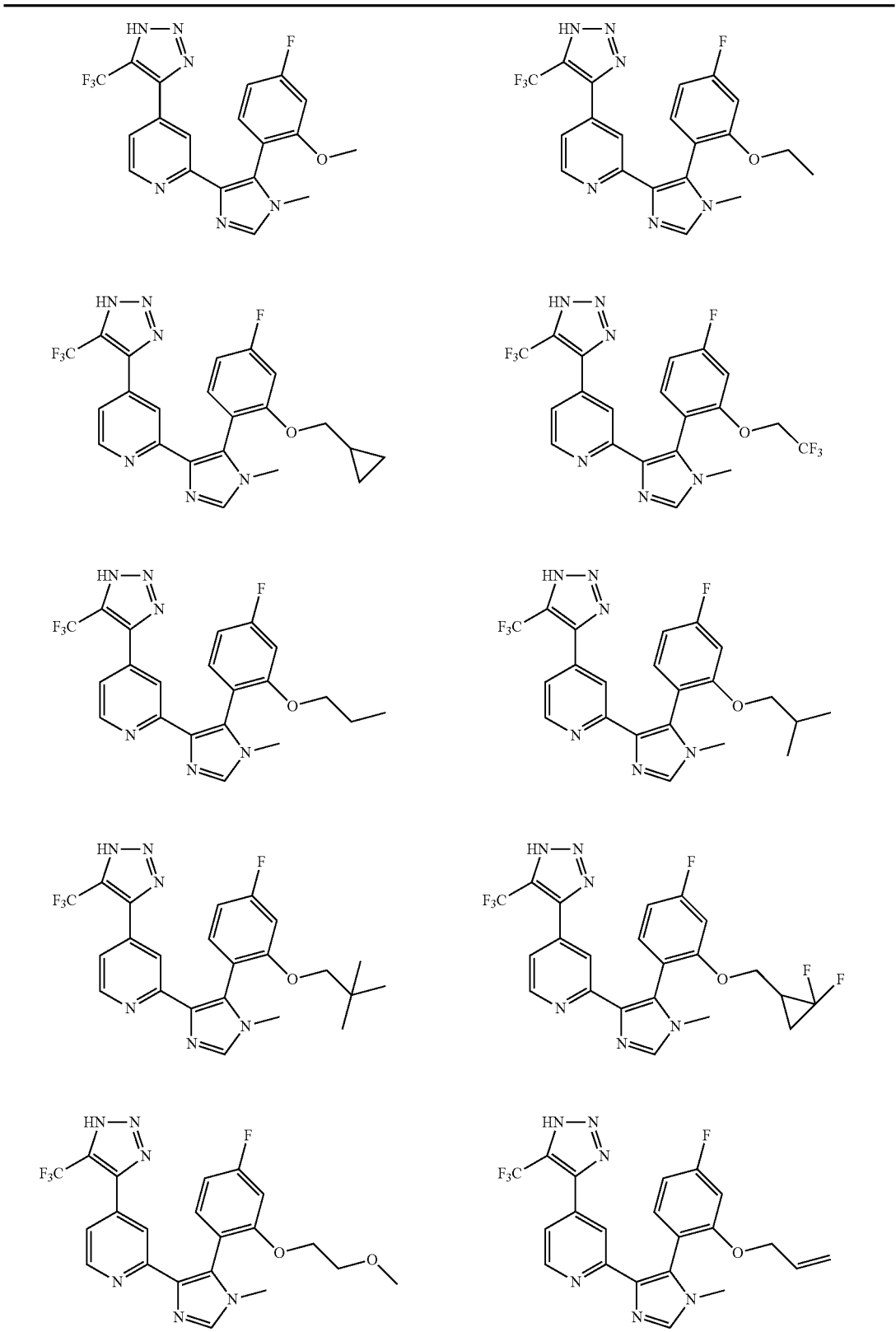

TABLE 2-continued
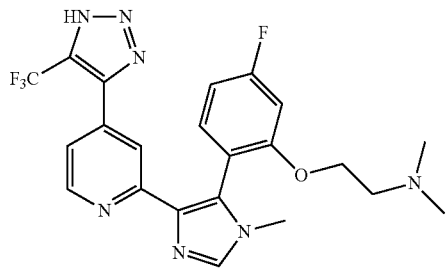 [SMILES: CN(C)CCOc1cc(F)ccc1-c1c(-c2cc(-c3nn[nH]c3C(F)(F)F)ccn2)ncn1C] 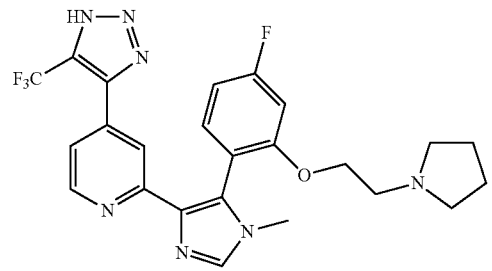 [SMILES: Cn1cnc(-c2cc(-c3nn[nH]c3C(F)(F)F)ccn2)c1-c1ccc(F)cc1OCCN1CCCC1]
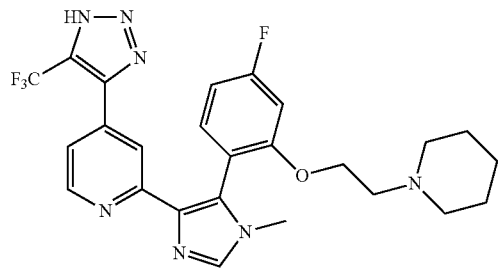 [SMILES: Cn1cnc(-c2cc(-c3nn[nH]c3C(F)(F)F)ccn2)c1-c1ccc(F)cc1OCCN1CCCCC1] 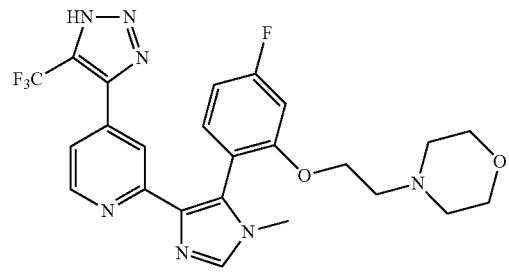 [SMILES: Cn1cnc(-c2cc(-c3nn[nH]c3C(F)(F)F)ccn2)c1-c1ccc(F)cc1OCCN1CCOCC1]
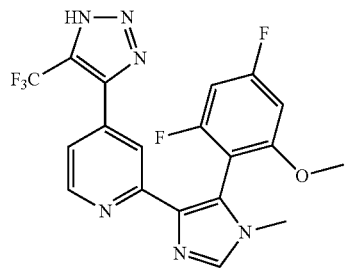 [SMILES: COc1cc(F)cc(F)c1-c1c(-c2cc(-c3nn[nH]c3C(F)(F)F)ccn2)ncn1C] 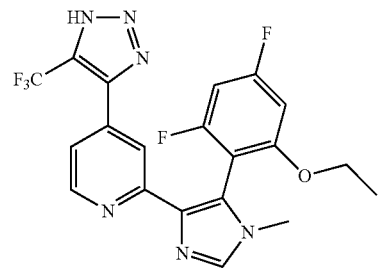 [SMILES: CCOc1cc(F)cc(F)c1-c1c(-c2cc(-c3nn[nH]c3C(F)(F)F)ccn2)ncn1C]
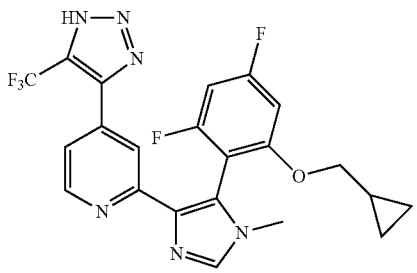 [SMILES: Cn1cnc(-c2cc(-c3nn[nH]c3C(F)(F)F)ccn2)c1-c1c(F)cc(F)cc1OCC1CC1] 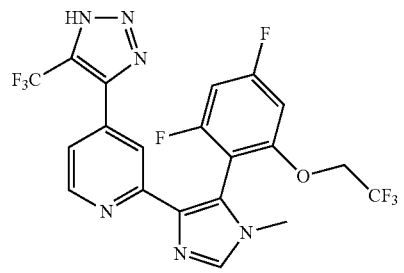 [SMILES: Cn1cnc(-c2cc(-c3nn[nH]c3C(F)(F)F)ccn2)c1-c1c(F)cc(F)cc1OCC(F)(F)F]
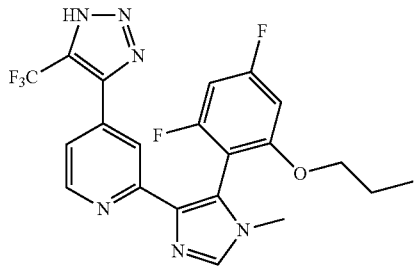 [SMILES: CCCOc1cc(F)cc(F)c1-c1c(-c2cc(-c3nn[nH]c3C(F)(F)F)ccn2)ncn1C] 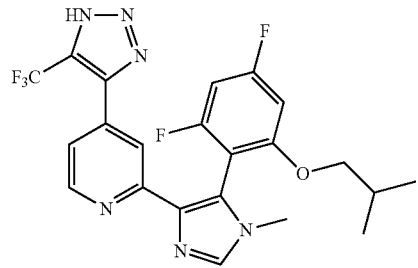 [SMILES: CC(C)COc1cc(F)cc(F)c1-c1c(-c2cc(-c3nn[nH]c3C(F)(F)F)ccn2)ncn1C]
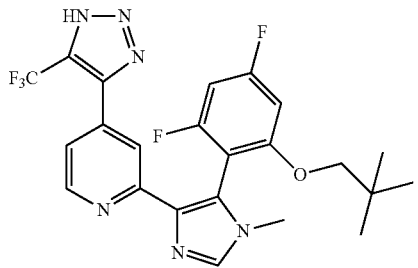 [SMILES: Cn1cnc(-c2cc(-c3nn[nH]c3C(F)(F)F)ccn2)c1-c1c(F)cc(F)cc1OCC(C)(C)C] 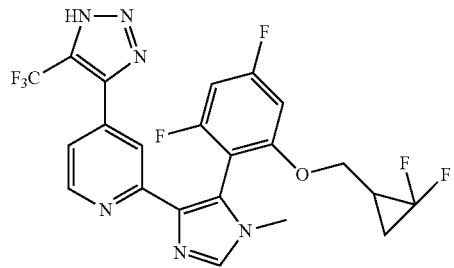 [SMILES: Cn1cnc(-c2cc(-c3nn[nH]c3C(F)(F)F)ccn2)c1-c1c(F)cc(F)cc1OCC1CC1(F)F]

TABLE 2-continued
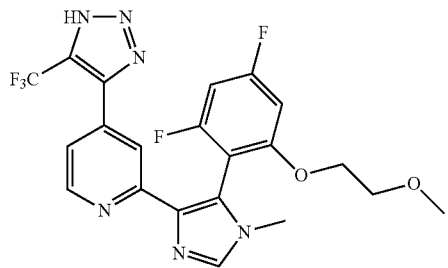 [SMILES: COCCOc1cc(F)cc(F)c1-c1c(-c2cc(-c3nn[nH]c3C(F)(F)F)ccn2)ncn1C] 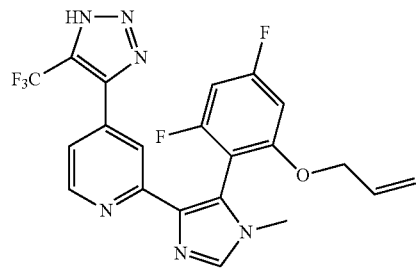
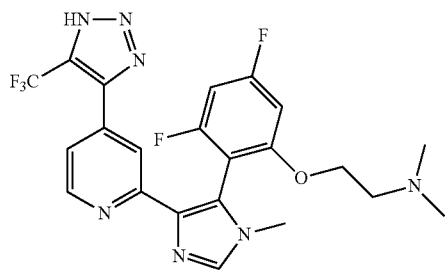 [SMILES: CN(C)CCOc1cc(F)cc(F)c1-c1c(-c2cc(-c3nn[nH]c3C(F)(F)F)ccn2)ncn1C] 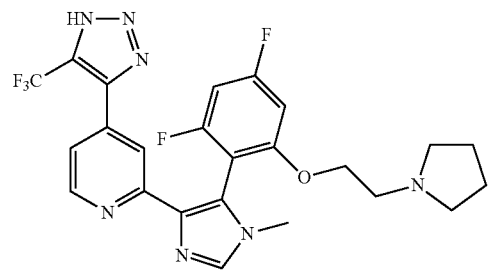 [SMILES: Cn1cnc(-c2cc(-c3nn[nH]c3C(F)(F)F)ccn2)c1-c1c(F)cc(F)cc1OCCN1CCCC1]
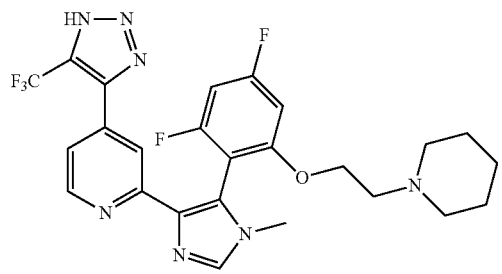 [SMILES: Cn1cnc(-c2cc(-c3nn[nH]c3C(F)(F)F)ccn2)c1-c1c(F)cc(F)cc1OCCN1CCCCC1] 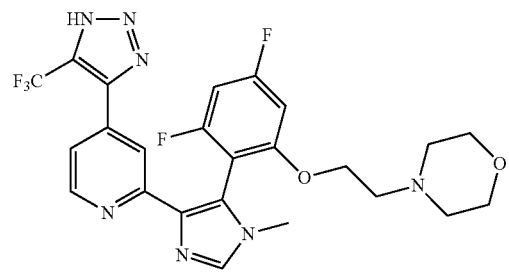 [SMILES: Cn1cnc(-c2cc(-c3nn[nH]c3C(F)(F)F)ccn2)c1-c1c(F)cc(F)cc1OCCN1CCOCC1]
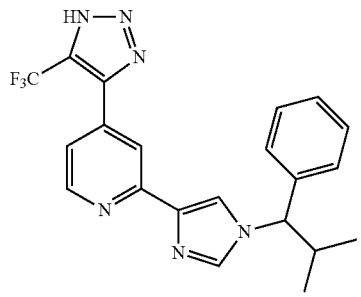 [SMILES: CC(C)C(c1ccccc1)n1cnc(-c2cc(-c3nn[nH]c3C(F)(F)F)ccn2)c1] 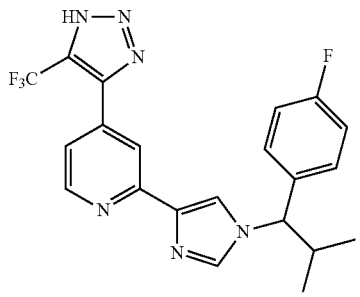 [SMILES: CC(C)C(c1ccc(F)cc1)n1cnc(-c2cc(-c3nn[nH]c3C(F)(F)F)ccn2)c1]
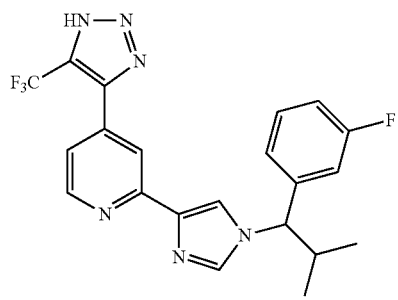 [SMILES: CC(C)C(c1cccc(F)c1)n1cnc(-c2cc(-c3nn[nH]c3C(F)(F)F)ccn2)c1] 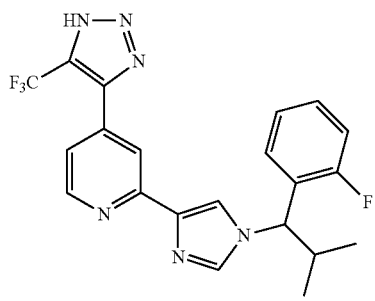 [SMILES: CC(C)C(c1ccccc1F)n1cnc(-c2cc(-c3nn[nH]c3C(F)(F)F)ccn2)c1]

TABLE 2-continued
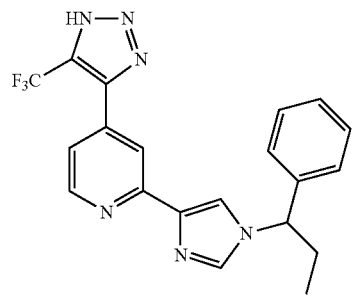 [SMILES: CCC(c1ccccc1)n1cnc(-c2cc(-c3nn[nH]c3C(F)(F)F)ccn2)c1]
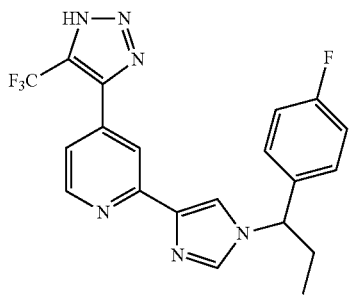 [SMILES: CCC(c1ccc(F)cc1)n1cnc(-c2cc(-c3nn[nH]c3C(F)(F)F)ccn2)c1]
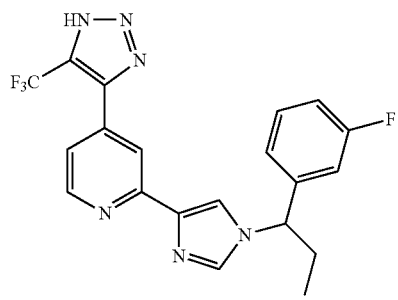 [SMILES: CCC(c1cccc(F)c1)n1cnc(-c2cc(-c3nn[nH]c3C(F)(F)F)ccn2)c1]
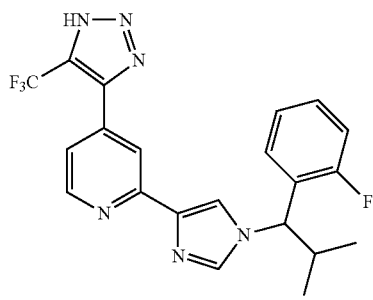 [SMILES: CC(C)C(c1ccccc1F)n1cnc(-c2cc(-c3nn[nH]c3C(F)(F)F)ccn2)c1]
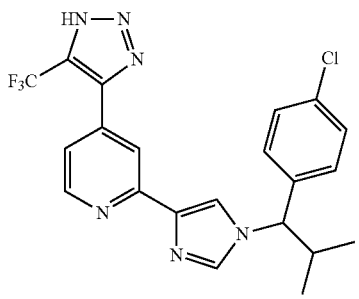 [SMILES: CC(C)C(c1ccc(Cl)cc1)n1cnc(-c2cc(-c3nn[nH]c3C(F)(F)F)ccn2)c1]
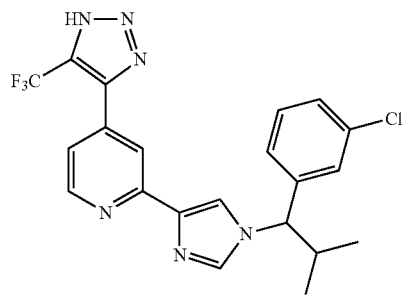 [SMILES: CC(C)C(c1cccc(Cl)c1)n1cnc(-c2cc(-c3nn[nH]c3C(F)(F)F)ccn2)c1]
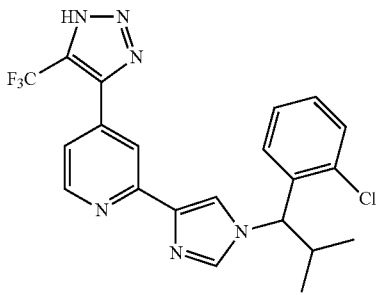 [SMILES: CC(C)C(c1ccccc1Cl)n1cnc(-c2cc(-c3nn[nH]c3C(F)(F)F)ccn2)c1]
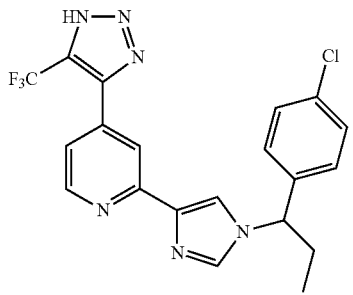 [SMILES: CCC(c1ccc(Cl)cc1)n1cnc(-c2cc(-c3nn[nH]c3C(F)(F)F)ccn2)c1]
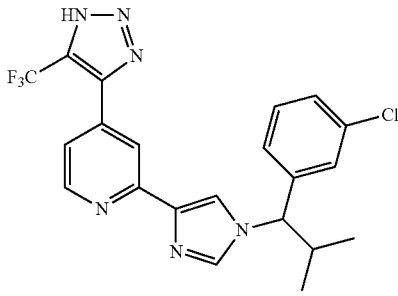 [SMILES: CC(C)C(c1cccc(Cl)c1)n1cnc(-c2cc(-c3nn[nH]c3C(F)(F)F)ccn2)c1]
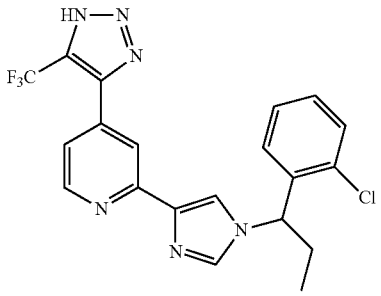 [SMILES: CCC(c1ccccc1Cl)n1cnc(-c2cc(-c3nn[nH]c3C(F)(F)F)ccn2)c1]

TABLE 2-continued
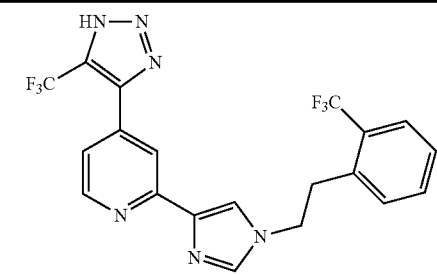
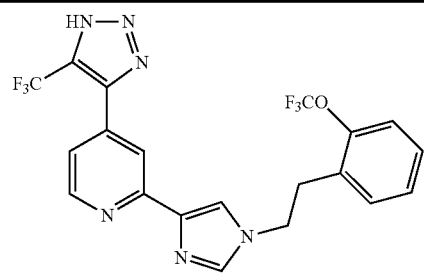
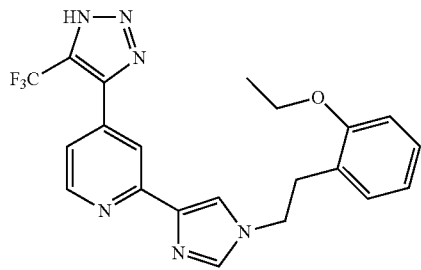 [SMILES: CCOc1ccccc1CCn1cnc(-c2cc(-c3nn[nH]c3C(F)(F)F)ccn2)c1]
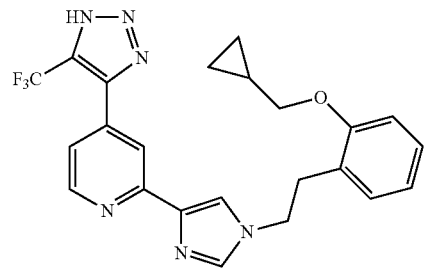 [SMILES: FC(F)(F)c1[nH]nnc1-c1ccnc(-c2cn(CCc3ccccc3OCC3CC3)cn2)c1]
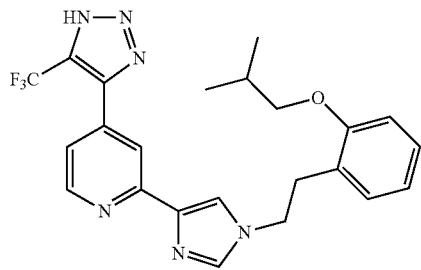 [SMILES: CC(C)COc1ccccc1CCn1cnc(-c2cc(-c3nn[nH]c3C(F)(F)F)ccn2)c1]
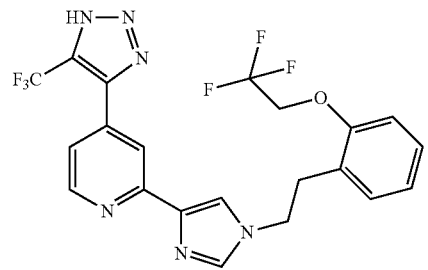 [SMILES: FC(F)(F)COc1ccccc1CCn1cnc(-c2cc(-c3nn[nH]c3C(F)(F)F)ccn2)c1]
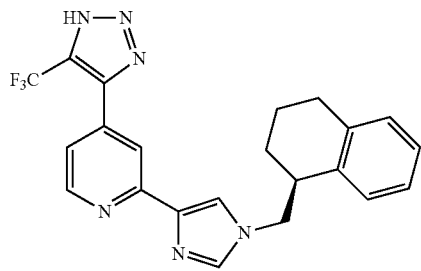 [SMILES: FC(F)(F)c1[nH]nnc1-c1ccnc(-c2cn(C[C@H]3CCCc4ccccc43)cn2)c1]
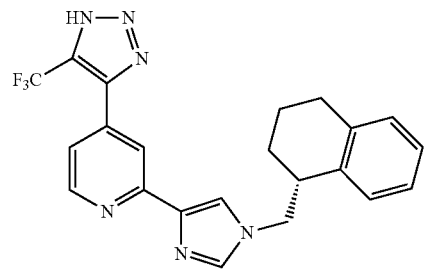 [SMILES: FC(F)(F)c1[nH]nnc1-c1ccnc(-c2cn(C[C@@H]3CCCc4ccccc43)cn2)c1]
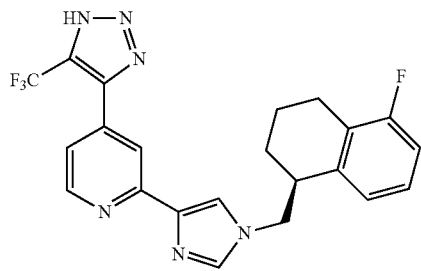 [SMILES: Fc1cccc2c1CCC[C@@H]2Cn1cnc(-c2cc(-c3nn[nH]c3C(F)(F)F)ccn2)c1]
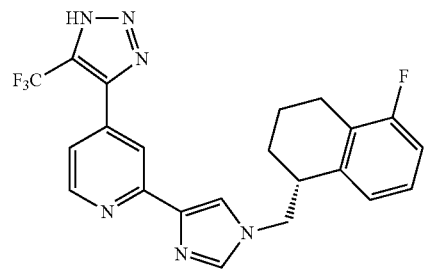 [SMILES: Fc1cccc2c1CCC[C@H]2Cn1cnc(-c2cc(-c3nn[nH]c3C(F)(F)F)ccn2)c1]
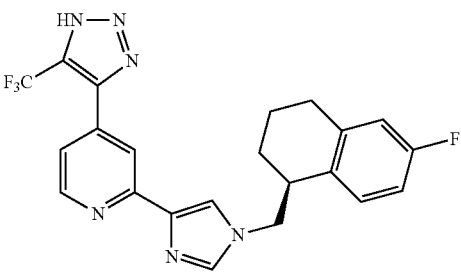 [SMILES: Fc1ccc2c(c1)CCC[C@@H]2Cn1cnc(-c2cc(-c3nn[nH]c3C(F)(F)F)ccn2)c1]
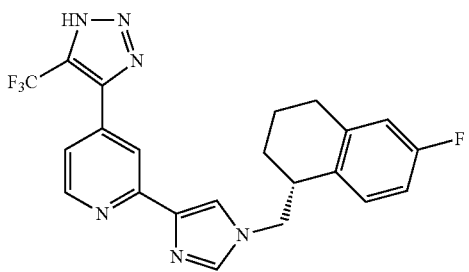 [SMILES: Fc1ccc2c(c1)CCC[C@H]2Cn1cnc(-c2cc(-c3nn[nH]c3C(F)(F)F)ccn2)c1]

TABLE 2-continued
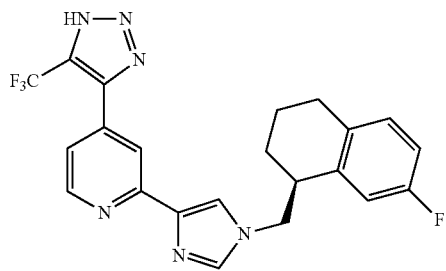 [SMILES: Fc1ccc2c(c1)[C@@H](Cn1cnc(-c3cc(-c4nn[nH]c4C(F)(F)F)ccn3)c1)CCC2]
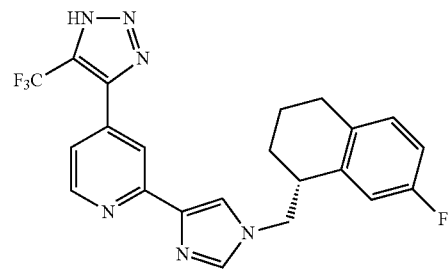 [SMILES: Fc1ccc2c(c1)[C@H](Cn1cnc(-c3cc(-c4nn[nH]c4C(F)(F)F)ccn3)c1)CCC2]
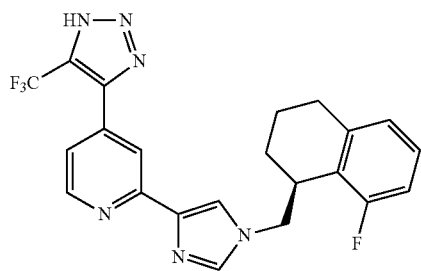
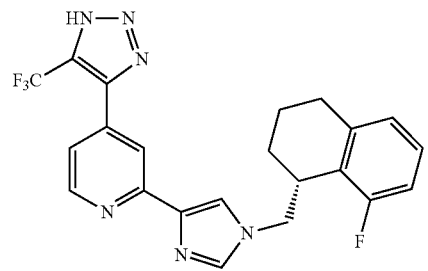
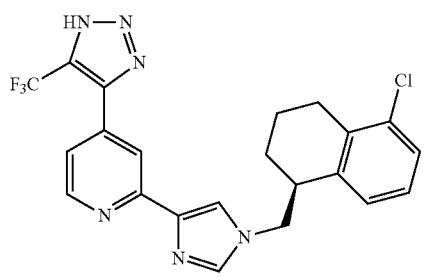
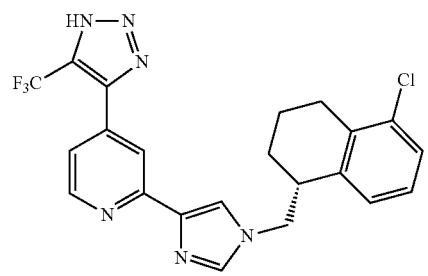
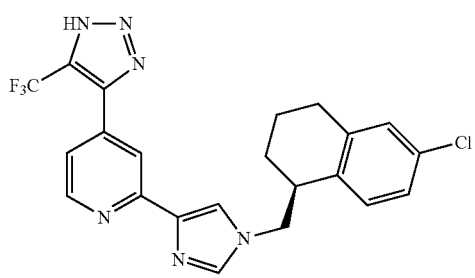 [SMILES: FC(F)(F)c1[nH]nnc1-c1ccnc(-c2cn(C[C@H]3CCCc4cc(Cl)ccc43)cn2)c1]
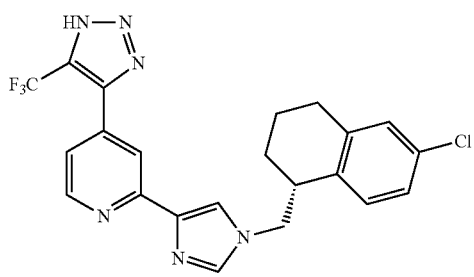 [SMILES: FC(F)(F)c1[nH]nnc1-c1ccnc(-c2cn(C[C@@H]3CCCc4cc(Cl)ccc43)cn2)c1]
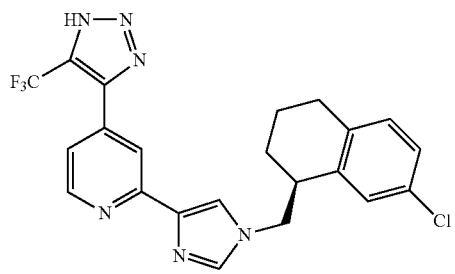 [SMILES: FC(F)(F)c1[nH]nnc1-c1ccnc(-c2cn(C[C@H]3CCCc4ccc(Cl)cc43)cn2)c1]
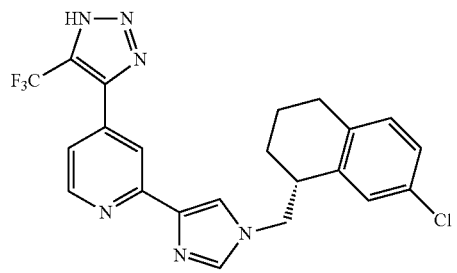 [SMILES: FC(F)(F)c1[nH]nnc1-c1ccnc(-c2cn(C[C@@H]3CCCc4ccc(Cl)cc43)cn2)c1]

TABLE 2-continued
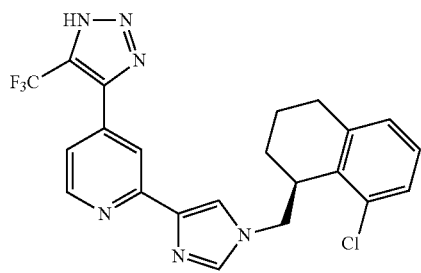 [SMILES: FC(F)(F)c1[nH]nnc1-c1ccnc(-c2cn(C[C@H]3CCCc4cccc(Cl)c43)cn2)c1] 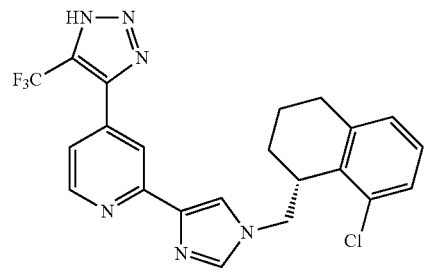 [SMILES: FC(F)(F)c1[nH]nnc1-c1ccnc(-c2cn(C[C@@H]3CCCc4cccc(Cl)c43)cn2)c1]
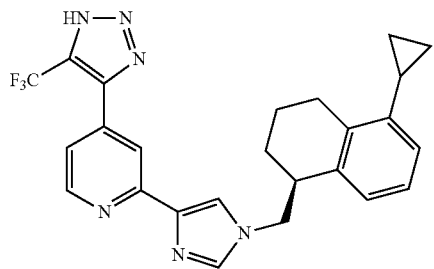 [SMILES: FC(F)(F)c1[nH]nnc1-c1ccnc(-c2cn(C[C@H]3CCCc4c(C5CC5)cccc43)cn2)c1] 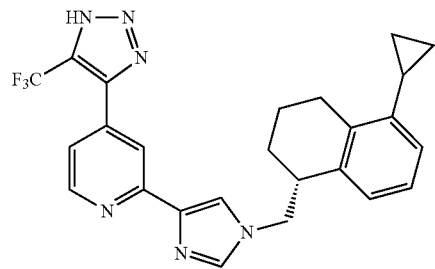 [SMILES: FC(F)(F)c1[nH]nnc1-c1ccnc(-c2cn(C[C@@H]3CCCc4c(C5CC5)cccc43)cn2)c1]
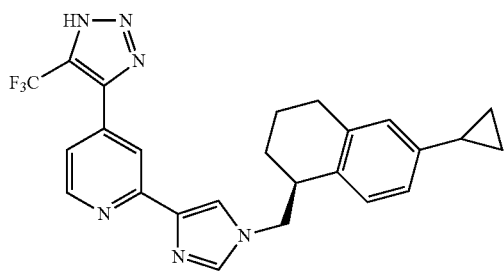 [SMILES: FC(F)(F)c1[nH]nnc1-c1ccnc(-c2cn(C[C@H]3CCCc4cc(C5CC5)ccc43)cn2)c1] 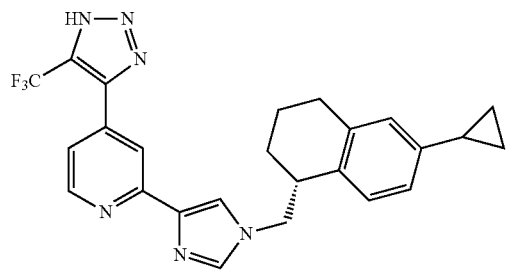 [SMILES: FC(F)(F)c1[nH]nnc1-c1ccnc(-c2cn(C[C@@H]3CCCc4cc(C5CC5)ccc43)cn2)c1]
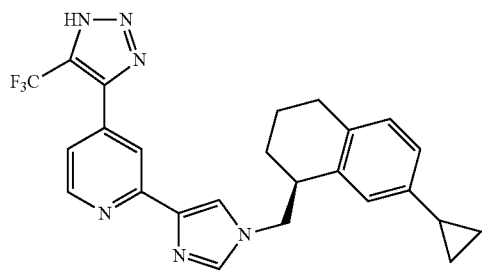 [SMILES: FC(F)(F)c1[nH]nnc1-c1ccnc(-c2cn(C[C@H]3CCCc4ccc(C5CC5)cc43)cn2)c1] 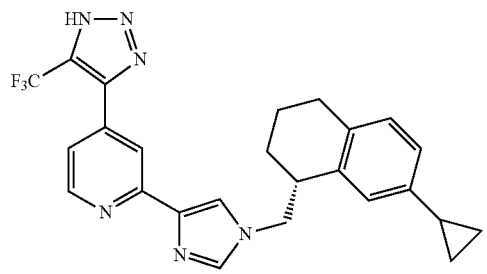 [SMILES: FC(F)(F)c1[nH]nnc1-c1ccnc(-c2cn(C[C@@H]3CCCc4ccc(C5CC5)cc43)cn2)c1]
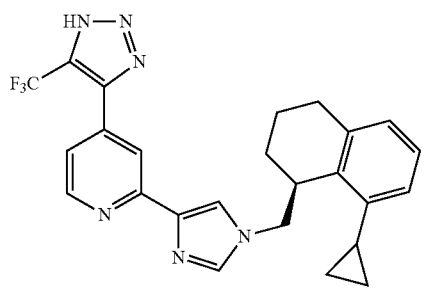 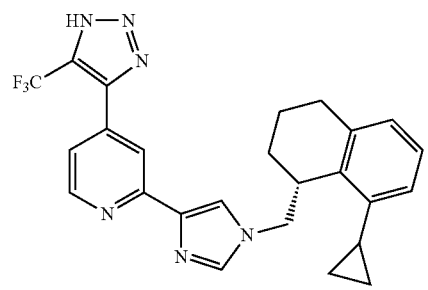 [SMILES: FC(F)(F)c1[nH]nnc1-c1ccnc(-c2cn(C[C@@H]3CCCc4cccc(C5CC5)c43)cn2)c1]

TABLE 2-continued
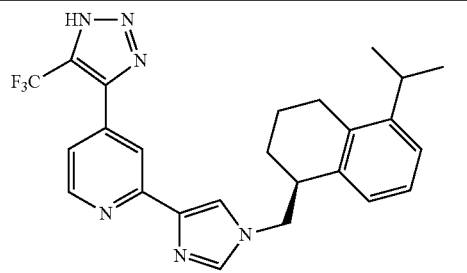
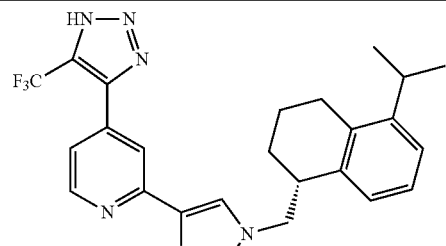
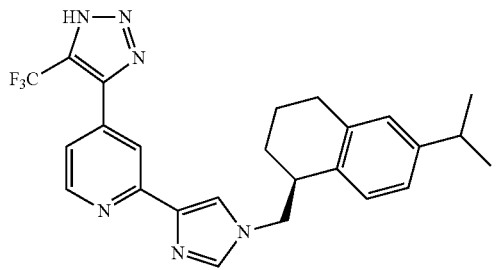 [SMILES: CC(C)c1ccc2c(c1)CCC[C@@H]2Cn1cnc(-c2cc(-c3nn[nH]c3C(F)(F)F)ccn2)c1]
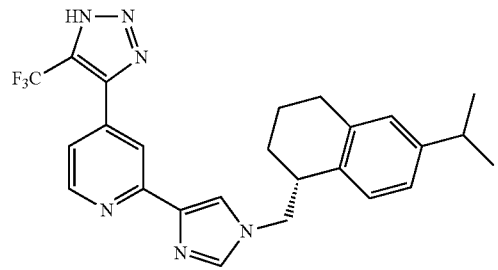 [SMILES: CC(C)c1ccc2c(c1)CCC[C@H]2Cn1cnc(-c2cc(-c3nn[nH]c3C(F)(F)F)ccn2)c1]
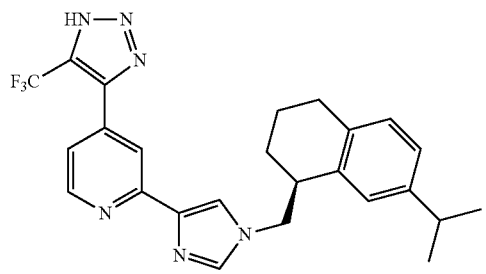 [SMILES: CC(C)c1ccc2c(c1)[C@@H](Cn1cnc(-c3cc(-c4nn[nH]c4C(F)(F)F)ccn3)c1)CCC2]
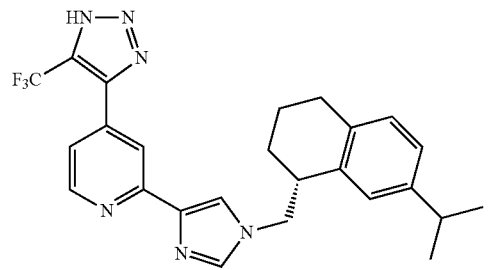
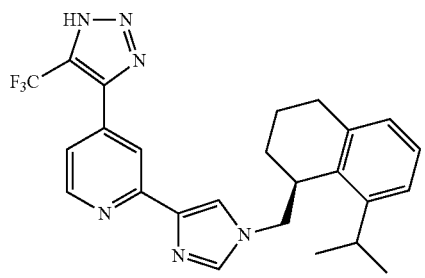 [SMILES: CC(C)c1cccc2c1[C@@H](Cn1cnc(-c3cc(-c4nn[nH]c4C(F)(F)F)ccn3)c1)CCC2]
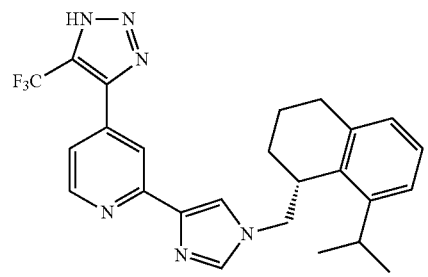 [SMILES: CC(C)c1cccc2c1[C@H](Cn1cnc(-c3cc(-c4nn[nH]c4C(F)(F)F)ccn3)c1)CCC2]
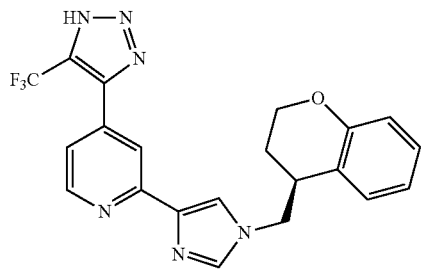 [SMILES: FC(F)(F)c1[nH]nnc1-c1ccnc(-c2cn(C[C@H]3CCOc4ccccc43)cn2)c1]
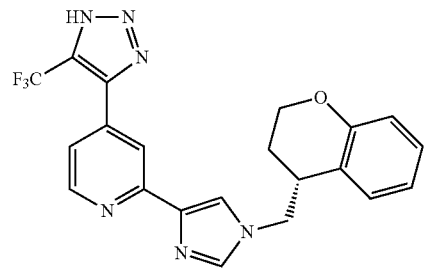
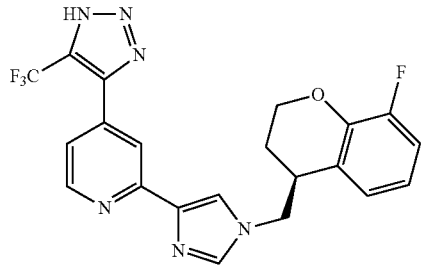 [SMILES: Fc1cccc2c1OCC[C@@H]2Cn1cnc(-c2cc(-c3nn[nH]c3C(F)(F)F)ccn2)c1]
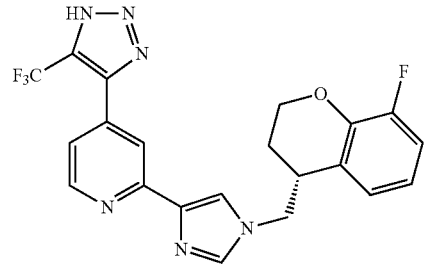 [SMILES: Fc1cccc2c1OCC[C@H]2Cn1cnc(-c2cc(-c3nn[nH]c3C(F)(F)F)ccn2)c1]

TABLE 2-continued
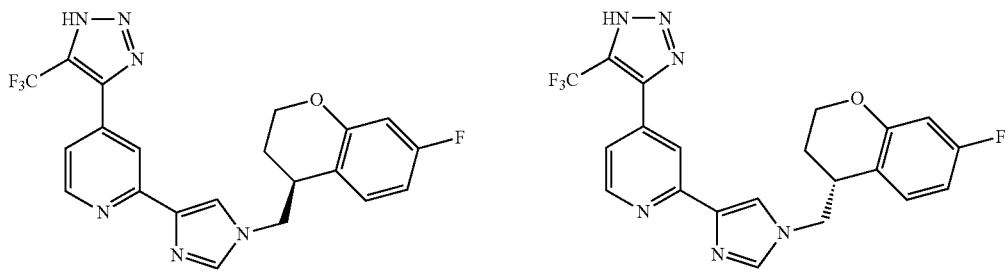
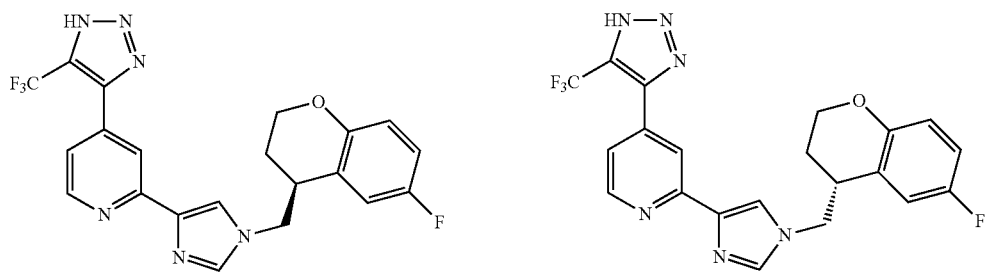
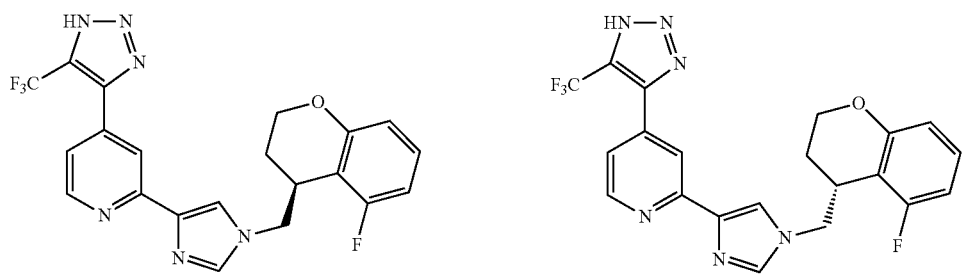
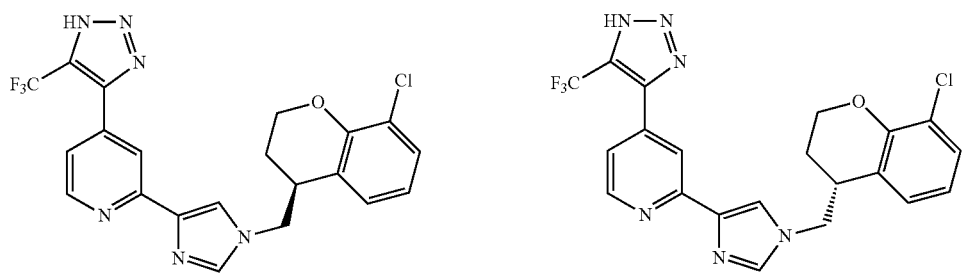
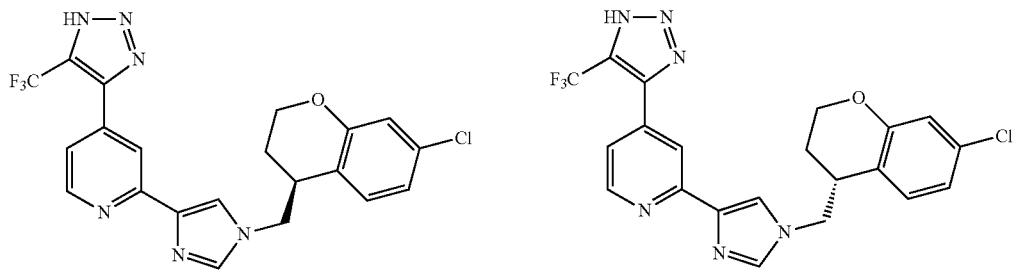

TABLE 2-continued
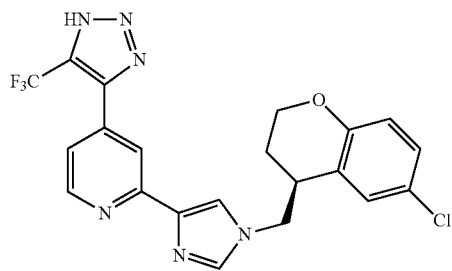 [SMILES: FC(F)(F)c1[nH]nnc1-c1ccnc(-c2cn(C[C@H]3CCOc4ccc(Cl)cc43)cn2)c1]
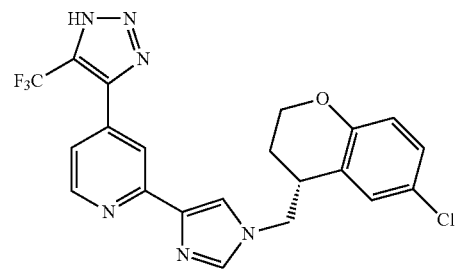 [SMILES: FC(F)(F)c1[nH]nnc1-c1ccnc(-c2cn(C[C@@H]3CCOc4ccc(Cl)cc43)cn2)c1]
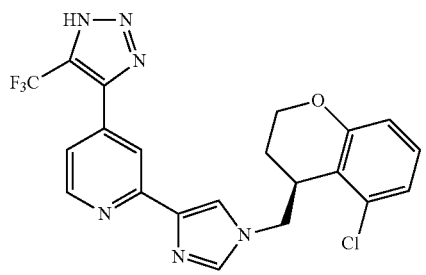 [SMILES: FC(F)(F)c1[nH]nnc1-c1ccnc(-c2cn(C[C@H]3CCOc4cccc(Cl)c43)cn2)c1]
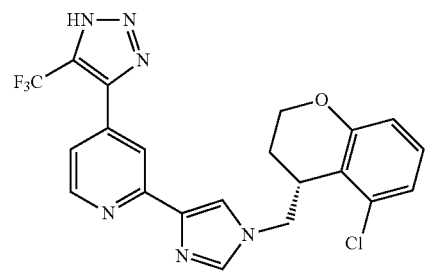 [SMILES: FC(F)(F)c1[nH]nnc1-c1ccnc(-c2cn(C[C@@H]3CCOc4cccc(Cl)c43)cn2)c1]
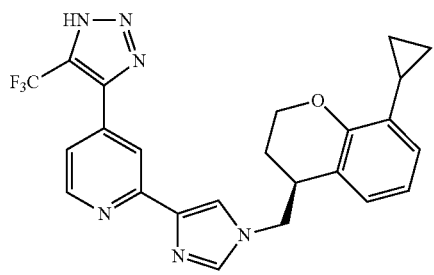 [SMILES: FC(F)(F)c1[nH]nnc1-c1ccnc(-c2cn(C[C@H]3CCOc4c(C5CC5)cccc43)cn2)c1]
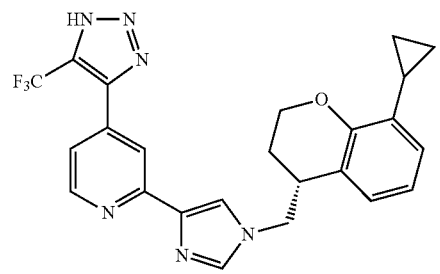 [SMILES: FC(F)(F)c1[nH]nnc1-c1ccnc(-c2cn(C[C@@H]3CCOc4c(C5CC5)cccc43)cn2)c1]
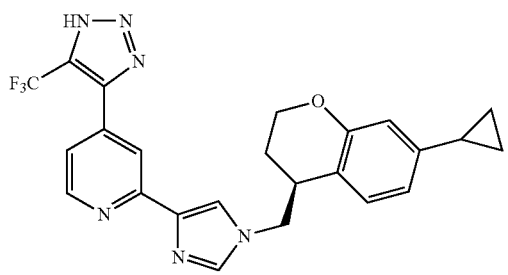 [SMILES: FC(F)(F)c1[nH]nnc1-c1ccnc(-c2cn(C[C@H]3CCOc4cc(C5CC5)ccc43)cn2)c1]
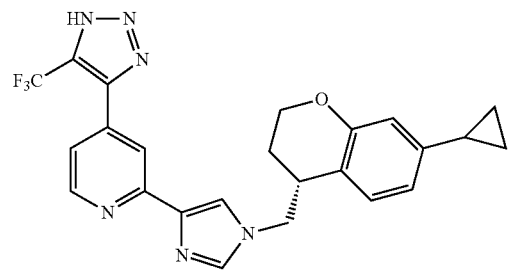
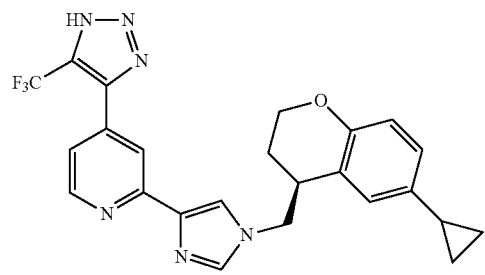 [SMILES: FC(F)(F)c1[nH]nnc1-c1ccnc(-c2cn(C[C@H]3CCOc4ccc(C5CC5)cc43)cn2)c1]
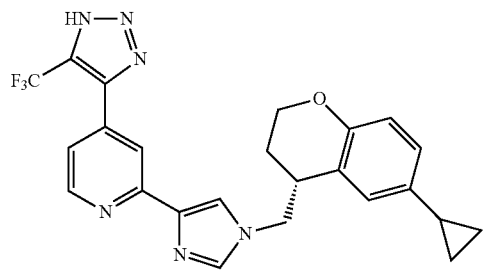 [SMILES: FC(F)(F)c1[nH]nnc1-c1ccnc(-c2cn(C[C@@H]3CCOc4ccc(C5CC5)cc43)cn2)c1]

TABLE 2-continued
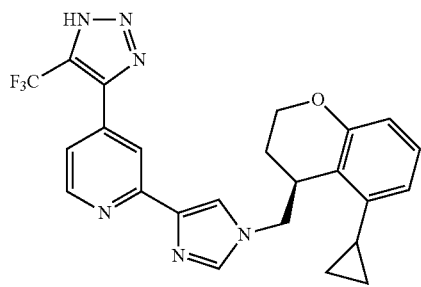 [SMILES: FC(F)(F)c1[nH]nnc1-c1ccnc(-c2cn(C[C@@H]3CCOc4cccc(C5CC5)c43)cn2)c1]
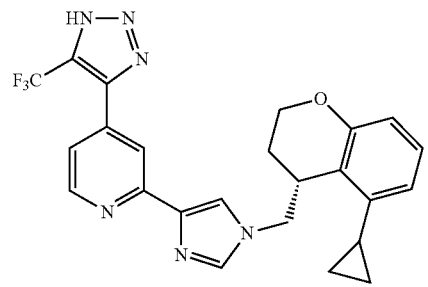
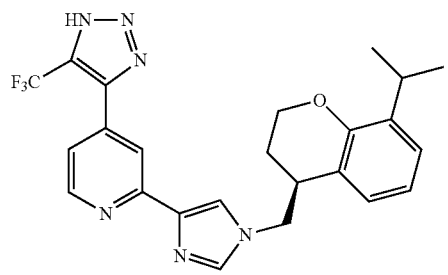 [SMILES: CC(C)c1cccc2c1OCC[C@@H]2Cn1cnc(-c2cc(-c3nn[nH]c3C(F)(F)F)ccn2)c1]
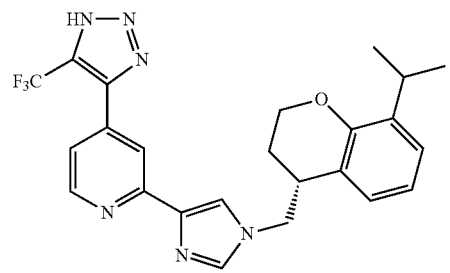 [SMILES: CC(C)c1cccc2c1OCC[C@H]2Cn1cnc(-c2cc(-c3nn[nH]c3C(F)(F)F)ccn2)c1]
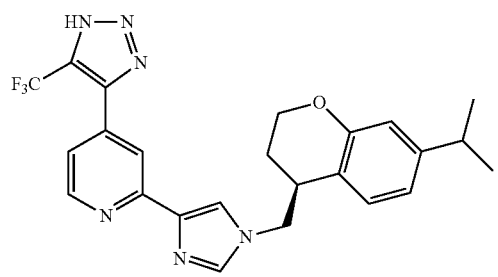 [SMILES: CC(C)c1ccc2c(c1)OCC[C@@H]2Cn1cnc(-c2cc(-c3nn[nH]c3C(F)(F)F)ccn2)c1]
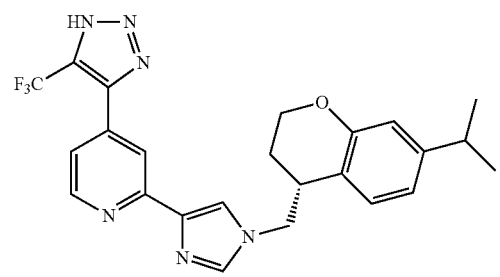 [SMILES: CC(C)c1ccc2c(c1)OCC[C@H]2Cn1cnc(-c2cc(-c3nn[nH]c3C(F)(F)F)ccn2)c1]
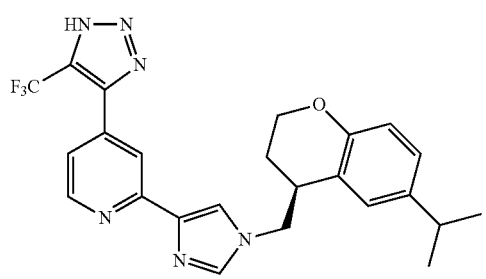 [SMILES: CC(C)c1ccc2c(c1)[C@@H](Cn1cnc(-c3cc(-c4nn[nH]c4C(F)(F)F)ccn3)c1)CCO2]
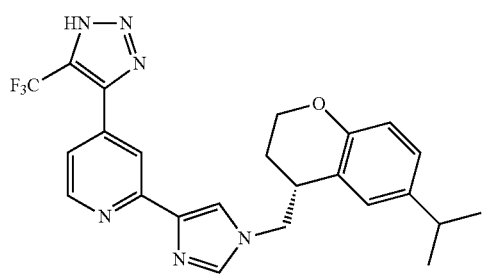 [SMILES: CC(C)c1ccc2c(c1)[C@H](Cn1cnc(-c3cc(-c4nn[nH]c4C(F)(F)F)ccn3)c1)CCO2]
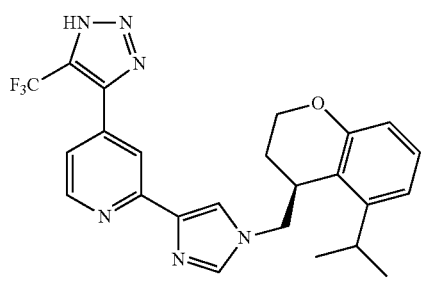 [SMILES: CC(C)c1cccc2c1[C@@H](Cn1cnc(-c3cc(-c4nn[nH]c4C(F)(F)F)ccn3)c1)CCO2]
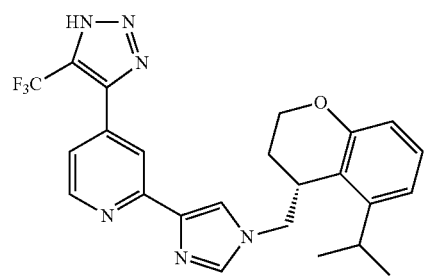 [SMILES: CC(C)c1cccc2c1[C@H](Cn1cnc(-c3cc(-c4nn[nH]c4C(F)(F)F)ccn3)c1)CCO2]

TABLE 2-continued
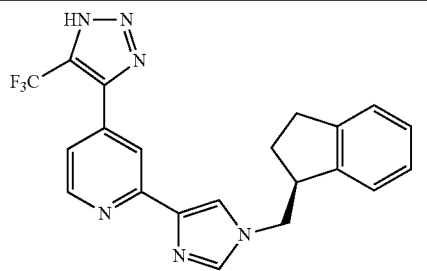
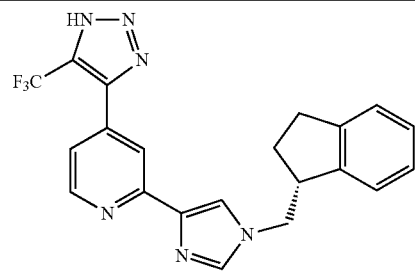
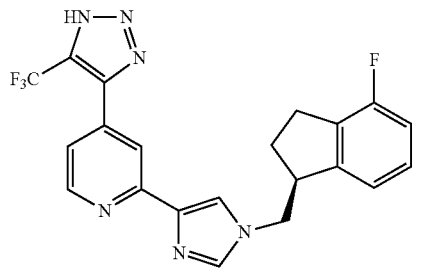 [SMILES: Fc1cccc2c1CC[C@@H]2Cn1cnc(-c2cc(-c3nn[nH]c3C(F)(F)F)ccn2)c1]
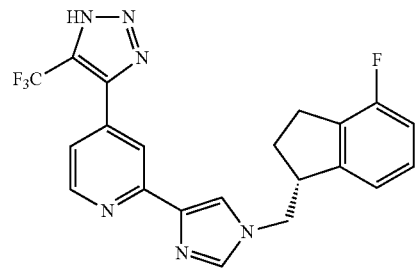 [SMILES: Fc1cccc2c1CC[C@H]2Cn1cnc(-c2cc(-c3nn[nH]c3C(F)(F)F)ccn2)c1]
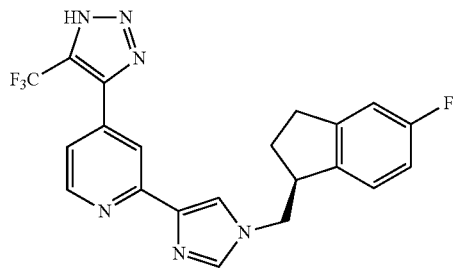 [SMILES: Fc1ccc2c(c1)CC[C@@H]2Cn1cnc(-c2cc(-c3nn[nH]c3C(F)(F)F)ccn2)c1]
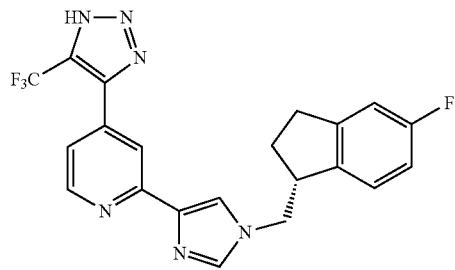 [SMILES: Fc1ccc2c(c1)CC[C@H]2Cn1cnc(-c2cc(-c3nn[nH]c3C(F)(F)F)ccn2)c1]
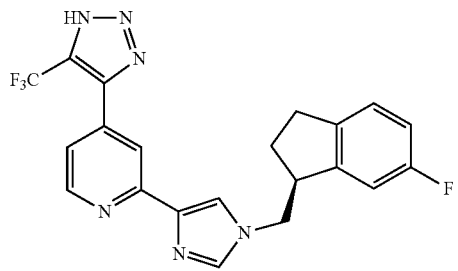 [SMILES: Fc1ccc2c(c1)[C@@H](Cn1cnc(-c3cc(-c4nn[nH]c4C(F)(F)F)ccn3)c1)CC2]
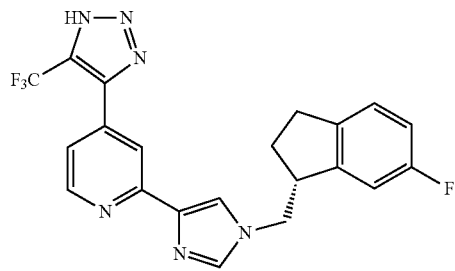
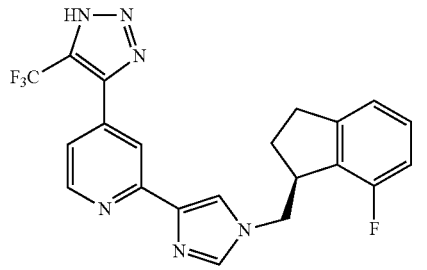 [SMILES: Fc1cccc2c1[C@@H](Cn1cnc(-c3cc(-c4nn[nH]c4C(F)(F)F)ccn3)c1)CC2]
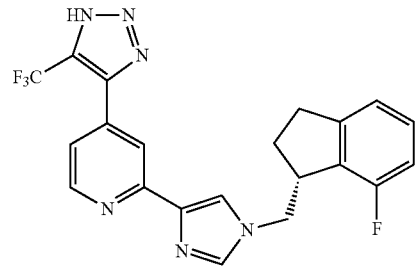
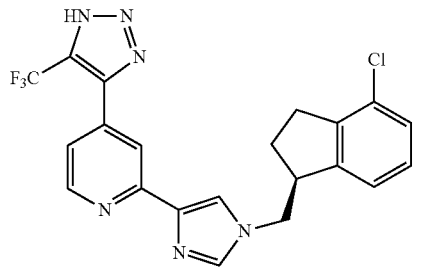 [SMILES: FC(F)(F)c1[nH]nnc1-c1ccnc(-c2cn(C[C@H]3CCc4c(Cl)cccc43)cn2)c1]
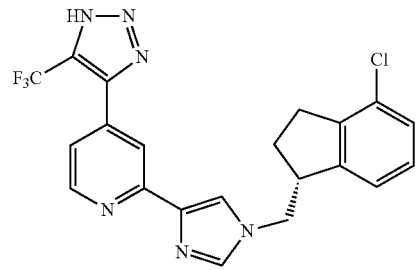

TABLE 2-continued
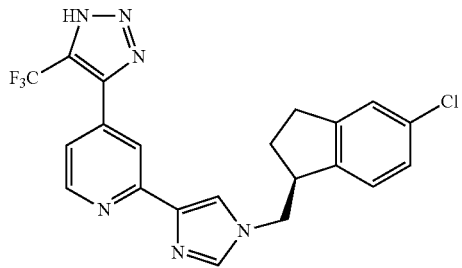 [SMILES: FC(F)(F)c1[nH]nnc1-c1ccnc(-c2cn(C[C@H]3CCc4cc(Cl)ccc43)cn2)c1]
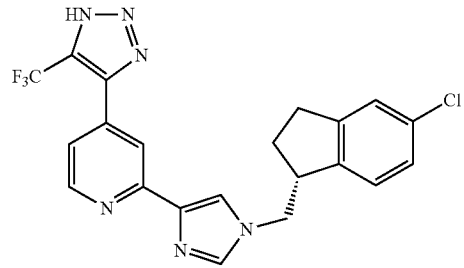 [SMILES: FC(F)(F)c1[nH]nnc1-c1ccnc(-c2cn(C[C@@H]3CCc4cc(Cl)ccc43)cn2)c1]
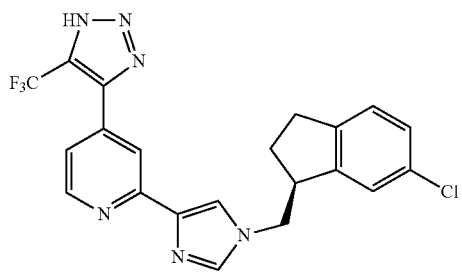 [SMILES: FC(F)(F)c1[nH]nnc1-c1ccnc(-c2cn(C[C@H]3CCc4ccc(Cl)cc43)cn2)c1]
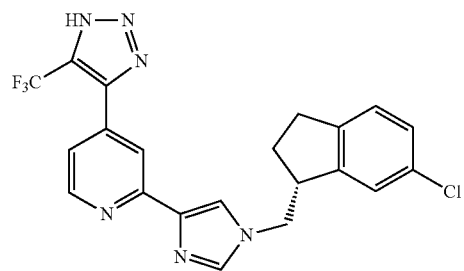
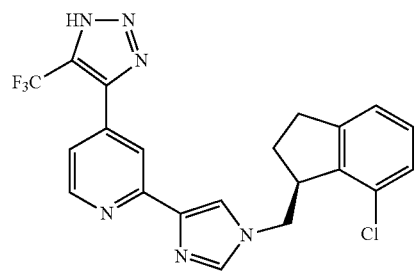 [SMILES: FC(F)(F)c1[nH]nnc1-c1ccnc(-c2cn(C[C@H]3CCc4cccc(Cl)c43)cn2)c1]
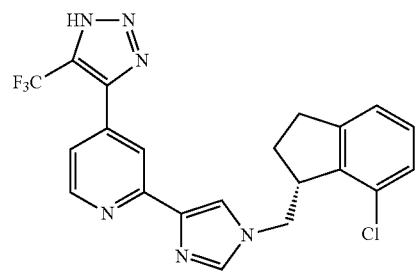 [SMILES: FC(F)(F)c1[nH]nnc1-c1ccnc(-c2cn(C[C@@H]3CCc4cccc(Cl)c43)cn2)c1]
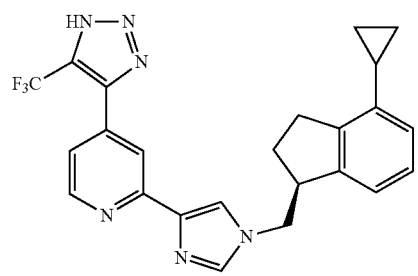 [SMILES: FC(F)(F)c1[nH]nnc1-c1ccnc(-c2cn(C[C@H]3CCc4c(C5CC5)cccc43)cn2)c1]
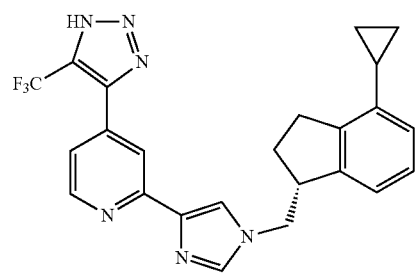 [SMILES: FC(F)(F)c1[nH]nnc1-c1ccnc(-c2cn(C[C@@H]3CCc4c(C5CC5)cccc43)cn2)c1]
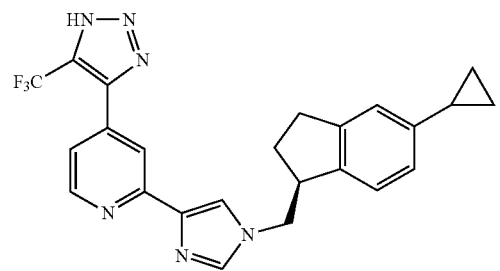 [SMILES: FC(F)(F)c1[nH]nnc1-c1ccnc(-c2cn(C[C@H]3CCc4cc(C5CC5)ccc43)cn2)c1]
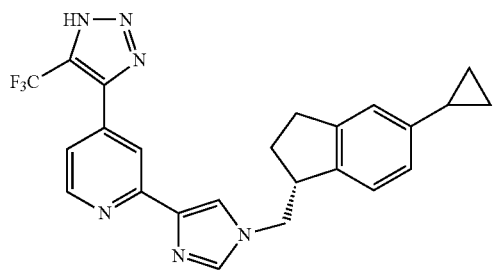 [SMILES: FC(F)(F)c1[nH]nnc1-c1ccnc(-c2cn(C[C@@H]3CCc4cc(C5CC5)ccc43)cn2)c1]

TABLE 2-continued
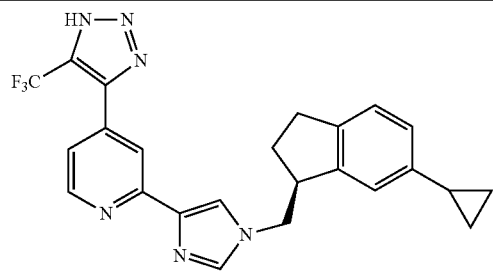
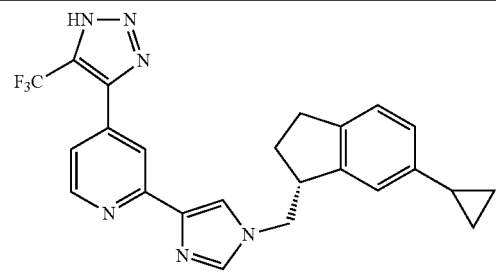
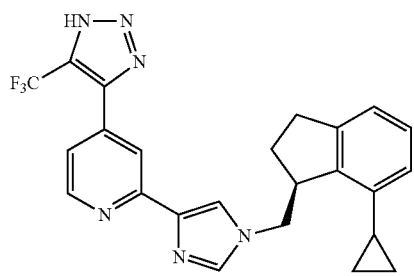 [SMILES: FC(F)(F)c1[nH]nnc1-c1ccnc(-c2cn(C[C@H]3CCc4cccc(C5CC5)c43)cn2)c1]
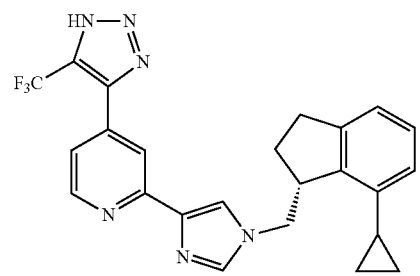 [SMILES: FC(F)(F)c1[nH]nnc1-c1ccnc(-c2cn(C[C@@H]3CCc4cccc(C5CC5)c43)cn2)c1]
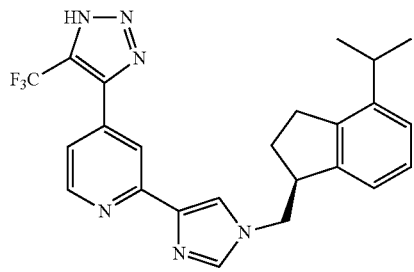 [SMILES: CC(C)c1cccc2c1CC[C@@H]2Cn1cnc(-c2cc(-c3nn[nH]c3C(F)(F)F)ccn2)c1]
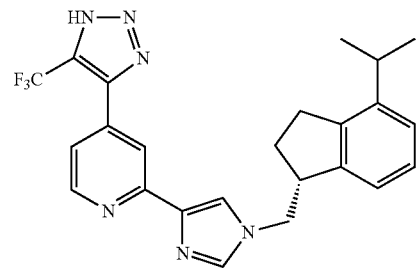 [SMILES: CC(C)c1cccc2c1CC[C@H]2Cn1cnc(-c2cc(-c3nn[nH]c3C(F)(F)F)ccn2)c1]
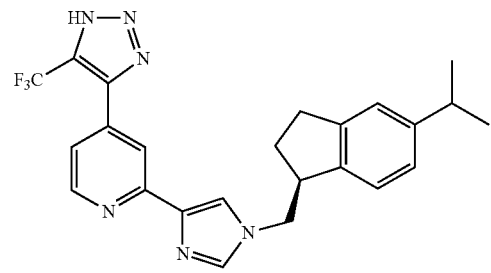
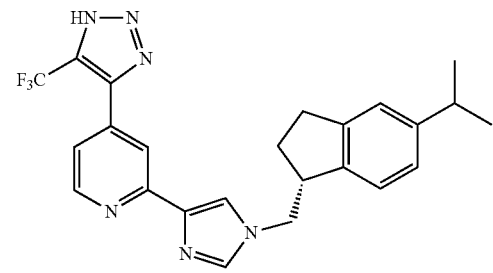 [SMILES: CC(C)c1ccc2c(c1)CC[C@H]2Cn1cnc(-c2cc(-c3nn[nH]c3C(F)(F)F)ccn2)c1]
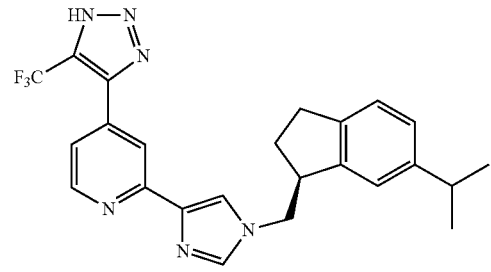 [SMILES: CC(C)c1ccc2c(c1)[C@@H](Cn1cnc(-c3cc(-c4nn[nH]c4C(F)(F)F)ccn3)c1)CC2]
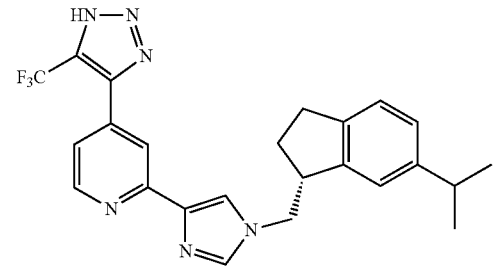 [SMILES: CC(C)c1ccc2c(c1)[C@H](Cn1cnc(-c3cc(-c4nn[nH]c4C(F)(F)F)ccn3)c1)CC2]
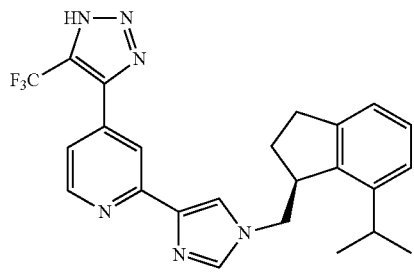 [SMILES: CC(C)c1cccc2c1[C@@H](Cn1cnc(-c3cc(-c4nn[nH]c4C(F)(F)F)ccn3)c1)CC2]
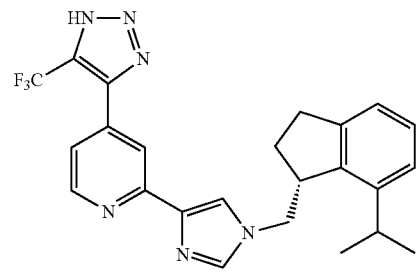 [SMILES: CC(C)c1cccc2c1[C@H](Cn1cnc(-c3cc(-c4nn[nH]c4C(F)(F)F)ccn3)c1)CC2]

TABLE 2-continued
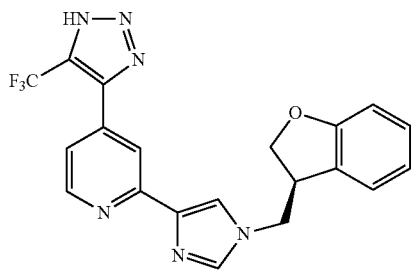 [SMILES: FC(F)(F)c1[nH]nnc1-c1ccnc(-c2cn(C[C@H]3COc4ccccc43)cn2)c1] 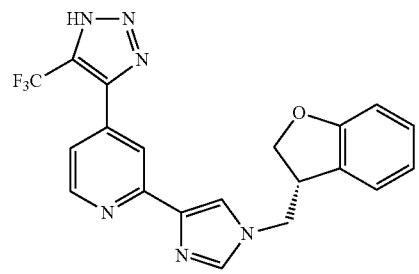 [SMILES: FC(F)(F)c1[nH]nnc1-c1ccnc(-c2cn(C[C@@H]3COc4ccccc43)cn2)c1]
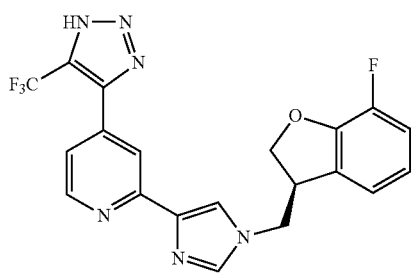 [SMILES: Fc1cccc2c1OC[C@@H]2Cn1cnc(-c2cc(-c3nn[nH]c3C(F)(F)F)ccn2)c1] 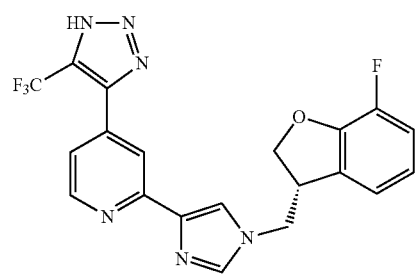 [SMILES: Fc1cccc2c1OC[C@H]2Cn1cnc(-c2cc(-c3nn[nH]c3C(F)(F)F)ccn2)c1]
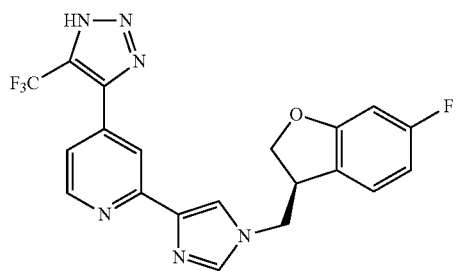 [SMILES: Fc1ccc2c(c1)OC[C@@H]2Cn1cnc(-c2cc(-c3nn[nH]c3C(F)(F)F)ccn2)c1] 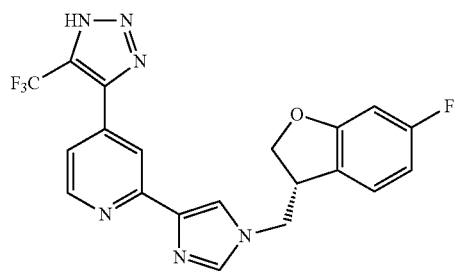 [SMILES: Fc1ccc2c(c1)OC[C@H]2Cn1cnc(-c2cc(-c3nn[nH]c3C(F)(F)F)ccn2)c1]
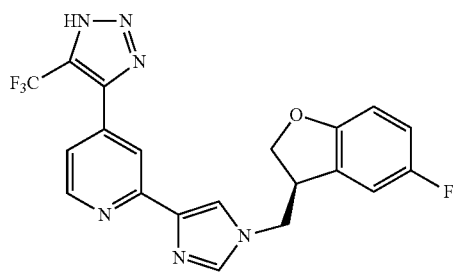 [SMILES: Fc1ccc2c(c1)[C@@H](Cn1cnc(-c3cc(-c4nn[nH]c4C(F)(F)F)ccn3)c1)CO2] 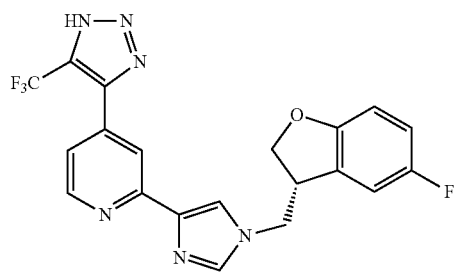 [SMILES: Fc1ccc2c(c1)[C@H](Cn1cnc(-c3cc(-c4nn[nH]c4C(F)(F)F)ccn3)c1)CO2]
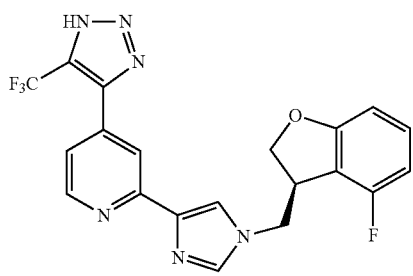 [SMILES: Fc1cccc2c1[C@@H](Cn1cnc(-c3cc(-c4nn[nH]c4C(F)(F)F)ccn3)c1)CO2] 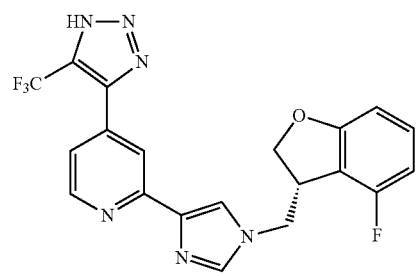 [SMILES: Fc1cccc2c1[C@H](Cn1cnc(-c3cc(-c4nn[nH]c4C(F)(F)F)ccn3)c1)CO2]

TABLE 2-continued
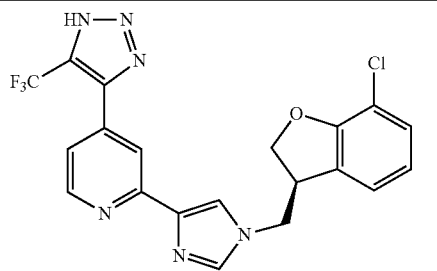
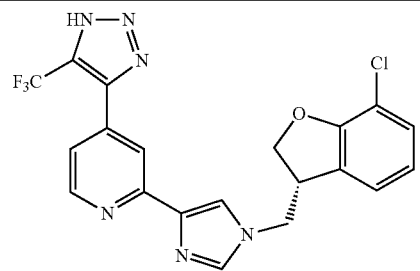
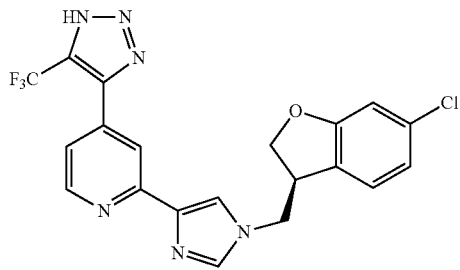 [SMILES: FC(F)(F)c1[nH]nnc1-c1ccnc(-c2cn(C[C@H]3COc4cc(Cl)ccc43)cn2)c1]
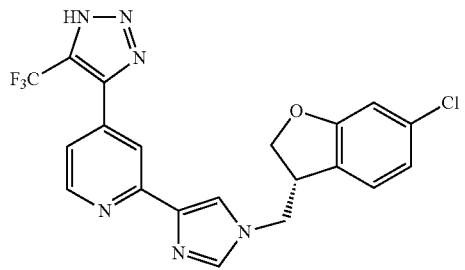 [SMILES: FC(F)(F)c1[nH]nnc1-c1ccnc(-c2cn(C[C@@H]3COc4cc(Cl)ccc43)cn2)c1]
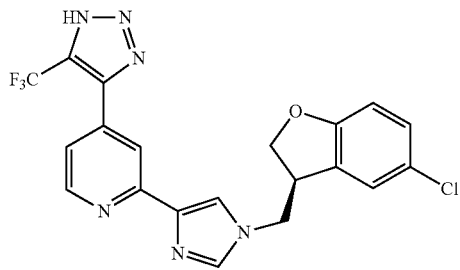 [SMILES: FC(F)(F)c1[nH]nnc1-c1ccnc(-c2cn(C[C@H]3COc4ccc(Cl)cc43)cn2)c1]
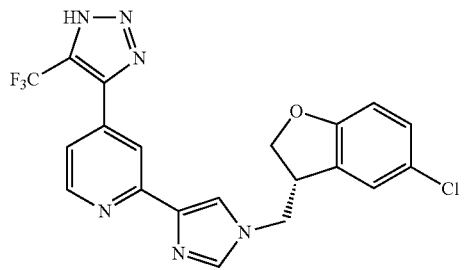 [SMILES: FC(F)(F)c1[nH]nnc1-c1ccnc(-c2cn(C[C@@H]3COc4ccc(Cl)cc43)cn2)c1]
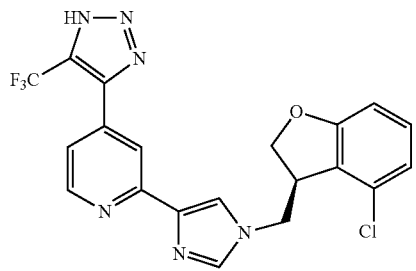 [SMILES: FC(F)(F)c1[nH]nnc1-c1ccnc(-c2cn(C[C@H]3COc4cccc(Cl)c43)cn2)c1]
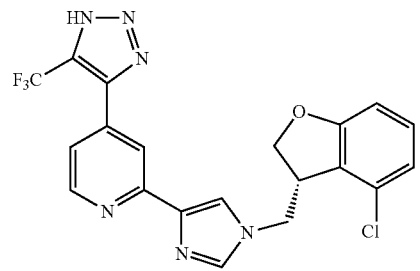 [SMILES: FC(F)(F)c1[nH]nnc1-c1ccnc(-c2cn(C[C@@H]3COc4cccc(Cl)c43)cn2)c1]
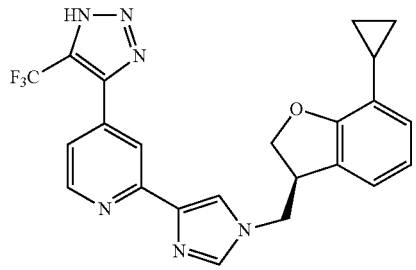 [SMILES: FC(F)(F)c1[nH]nnc1-c1ccnc(-c2cn(C[C@H]3COc4c(C5CC5)cccc43)cn2)c1]
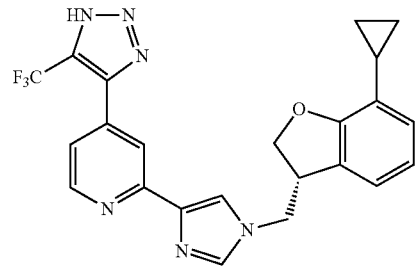 [SMILES: FC(F)(F)c1[nH]nnc1-c1ccnc(-c2cn(C[C@@H]3COc4c(C5CC5)cccc43)cn2)c1]
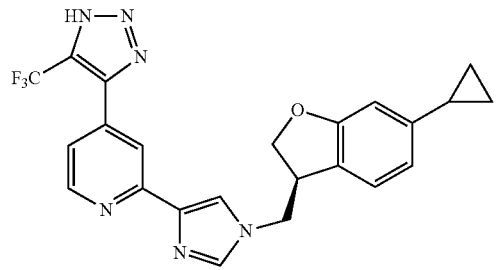 [SMILES: FC(F)(F)c1[nH]nnc1-c1ccnc(-c2cn(C[C@H]3COc4cc(C5CC5)ccc43)cn2)c1]
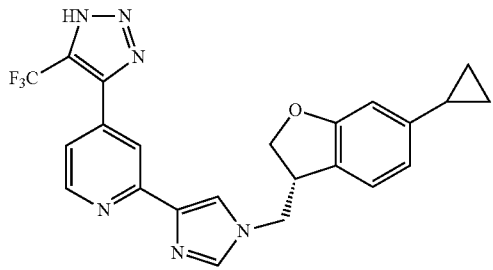 [SMILES: FC(F)(F)c1[nH]nnc1-c1ccnc(-c2cn(C[C@@H]3COc4cc(C5CC5)ccc43)cn2)c1]

TABLE 2-continued
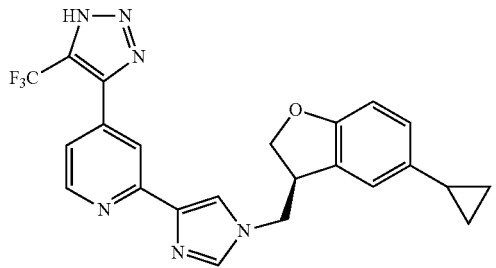 [SMILES: FC(F)(F)c1[nH]nnc1-c1ccnc(-c2cn(C[C@H]3COc4ccc(C5CC5)cc43)cn2)c1]
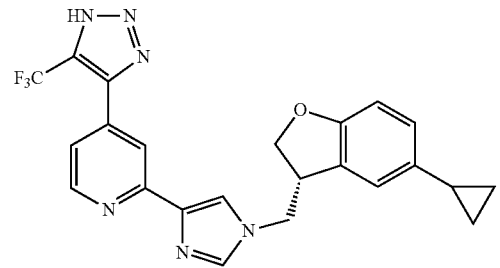 [SMILES: FC(F)(F)c1[nH]nnc1-c1ccnc(-c2cn(C[C@@H]3COc4ccc(C5CC5)cc43)cn2)c1]
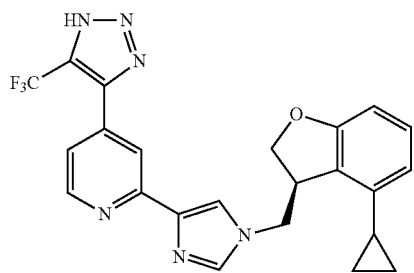 [SMILES: FC(F)(F)c1[nH]nnc1-c1ccnc(-c2cn(C[C@H]3COc4cccc(C5CC5)c43)cn2)c1]
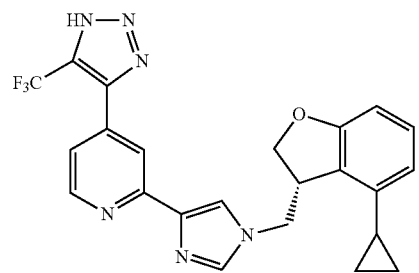 [SMILES: FC(F)(F)c1[nH]nnc1-c1ccnc(-c2cn(C[C@@H]3COc4cccc(C5CC5)c43)cn2)c1]
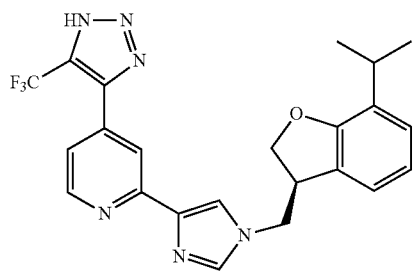 [SMILES: CC(C)c1cccc2c1OC[C@@H]2Cn1cnc(-c2cc(-c3nn[nH]c3C(F)(F)F)ccn2)c1]
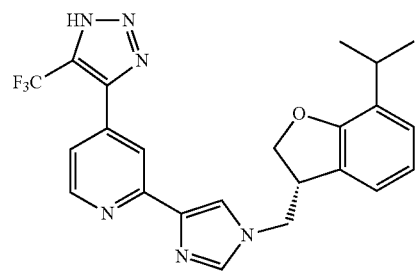 [SMILES: CC(C)c1cccc2c1OC[C@H]2Cn1cnc(-c2cc(-c3nn[nH]c3C(F)(F)F)ccn2)c1]
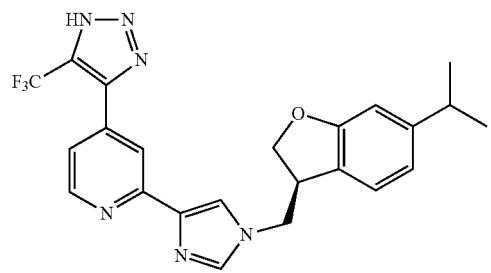 [SMILES: CC(C)c1ccc2c(c1)OC[C@@H]2Cn1cnc(-c2cc(-c3nn[nH]c3C(F)(F)F)ccn2)c1]
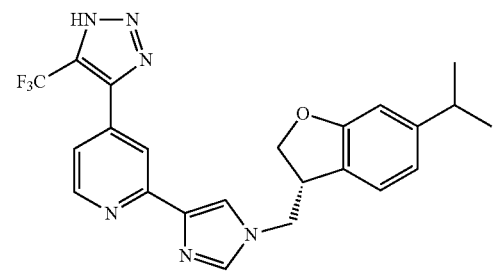 [SMILES: CC(C)c1ccc2c(c1)OC[C@H]2Cn1cnc(-c2cc(-c3nn[nH]c3C(F)(F)F)ccn2)c1]
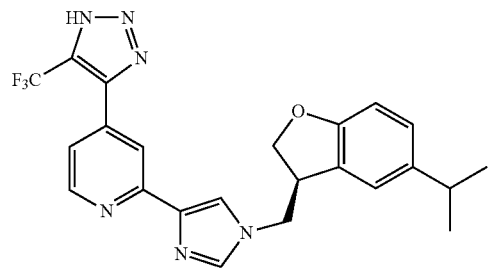 [SMILES: CC(C)c1ccc2c(c1)[C@@H](Cn1cnc(-c3cc(-c4nn[nH]c4C(F)(F)F)ccn3)c1)CO2]
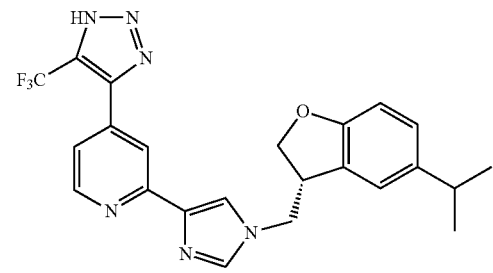 [SMILES: CC(C)c1ccc2c(c1)[C@H](Cn1cnc(-c3cc(-c4nn[nH]c4C(F)(F)F)ccn3)c1)CO2]

TABLE 2-continued
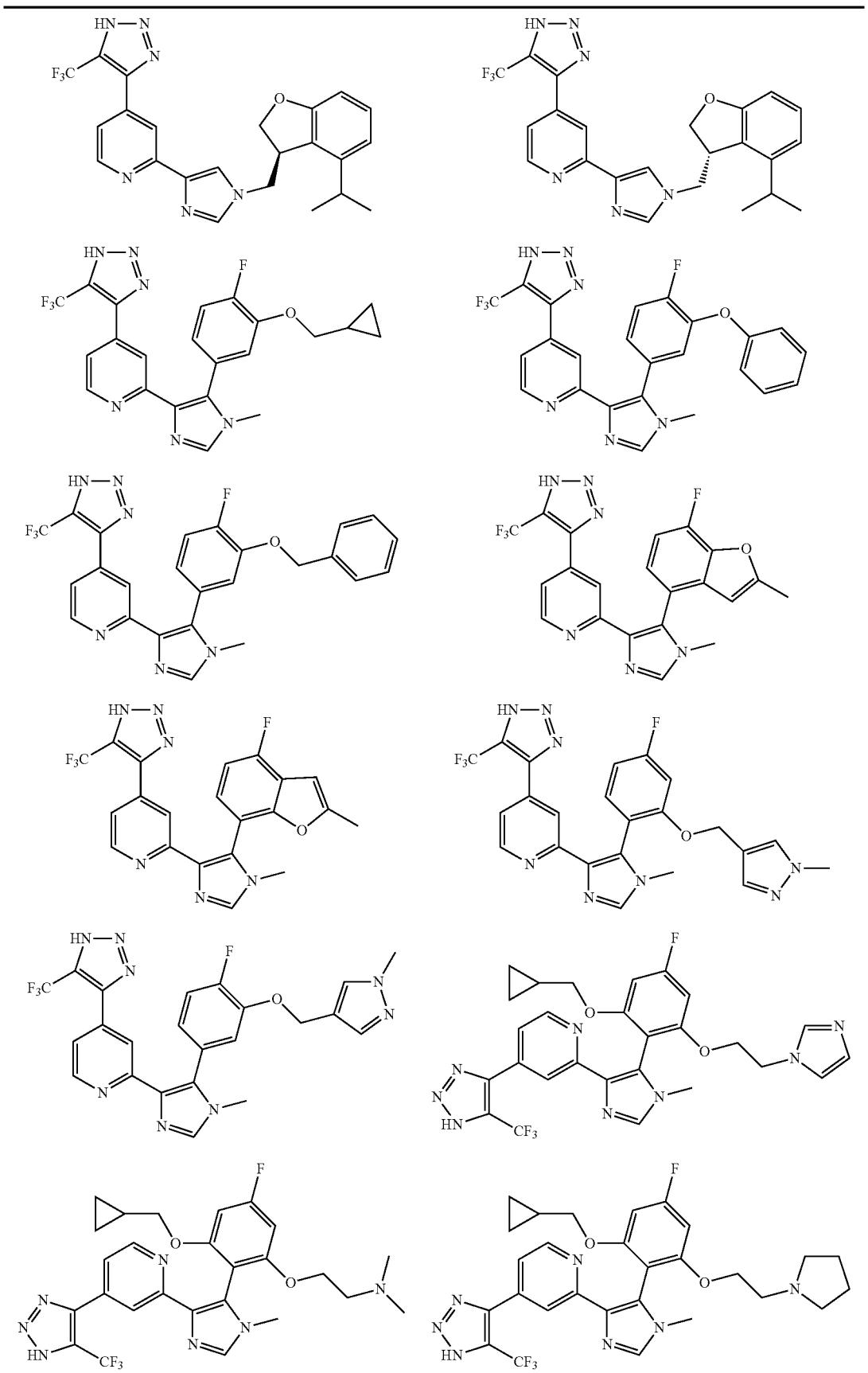

TABLE 2-continued
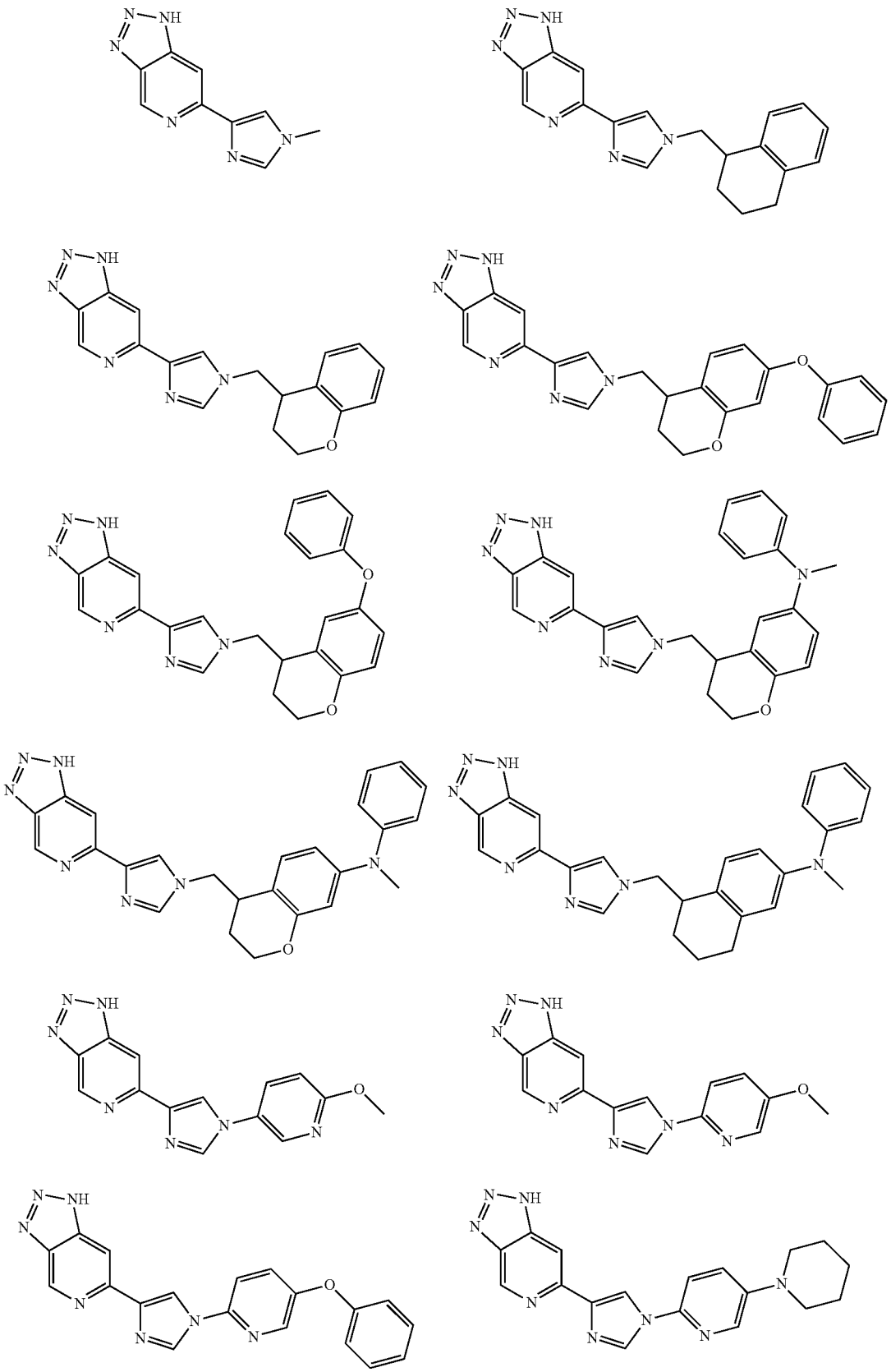

TABLE 2-continued

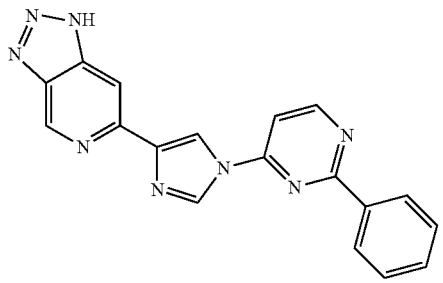 [SMILES: c1ccc(-c2nccc(-n3cnc(-c4cc5[nH]nnc5cn4)c3)n2)cc1]
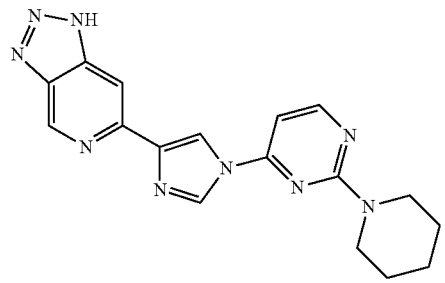 [SMILES: c1cc(-n2cnc(-c3cc4[nH]nnc4cn3)c2)nc(N2CCCCC2)n1]

Preparation of the Substituted Imidazole-Pyridine Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted imidazole-pyridine derivative compounds described herein is P. H. Stahl & C. G. Wermuth "Handbook of Pharmaceutical Salts", Verlag Helvetica Chimica Acta, Zurich, 2002.

The substituted 4-triazolylpyridine derivative compounds are prepared by the general synthetic route described below in Scheme 1-4.

Scheme 1

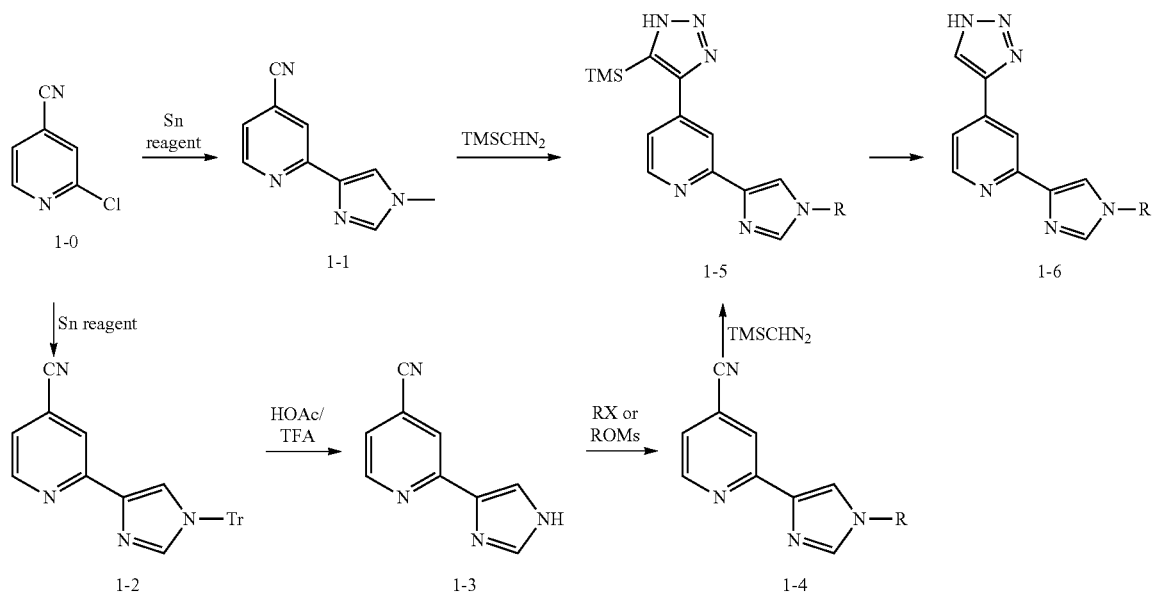

Referring to Scheme 1, 2-chloro-4-pyridinenitrile (1-0) undergoes Stille coupling with tin reagent, N-methyl-4-(tributylstannyl)imidazole or trityl protected tributyltin imidazole, in presence of a catalyst, such as tetrakis(triphenylphosphine) palladium (0), under heating condition, i.e. 130° C., to give the coupling products 1-1 and 1-2. Deprotection of the trityl protective group is performed using acids, such as acetic acid and TFA, at room temperature to give compound 1-3, which is then alkylated with halogenated alkyl derivative or mesylated derivative to give 1-4. Reaction of the nitrile intermediates 1-1 and 1-4 with TMS diazomethane, in presence of n-butyllithium, in an anhydrous organic solvent, such as THF, provides TMS protected 4-triazolopyridine intermediate 1-5, which undergoes deprotection using a base, such as NaOH, in an organic solvent, such as MeOH, under heating condition (i.e. 50° C.) to give the final product, compound 1-6.

Scheme 2

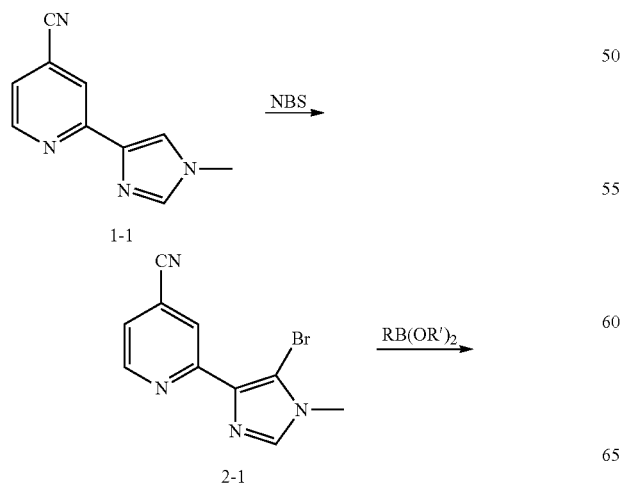

-continued

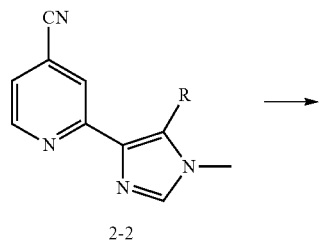

2-2

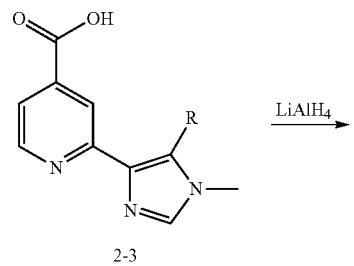

2-3

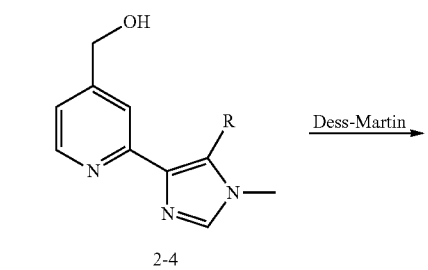

2-4

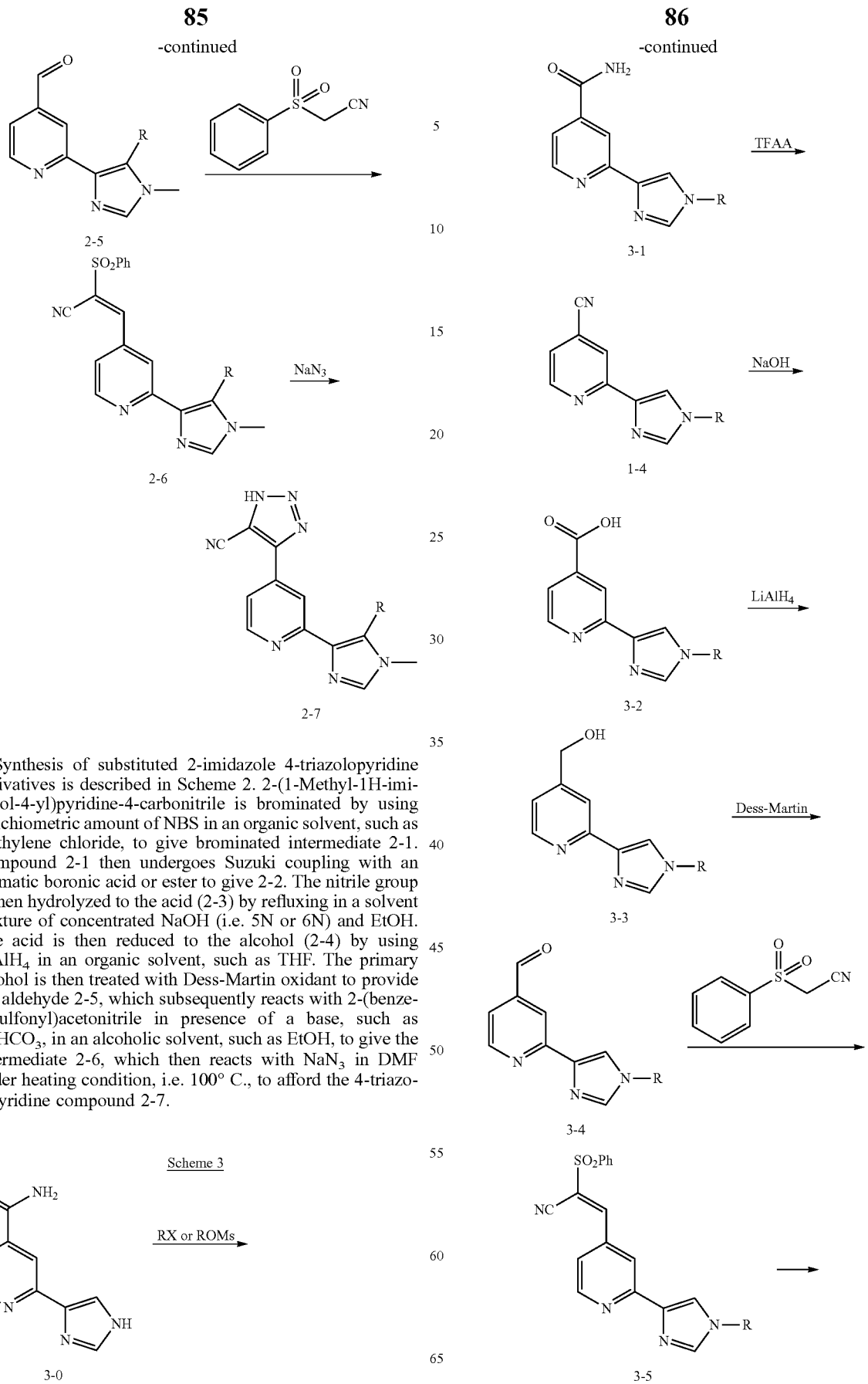

Synthesis of substituted 2-imidazole 4-triazolopyridine derivatives is described in Scheme 2. 2-(1-Methyl-1H-imidazol-4-yl)pyridine-4-carbonitrile is brominated by using stoichiometric amount of NBS in an organic solvent, such as methylene chloride, to give brominated intermediate 2-1. Compound 2-1 then undergoes Suzuki coupling with an aromatic boronic acid or ester to give 2-2. The nitrile group is then hydrolyzed to the acid (2-3) by refluxing in a solvent mixture of concentrated NaOH (i.e. 5N or 6N) and EtOH. The acid is then reduced to the alcohol (2-4) by using LiAlH$_4$ in an organic solvent, such as THF. The primary alcohol is then treated with Dess-Martin oxidant to provide the aldehyde 2-5, which subsequently reacts with 2-(benzenesulfonyl)acetonitrile in presence of a base, such as NaHCO$_3$, in an alcoholic solvent, such as EtOH, to give the intermediate 2-6, which then reacts with NaN$_3$ in DMF under heating condition, i.e. 100° C., to afford the 4-triazolopyridine compound 2-7.

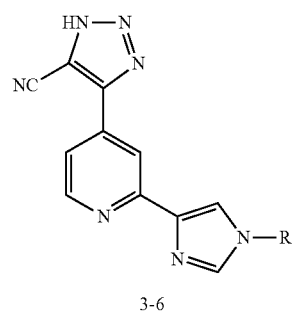

3-6

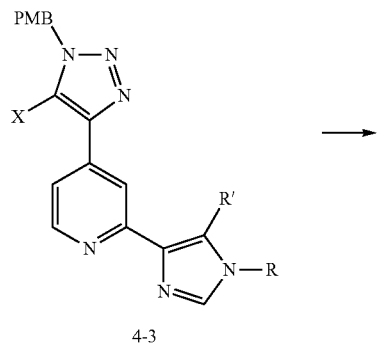

4-3

Referring to Scheme 3, similar to Scheme 1, intermediate 1-4 can also be synthesized from 4-amide-2-imidazole pyridine (3-0). Alkylation using either halogenated RX or mesylate ROMs gives 3-1, which can be converted to nitrile intermediate 1-4 using trifluoroacetic anhydride, in presence of excess of pyridine (i.e. 3 equiv.) in an organic solvent, such as methylene chloride. Final compounds 3-6 can then be obtained using similar procedures as described in Scheme 2.

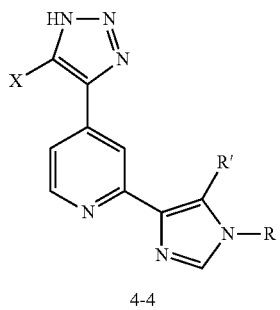

4-4

X = F, Cl, CF₃

Synthesis of substituted triazole analogs 4-4 is shown in Scheme 4. Starting from the aldehyde 3-7, (1-diazo-2-oxo-propyl)-phosphonic acid dimethyl ester is added to a mixture of the aldehyde and a base, such as potassium carbonate, in an alcoholic solvent, i.e. MeOH, to give the alkyne intermediate (4-1). It is then added to a mixture of PMB protected azide and KI in THF, in presence of a copper complex and a base, such as triethylamine, to give the iodo-triazole intermediate 4-2. Conversion of the iodo to various substitutions can be accomplished by treating 4-2 with KF, KCl or TMSCF₃ in a solvent mixture, such as CH₃CN and H₂O, and heated at elevated temp., i.e. 160° C., in a microwave oven, followed by deprotection of the PMB group using TFA under heating condition, i.e. 60° C., to give the final compounds 4-4.

In each of the above reaction procedures or schemes, the various substituents may be selected from among the various substituents otherwise taught herein.

The substituted azabenzotriazole derivative compounds are prepared by the general synthetic route described below in Scheme 5.

Scheme 4

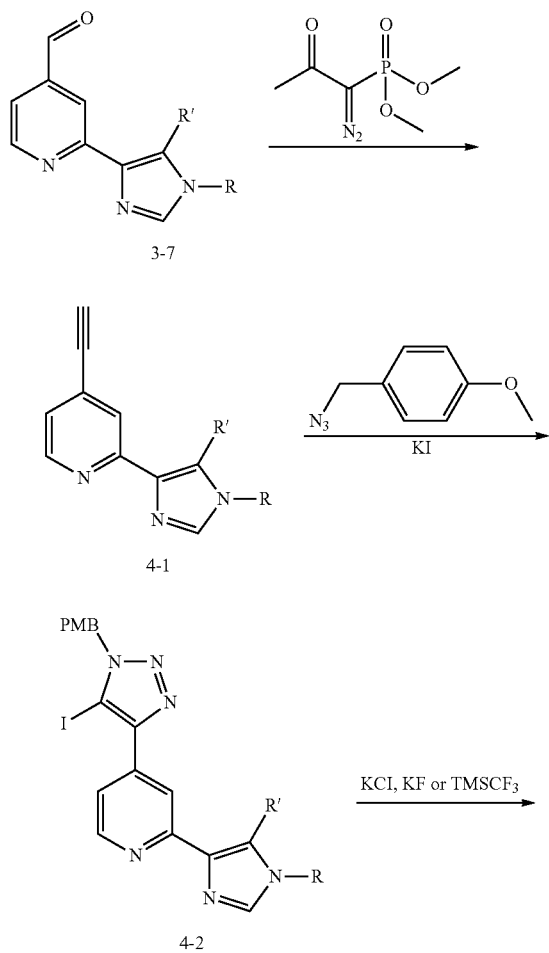

Scheme 5

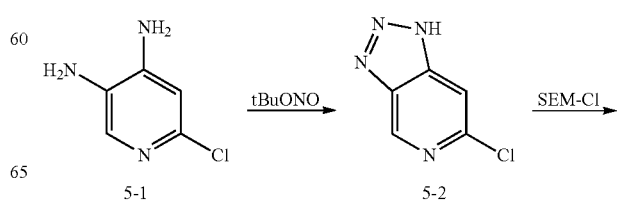

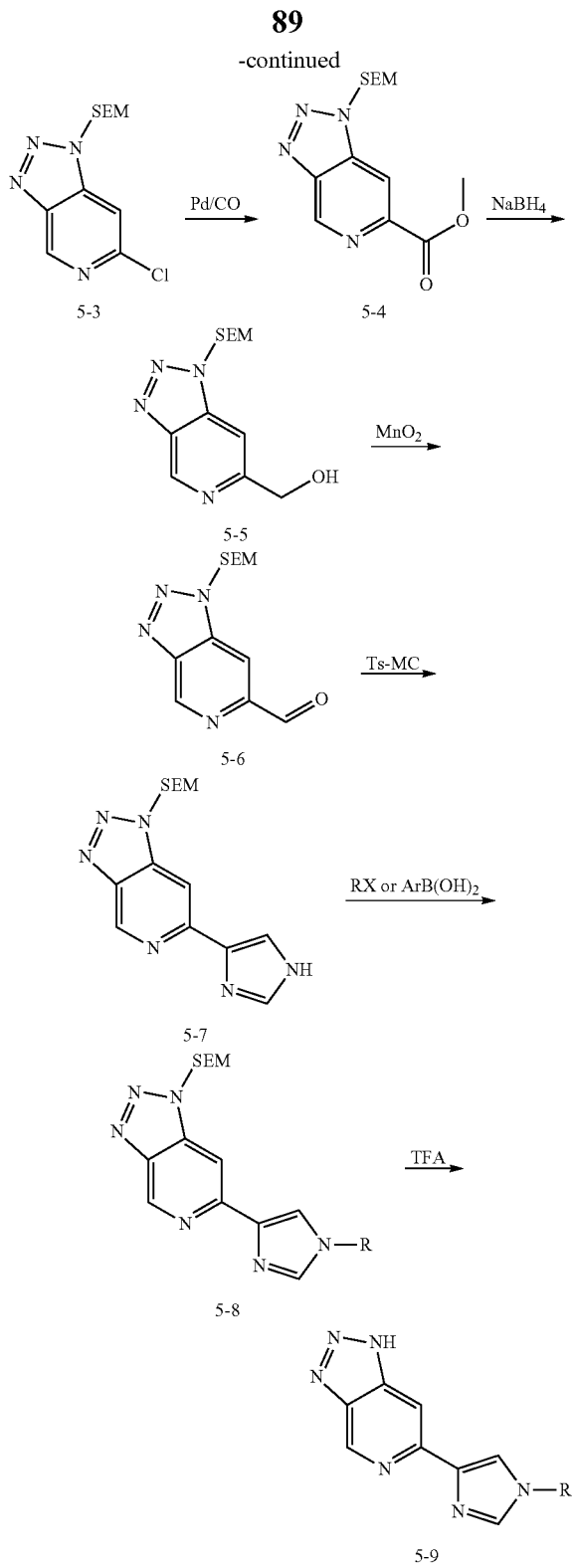

Referring to Scheme 5, treatment of diaminopyridine 5-1 with diazotization reagent afforded azabenzotriazole 5-2, which was subsequently protected with a SEM protecting group. Carbonylation of 5-3 in the presence of methanol and Palladium catalyst furnished 5-4 which was reduced to alcohol 5-5 and re-oxidized to corresponding aldehyde 5-6. Treatment with Ts-MIC reagent followed by ammonia workup furnished imidazole 5-7. Alkylation with alkylhalide under basic conditions or coupling with a boronic acid under Chan-Lam reaction conditions afforded 5-8. Removal of SEM protecting group under strongly acidic conditions furnished 5-9.

Pharmaceutical Compositions

In certain embodiments, the substituted imidazole-pyridine derivative compound as described herein is administered as a pure chemical. In other embodiments, the substituted imidazole-pyridine derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)), the disclosure of which is hereby incorporated herein by reference in its entirety.

Accordingly, provided herein is a pharmaceutical composition comprising at least one substituted imidazole-pyridine derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

One embodiment provides a pharmaceutical composition comprising a pharmaceutically acceptable carrier and a compound of Formula (II), or a pharmaceutically acceptable salt thereof.

In certain embodiments, the substituted imidazole-pyridine derivative compound as described by Formula (I) or (II) is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, Pa. (2005)).

The dose of the composition comprising at least one substituted imidazole-pyridine derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can covalently modify histones at various sites.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenosyl methionine (SAM) to histones. Histone methylation is known to participate in a diverse range of biological processes including heterochromatin formation, X-chromosome inactivation, and transcriptional regulation (Lachner et al., (2003) J. Cell Sci. 116:2117-2124; Margueron et al., (2005) Curr. Opin. Genet. Dev. 15:163-176).

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). However, generally, methylation on H3K9, H3K27 and H4K20 is linked to gene silencing, while methylation on H3K4, H3K36, and H3K79 is generally associated with active gene expression. In addition, tri- and di-methylation of H3K4 generally marks the transcriptional start sites of actively transcribed genes, whereas mono-methylation of H3K4 is associated with enhancer sequences.

A "demethylase" or "protein demethylase," as referred to herein, refers to an enzyme that removes at least one methyl group from an amino acid side chain. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demethylases were predicted, and confirmed when a H3K36 demethylase was found using a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

FBXL10 and FBXL11

F-box and leucine-rich repeat protein 10 (FBXL10) and F-box and leucine-rich repeat protein 11 (FBXL11) are multifunctional F-box family proteins that demethylate histone H3 through a hydroxylation based mechanism. FBXL10, also known as lysine (K)-specific demethylase 2B (KDM2B) or Jumonji C domain-containing histone demethylase 1B (JHDM1B), preferentially demethylates trimethylated K4 and dimethylated K36 of histone H3, but contains weak or no activity for mono- and tri-methylated H3K36. FBXL10 contains three domains, a catalytic JMJC domain, an F-box domain and a CXXC DNA-binding domain. The N-terminal JMJC domain coordinates iron and α-ketoglutarate to catalyze demethylation through the hydroxylation based mechanism. The CXXC DNA-binding domain allows FBXL10 to preferentially bind to transcribed region of the ribosomal RNA, leading to repression of the ribosomal RNA gene transcription and ultimately leading to inhibition of cell growth and proliferation. FBXL10 has been found to be overexpressed in acute myeloid leukemia, bladder carcinoma and pancreatic ductal adenocarcinoma. Recently, it has been demonstrated that FBXL10 regulates the expression of Polycomb target genes, those proteins are epigenetic regulators essential for stem cell differentiation. This regulation implicates FBXL10's involvement in tumorigenesis through the regulation of these Polycomb target genes.

FBXL11, also known as KDM2A or JHDM1A, demethylates mono- and di-methylated K36 of histone H3. The CXXC DNA-binding domain recognizes non-methylated DNA and targets CpG island regions where it specifically removes H3K36 methylation. Further, FBXL11 is required to maintain a heterochromatic state, sustain centromeric integrity and genomic stability during mitosis. In addition, FBXL11 is a key negative regulator of NF-KB. Overexpression of FBXL11 has been observed in non-small cell lung cancer (NSCLC) where FBXL11 upregulates phosphor-ERK1/2 by repressing DUSP3 expression in NSCLC cell lines. Negative regulation of gluconeogenic gene expression by FBXL11 results in suppression of two rate-limiting gluconeogenic enzymes, critical for maintaining blood glucose homeostasis.

In an additional embodiment is a method for inhibiting a histone-demethylase enzyme comprising contacting a histone demethylase enzyme with a compound of Formula (I) or (II).

In an additional embodiment is the method for inhibiting a histone-demethylase enzyme, wherein the histone-demethylase enzyme comprises a JmjC domain. In an additional embodiment is the method for inhibiting a histone-demethylase enzyme, wherein the histone-demethylase enzyme is selected from FBXL10 or FBXL11.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, the invention provides a method of treating a disease regulated by histone methylation and/or demethylation in a subject in need thereof by modulating the activity of FBXL10 or FBXL11.

In an additional embodiment is a method for treating cancer in subject comprising administering a composition comprising a compound of Formula (I) or (II), or a pharmaceutically acceptable salt thereof.

In a further embodiment is the method for treating cancer in a subject wherein the cancer is selected from pancreatic cancer, prostate cancer, breast cancer, gastric cancer, leukemia, bladder cancer, lung cancer or melanoma.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation 1A 2-(1-methylimidazol-4-yl)pyridine-4-carbonitrile

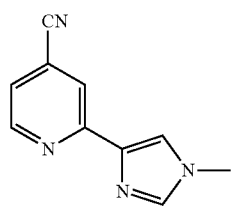

A mixture of 2-chloro-4-pyridinenitrile (1.85 g, 13.4 mmol), N-methyl-4-(tributylstannyl)imidazole (5 g, 13.4 mmol) and Pd(PPh$_3$)$_4$ (1.42 g, 1.34 mmol) in DMF (50 mL) was stirred for 3 hr at 130° C. under N$_2$. The mixture was concentrated and purified by flash column chromatography on silica gel (CH$_2$Cl$_2$/MeOH=20/1) to afford the title compound (2.0 g, 80%). [M+H] Calc'd for C$_{10}$H$_8$N$_4$, 185; Found, 185.

Preparation 1B trimethyl-[4-[2-(1-methylimidazol-4-yl)pyridin-4-yl]-1H-triazol-5-yl]silane

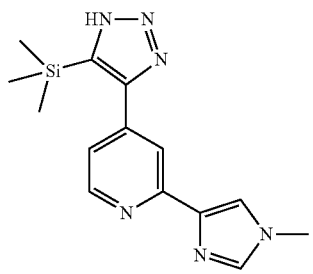

To a solution of TMSCHN$_2$ (0.76 mL, 1.52 mmol) in THF was added n-BuLi (0.60 mL, 1.52 mmol) at 0° C., stirred for 20 min, then a solution of 2-(1-methylimidazol-4-yl)pyridine-4-carbonitrile (200 mg, 1.09 mmol) in THF was added, and the reaction mixture was stirred overnight at rt. LC/MS showed the reaction was completed, sat. NH$_4$Cl was added and extracted with EtOAc, dried, concentrated to give the title compound (296 mg, 90%). [M+H] Calc'd for C$_{14}$H$_{18}$N$_6$Si, 299; Found, 299.

Example 1

2-(1-methylimidazol-4-yl)-4-(1H-triazol-4-yl)pyridine

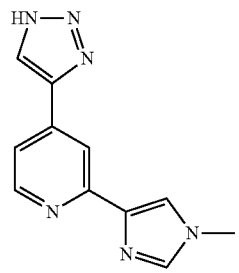 [SMILES: Cn1cnc(-c2cc(-c3c[nH]nn3)ccn2)c1]

A mixture of trimethyl-[4-[2-(1-methylimidazol-4-yl)pyridin-4-yl]-1H-triazol-5-yl]silane (296 mg, 0.99 mmol) and NaOH (2.2 mL, 4.46 mmol, 2M) in MeOH was stirred overnight at 50° C. LC/MS showed the reaction was completed, H$_2$O was added, extracted with ethyl acetate, dried, purified by HPLC to give the title compound (38 mg, 18%) as a yellow solid. $^1$H NMR (300 MHz, CD$_3$OD): δ 3.99 (3H, s), 7.96 (1H, dd, J=5.4 Hz, J=1.2 Hz), 8.21 (1H, d, J=0.6 Hz), 8.46 (1H, s), 8.47-8.64 (1H, m), 8.65 (1H, s), 8.69 (1H, d, J=5.4 Hz). [M+H] Calc'd for C$_{11}$H$_{10}$N$_6$, 227; Found, 227.

Preparation 2A

2-[1-[(2-chlorophenyl)methyl]imidazol-4-yl]pyridine-4-carboxamide

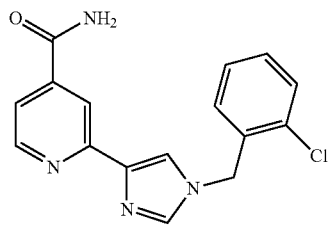 [SMILES: NC(=O)c1ccnc(-c2cn(Cc3ccccc3Cl)cn2)c1]

A mixture of 2-(1H-imidazol-4-yl)pyridine-4-carboxamide (1 g, 5.32 mmol), 1-bromomethyl-2-chloro-benzene (2.17 g, 10.64 mmol) and $K_2CO_3$ (1.47 g, 10.64 mmol) in DMF (50 mL) was stirred overnight at rt. LC/MS showed the reaction was completed. The mixture was concentrated and purified by flash column chromatography on silica gel ($CH_2Cl_2$/MeOH=20/1) to afford the title compound (1.2 g, 66%). [M+H] Calc'd for $C_{16}H_{13}ClN_4O$, 313; Found, 313.

Preparation 2B

2-[1-[(2-chlorophenyl)methyl]imidazol-4-yl]pyridine-4-carbonitrile

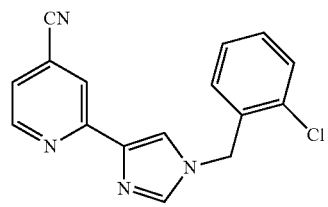 [SMILES: N#Cc1ccnc(-c2cn(Cc3ccccc3Cl)cn2)c1]

To a solution of 2-[1-[(2-chlorophenyl)methyl]imidazol-4-yl]pyridine-4-carboxamide (1.2 g, 3.54 mmol) and pyridine (0.91 g, 10.64 mmol) in $CH_2Cl_2$ was added trifluoroacetic acid anhydride (1.62 g, 7.08 mmol) at 0° C., which was then stirred for 2 hr at 0° C. LC/MS showed the reaction was completed. $H_2O$ was added and extracted with $CH_2Cl_2$, the organic layer was washed by aqueous $NaHCO_3$ and brine, dried, concentrated and purified by flash column chromatography on silica gel (PE/EA=1/3) to give the title compound (844 mg, 74%). [M+H] Calc'd for $C_{16}H_{11}ClN_4$, 295; Found, 295.

Preparation 2C

[4-[2-[1-[(2-chlorophenyl)methyl]imidazol-4-yl]pyridin-4-yl]-1H-triazol-5-yl]-trimethylsilane

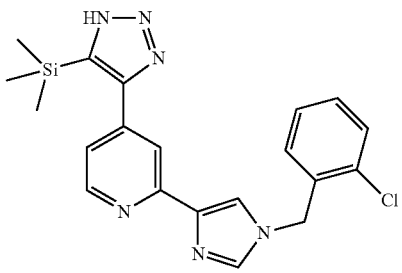 [SMILES: C[Si](C)(C)c1[nH]nnc1-c1ccnc(-c2cn(Cc3ccccc3Cl)cn2)c1]

The title compound was prepared in 98% yield according to the procedure of Preparation 1B. [M+H] Calc'd for $C_{20}H_{21}ClN_6Si$, 409; Found, 409.

Example 2

2-[1-[(2-chlorophenyl)methyl]imidazol-4-yl]-4-(1H-triazol-4-yl)pyridine

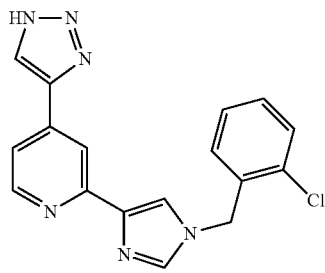 [SMILES: Clc1ccccc1Cn1cnc(-c2cc(-c3c[nH]nn3)ccn2)c1]

The title compound was prepared in 44% yield according to the procedure of last step of Example 1. $^1$H NMR (300 MHz, $CD_3OD$): δ 5.58 (2H, s), 7.44-7.54 (4H, m), 8.03 (1H, d, J=5.7 Hz), 8.22 (1H, s), 8.55-8.65 (4H, m). [M+H] Calc'd for $C_{17}H_{13}ClN_6$, 337; Found, 337.

Preparation 3A 2-(5-bromo-1-methylimidazol-4-yl)pyridine-4-carbonitrile

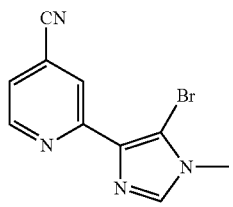

To a solution of 2-(1-methylimidazol-4-yl)pyridine-4-carbonitrile (600 mg, 3.26 mmol, Preparation 1A) in $CH_2Cl_2$ (30 mL), was added NBS (610 mg, 3.42 mmol) and it was stirred for 3 hr at rt. Washed by $H_2O$, dried and concentrated to afford the title compound (810 mg, 95%). [M+H] Calc'd for $C_{10}H_7BrN_4$, 263; Found, 263.

Preparation 3B

2-[5-(4-fluorophenyl)-1-methylimidazol-4-yl]pyridine-4-carbonitrile

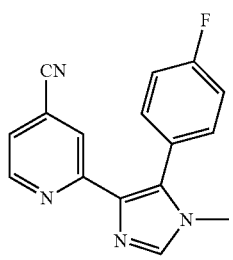 [SMILES: Cn1cnc(-c2cc(C#N)ccn2)c1-c1ccc(F)cc1]

A mixture of 2-(5-bromo-1-methylimidazol-4-yl)pyridine-4-carbonitrile (1 eq), 4-fluorophenylboronic acid (1.2 eq), Pd(dppf)Cl₂ (0.1 eq) and 2M Na₂CO₃ (2 eq) in dioxane was refluxed overnight under N₂, concentrated and purified by flash column chromatography (DCM/MeOH=20/1) to give the title compound (140 mg, 50%). [M+H] Calc'd for $C_{16}H_{11}FN_4$, 279; Found, 279.

Preparation 3C

[4-[2-[5-(4-fluorophenyl)-1-methylimidazol-4-yl]pyridin-4-yl]-1H-triazol-5-yl]-trimethylsilane

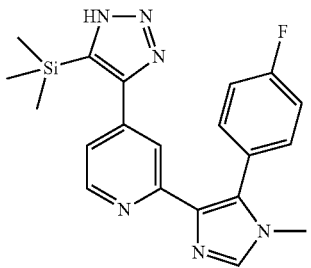

The title compound was prepared in 87% yield according to the procedure of Preparation 1B. [M+H] Calc'd for $C_{20}H_{21}FN_6Si$, 393; Found, 393.

Example 3

2-[5-(4-fluorophenyl)-1-methylimidazol-4-yl]-4-(1H-triazol-4-yl)pyridine

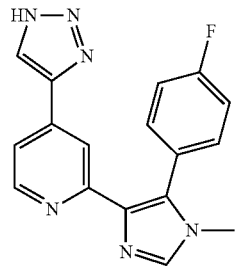 [SMILES: Cn1cnc(-c2cc(-c3c[nH]nn3)ccn2)c1-c1ccc(F)cc1]

The title compound was prepared in 12% yield according to the procedure of last step of Example 1. ¹H NMR (300 MHz, DMSO+CD₃OD): δ 3.61 (3H, s), 7.44-7.85 (6H, m), 8.30 (1H, s), 8.64 (1H, d, J=5.4 Hz), 8.84-8.85 (1H, m). [M+H] Calc'd for $C_{17}H_{13}FN_6$, 321; Found, 321.

Preparation 4A

2-[5-[2-(cyclopropylmethoxy)-4-fluorophenyl]-1-methylimidazol-4-yl]-4-(1H-triazol-4-yl)pyridine

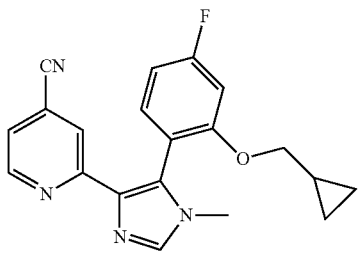 [SMILES: Cn1cnc(-c2cc(C#N)ccn2)c1-c1ccc(F)cc1OCC1CC1]

The title compound was prepared in 25% yield according to the procedure of Preparation 3B. [M+H] Calc'd for $C_{20}H_{17}FN_4O$, 349; Found, 349.

Preparation 4B

[4-[2-[5-[2-(cyclopropylmethoxy)-4-fluorophenyl]-1-methylimidazol-4-yl]pyridin-4-yl]-1H-triazol-5-yl]-trimethylsilane

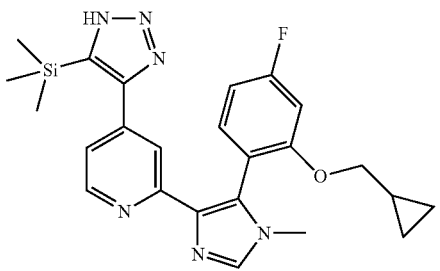 [SMILES: Cn1cnc(-c2cc(-c3nn[nH]c3[Si](C)(C)C)ccn2)c1-c1ccc(F)cc1OCC1CC1]

The title compound was prepared in 25% yield according to the procedure of Preparation 1B. [M+H] Calc'd for $C_{24}H_{27}FN_6OSi$, 463; Found, 463.

Example 4

2-[5-[2-(cyclopropylmethoxy)-4-fluorophenyl]-1-methylimidazol-4-yl]-4-(1H-triazol-4-yl)pyridine

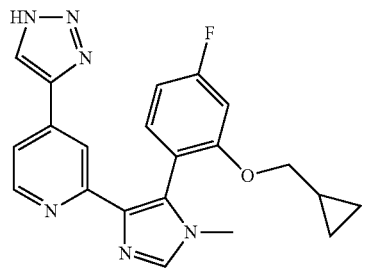 [SMILES: Cn1cnc(-c2cc(-c3c[nH]nn3)ccn2)c1-c1ccc(F)cc1OCC1CC1]

The title compound was prepared in 13% yield according to the procedure of last step of Example 1. ¹H NMR (300 MHz, DMSO+CD₃OD): δ 0.10-0.36 (4H, m), 0.91-0.98 (1H, m), 3.37 (3H, s), 3.72-3.82 (2H, m), 6.80-6.81 (1H, m), 6.97 (1H, d, J=10.5 Hz), 7.28 (1H, t, J=3.6 Hz), 7.52 (1H, d, J=4.8 Hz), 7.86 (1H, s), 8.25-8.33 (3H, m). [M+H] Calc'd for $C_{21}H_{19}FN_6O$, 391; Found, 391.

Example 5

2-[1-(1-phenylethyl)imidazol-4-yl]-4-(1H-triazol-4-yl)pyridine

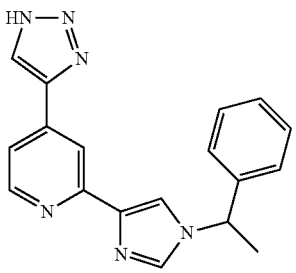 [SMILES: CC(c1ccccc1)n1cnc(-c2cc(-c3c[nH]nn3)ccn2)c1]

The title compound was prepared in 6% overall yield according to the procedure of Example 2 starting from 2-(1H-imidazol-4-yl)pyridine-4-carboxamide. $^1$H NMR (300 MHz, CD$_3$OD): δ 1.94 (3H, d, J=14.1 Hz), 5.58-5.65 (1H, m), 7.32-7.44 (5H, m), 7.75 (1H, d, J=5.1 Hz), 7.83 (1H, s), 7.94 (1H, s), 8.39 (2H, s), 8.52 (1H, d, J=5.1 Hz). [M+H] Calc'd for C$_{18}$H$_{16}$N$_6$, 317; Found, 317.

Preparation 6A

2-[1-[2-(2-chlorophenyl)ethyl]imidazol-4-yl]pyridine-4-carboxamide

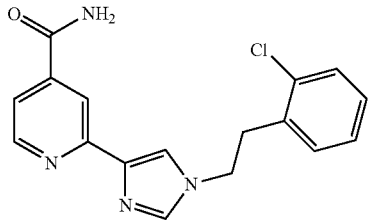 [SMILES: NC(=O)c1ccnc(-c2cn(CCc3ccccc3Cl)cn2)c1]

A mixture of 2-(1H-imidazol-4-yl)pyridine-4-carboxamide (500 mg, 2.66 mmol), 1-(2-bromo-ethyl)-2-chloro-benzene (2.32 g, 10.64 mmol) and K$_2$CO$_3$ (1.47 g, 10.64 mmol) in DMF (20 mL) was stirred overnight at 100° C. LC/MS showed the reaction was completed. The reaction mixture was purified by flash column chromatography to give the title compound (300 mg, 34%) as a yellow solid. [M+H] Calc'd for C$_{17}$H$_{15}$ClN$_4$O, 327; Found, 327.

Preparation 6B

2-[1-[2-(2-chlorophenyl)ethyl]imidazol-4-yl]pyridine-4-carbonitrile

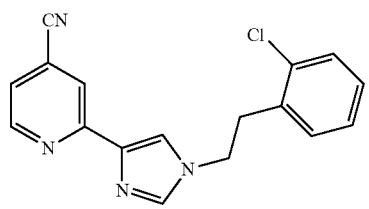 [SMILES: N#Cc1ccnc(-c2cn(CCc3ccccc3Cl)cn2)c1]

The title compound was prepared in 77% yield according to the procedure of Preparation 2B. [M+H] Calc'd for C$_{17}$H$_{13}$ClN$_4$, 309; Found, 309.

Preparation 6C

[4-[2-[1-[2-(2-chlorophenyl)ethyl]imidazol-4-yl]pyridin-4-yl]-1H-triazol-5-yl]-trimethylsilane

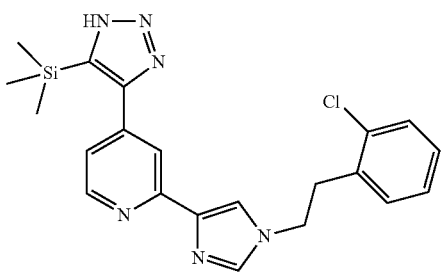 [SMILES: C[Si](C)(C)c1[nH]nnc1-c1ccnc(-c2cn(CCc3ccccc3Cl)cn2)c1]

The title compound was prepared in 100% yield according to the procedure of Preparation 1B. [M+H] Calc'd for C$_{21}$H$_{23}$ClN$_6$Si, 423; Found, 423.

Example 6

2-[1-[2-(2-chlorophenyl)ethyl]imidazol-4-yl]-4-(1H-triazol-4-yl)pyridine

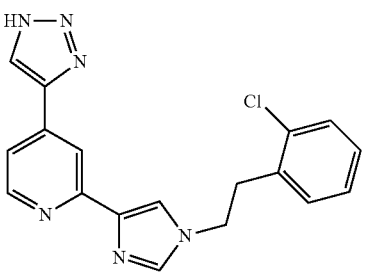 [SMILES: Clc1ccccc1CCn1cnc(-c2cc(-c3c[nH]nn3)ccn2)c1]

The title compound was prepared in 42% yield according to the procedure of last step of Example 1. $^1$H NMR (300 MHz, CD$_3$OD): δ 3.23 (2H, t, J=7.2 Hz), 4.31 (2H, t, J=7.2 Hz), 7.25-7.28 (3H, m), 7.44-7.47 (1H, m), 7.63-7.64 (2H, m), 7.79 (1H, s), 8.30 (1H, s), 8.53 (1H, d, J=5.1 Hz), 8.62 (1H, s). [M+H] Calc'd for C$_{18}$H$_{15}$ClN$_6$, 351; Found, 351.

Example 7

2-[1-[2-(2-methoxyphenyl)ethyl]imidazol-4-yl]-4-(1H-triazol-4-yl)pyridine

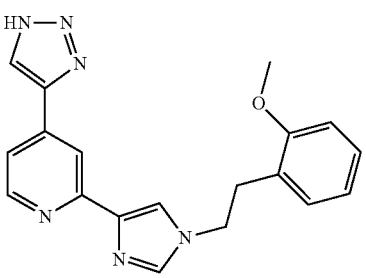 [SMILES: COc1ccccc1CCn1cnc(-c2cc(-c3c[nH]nn3)ccn2)c1]

The title compound was prepared in 12% overall yield according to the procedure of Example 6 starting from 2-(1H-imidazol-4-yl)pyridine-4-carboxamide. $^1$H NMR (300 MHz, CD$_3$OD): δ 3.14 (2H, t, J=6.9 Hz), 3.82 (3H, s), 4.32 (2H, t, J=6.9 Hz), 6.81-7.22 (4H, m), 7.52 (1H, s), 7.68 (1H, s), 7.73 (1H, d, J=5.4 Hz), 8.32 (1H, s), 8.37 (1H, s), 8.52 (1H, d, J=5.4 Hz). [M+H] Calc'd for C$_{19}$H$_{18}$N$_6$O, 347; Found, 347.

Example 8

2-[1-(1,2,3,4-tetrahydronaphthalen-1-ylmethyl)imidazol-4-yl]-4-(1H-triazol-4-yl)pyridine

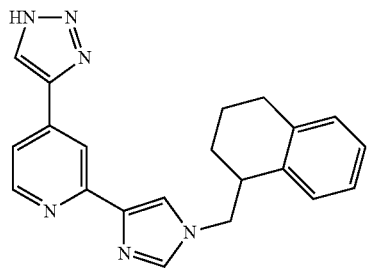 [SMILES: c1ccc2c(c1)CCCC2Cn1cnc(-c2cc(-c3c[nH]nn3)ccn2)c1]

The title compound was prepared in 12% overall yield according to the procedure of Example 6 starting from 2-(1H-imidazol-4-yl)pyridine-4-carboxamide. $^1$H NMR (300 MHz, DMSO): δ 1.45-1.85 (4H, m), 2.69-2.74 (2H, m), 3.28-3.34 (1H, m), 4.11-4.35 (2H, m), 7.09-7.16 (3H, m), 7.28-7.31 (1H, m), 7.65 (1H, d, J=5.4 Hz), 7.77 (1H, s), 7.88 (1H, s), 8.34 (1H, s), 8.84 (1H, d, J=5.4 Hz), 8.34 (1H, s). [M+H] Calc'd for $C_{21}H_{20}N_6$, 357; Found, 357.

Preparation 9A

2-[1-[2-(2-ethoxyphenyl)ethyl]imidazol-4-yl]pyridine-4-carboxamide

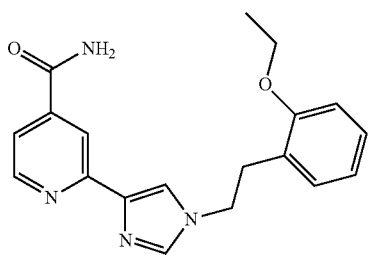 [SMILES: CCOc1ccccc1CCn1cnc(-c2cc(C(N)=O)ccn2)c1]

A mixture of 2-(1H-imidazol-4-yl)pyridine-4-carboxamide (1 eq), ROMs (1.2 eq) and $K_2CO_3$ (2 eq) in DMF (50 mL) was stirred overnight at 80° C. LC/MS showed the reaction was completed. The mixture was concentrated and purified by flash column chromatography on silica gel (DCM/MeOH=20/1) to afford the title compound. [M+H] Calc'd for $C_{19}H_{20}N_4O_2$, 337; Found, 337.

Preparation 9B

2-[1-[2-(2-ethoxyphenyl)ethyl]imidazol-4-yl]pyridine-4-carbonitrile

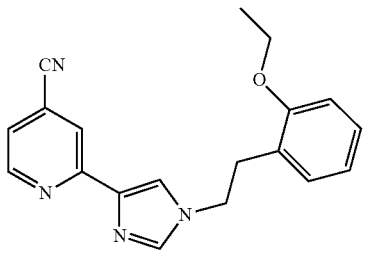 [SMILES: CCOc1ccccc1CCn1cnc(-c2cc(C#N)ccn2)c1]

The title compound was prepared in 60% yield according to the procedure of Preparation 2B. [M+H] Calc'd for $C_{19}H_{18}N_4O$, 319; Found, 319.

Preparation 9C

[4-[2-[1-[2-(2-ethoxyphenyl)ethyl]imidazol-4-yl]pyridin-4-yl]-1H-triazol-5-yl]-trimethylsilane

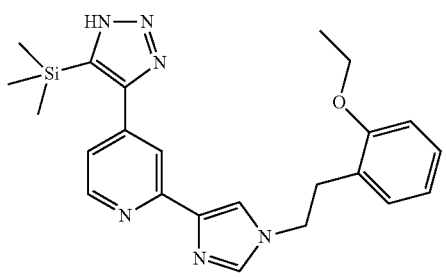 [SMILES: CCOc1ccccc1CCn1cnc(-c2cc(-c3nn[nH]c3[Si](C)(C)C)ccn2)c1]

The title compound was prepared in 100% yield according to the procedure of Preparation 1B. [M+H] Calc'd for $C_{23}H_{28}N_6OSi$, 433; Found, 433.

Example 9

2-[1-[2-(2-ethoxyphenyl)ethyl]imidazol-4-yl]-4-(1H-triazol-4-yl)pyridine

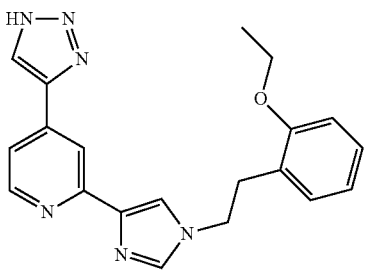 [SMILES: CCOc1ccccc1CCn1cnc(-c2cc(-c3c[nH]nn3)ccn2)c1]

The title compound was prepared in 54% yield according to the procedure of the last step of Example 1. $^1$H NMR (300 MHz, DMSO): δ 1.36 (3H, t, J=6.9 Hz), 3.06 (2H, t, J=6.9 Hz), 4.02 (2H, q, J=6.9 Hz), 4.25 (2H, t, J=6.9 Hz), 6.79-7.22 (4H, m), 7.59 (1H, s), 7.63 (1H, d, J=4.2 Hz), 7.72 (1H, s), 8.30 (1H, s), 8.53 (1H, d, J=5.4 Hz), 8.62 (1H, s). [M+H] Calc'd for C$_{20}$H$_{20}$N$_6$O, 361; Found, 361.

Example 10

4-(1H-triazol-4-yl)-2-[1-[2-[2-(2,2,2-trifluoroethoxy)phenyl]ethyl]imidazol-4-yl]pyridine

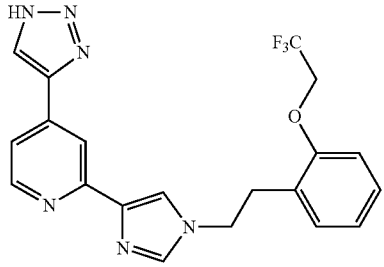 [SMILES: FC(F)(F)COc1ccccc1CCn1cnc(-c2cc(-c3c[nH]nn3)ccn2)c1]

The title compound was prepared in 11% overall yield according to the procedure of Example 9 starting from 2-(1H-imidazol-4-yl)pyridine-4-carboxamide. $^1$H NMR (300 MHz, DMSO): δ 3.10 (2H, t, J=7.2 Hz), 4.25 (2H, t, J=7.2 Hz), 4.81 (2H, q, J=9.0 Hz), 6.93-7.26 (4H, m), 7.56 (1H, s), 7.63 (1H, d, J=4.5 Hz), 7.71 (1H, s), 8.30 (1H, s), 8.53 (1H, d, J=4.8 Hz), 8.64 (1H, m). [M+H] Calc'd for C$_{20}$H$_{17}$F$_3$N$_6$O, 415; Found, 415.

Example 11

2-[1-[2-[2-(cyclopropylmethoxy)phenyl]ethyl]imidazol-4-yl]-4-(1H-triazol-4-yl)pyridine

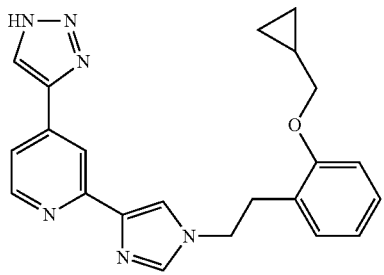 [SMILES: c1ccc(OCC2CC2)c(CCn2cnc(-c3cc(-c4c[nH]nn4)ccn3)c2)c1]

The title compound was prepared in 3% overall yield according to the procedure of Example 9 starting from 2-(1H-imidazol-4-yl)pyridine-4-carboxamide. $^1$H NMR (300 MHz, DMSO): δ 0.36-0.37 (2H, m), 0.57-0.60 (2H, m), 1.30-1.35 (1H, m), 3.07 (2H, t, J=6.9 Hz), 3.85 (2H, d, J=5.7 Hz), 4.47 (2H, t, J=6.6 Hz), 6.81-7.18 (4H, m), 7.60-7.63 (2H, m), 7.74 (1H, s), 8.30 (1H, s), 8.52-8.53 (2H, m). [M+H] Calc'd for C$_{22}$H$_{22}$N$_6$O, 387; Found, 387.

Example 12

2-[1-(3,4-dihydro-2H-chromen-4-ylmethyl)imidazol-4-yl]-4-(1H-triazol-4-yl)pyridine

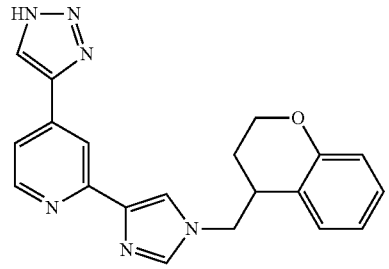 [SMILES: c1ccc2c(c1)OCCC2Cn1cnc(-c2cc(-c3c[nH]nn3)ccn2)c1]

The title compound was prepared in 4% overall yield according to the procedure of Example 9 starting from 2-(1H-imidazol-4-yl)pyridine-4-carboxamide. $^1$H NMR (300 MHz, DMSO): δ 1.64-1.83 (2H, m), 3.30-3.33 (1H, m), 4.13-4.46 (4H, m), 6.77-6.90 (2H, m), 7.11-7.26 (2H, m), 7.65 (1H, d, J=5.7 Hz), 7.80 (1H, s), 7.92 (1H, s), 8.34 (1H, s), 8.55 (1H, d, J=5.7 Hz), 8.64 (1H, m). [M+H] Calc'd for C$_{20}$H$_{18}$N$_6$O, 359; Found, 359.

Preparation 13A

2-[1-[(2-chlorophenyl)methyl]imidazol-4-yl]pyridine-4-carboxylic acid

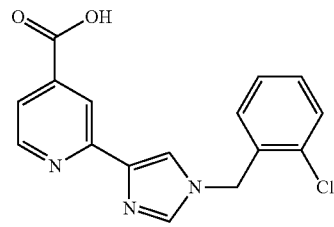 [SMILES: O=C(O)c1ccnc(-c2cn(Cc3ccccc3Cl)cn2)c1]

A mixture of 2-[1-[(2-chlorophenyl)methyl]imidazol-4-yl]pyridine-4-carbonitrile (430 mg, 1.46 mmol, Preparation 2B) and NaOH (1.5 mL, 7.31 mmol, 5M) in EtOH was refluxed overnight. LC/MS showed the reaction was completed, cooled to rt and acidified to pH=3-4 by 1N HCl, the solid was collected, dried to give the title compound (424 mg, 92%). [M+H] Calc'd for C$_{16}$H$_{12}$ClN$_3$O$_2$, 314; Found, 314.

Preparation 13B

[2-[1-[(2-chlorophenyl)methyl]imidazol-4-yl]pyridin-4-yl]methanol

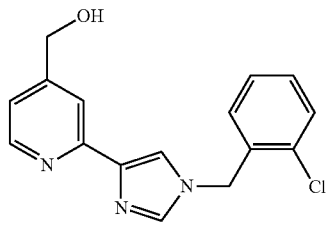 [SMILES: OCc1ccnc(-c2cn(Cc3ccccc3Cl)cn2)c1]

To a solution of 2-[1-[(2-chlorophenyl)methyl]imidazol-4-yl]pyridine-4-carboxylic acid (424 mg, 1.34 mmol) in THF was added a solution of LiAlH$_4$ in THF (1.8 mL, 4.43 mmol, 2.4 M) at 0° C., then stirred for 2 hr at rt. LC/MS showed the reaction was completed. 0.1 mL H$_2$O, 0.1 mL NaOH, and 0.3 mL H$_2$O was added subsequently, filtered, concentrated to give the title compound (405 mg, 100%). [M+H] Calc'd for C$_{16}$H$_{14}$ClN$_3$O, 300; Found, 300.

Preparation 13C

2-[1-[(2-chlorophenyl)methyl]imidazol-4-yl]pyridine-4-carbaldehyde

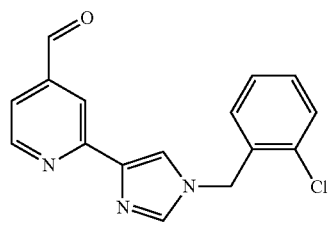 [SMILES: O=Cc1ccnc(-c2cn(Cc3ccccc3Cl)cn2)c1]

To a solution of Dess-Martin oxidant (640 mg, 1.5 mmol) in THF (20 mL) was added a solution of [2-[1-[(2-chlorophenyl)methyl]imidazol-4-yl]pyridin-4-yl]methanol (300 mg, 1.0 mmol) at 0° C. The reaction mixture was stirred for 2 hr at rt. LC/MS showed the reaction was completed. NaOH (42 mL, 42 mmol) was added to quench the reaction. It was then extracted by EtOAc, dried and concentrated to give the title compound (300 mg, 61%). [M+H] Calc'd for C$_{16}$H$_{12}$ClN$_3$O, 298; Found, 298.

Preparation 13D 2-(benzenesulfonyl)-3-[2-[1-[(2-chlorophenyl)methyl]imidazol-4-yl]pyridin-4-yl]prop-2-enenitrile

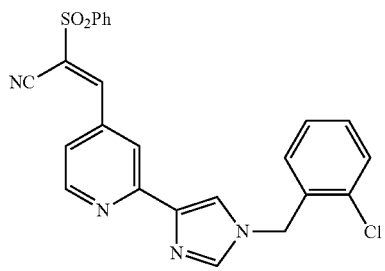

A mixture of 2-[1-[(2-chlorophenyl)methyl]imidazol-4-yl]pyridine-4-carbaldehyde (100 mg, 0.33 mmol), 2-(benzenesulfonyl)acetonitrile (60 mg, 0.33 mmol) and NaHCO$_3$ (1.64 mL, 0.41 mmol, 0.25 M) in EtOH was stirred overnight at rt. LC/MS showed the reaction was completed, concentrated and purified by preparative TLC (DCM/MeOH=20/1) to give the title compound (40 mg, 26%). [M+H] Calc'd for C$_{24}$H$_{17}$ClN$_4$O$_2$S, 461; Found, 461.

Example 13

4-[2-[1-[(2-chlorophenyl)methyl]imidazol-4-yl]pyridin-4-yl]-1H-triazole-5-carbonitrile

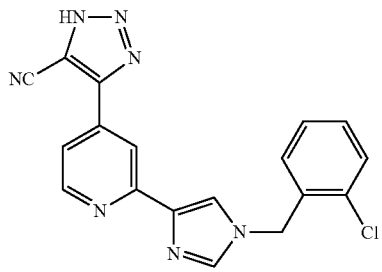 [SMILES: N#Cc1[nH]nnc1-c1ccnc(-c2cn(Cc3ccccc3Cl)cn2)c1]

A mixture of 2-(benzenesulfonyl)-3-[2-[1-[(2-chlorophenyl)methyl]imidazol-4-yl]pyridin-4-yl]prop-2-enenitrile (40 mg, 0.086 mmol, Preparation 13D) and NaN$_3$ (6 mg, 0.086 mmol) in DMF was stirred for 2 hr at 100° C. LC/MS showed the reaction was completed, acidified to pH=3-4 by 1N HCl, and stirred for 30 min, then adjusted to pH=7-8 by 1N NaOH, concentrated and purified by prep-HPLC to give the title compound (12 mg, 39%). $^1$H NMR (400 MHz, CD$_3$OD): δ 5.64 (2H, s), 7.46-7.53 (4H, m), 7.92 (1H, d, J=5.6 Hz), 8.20 (1H, s), 8.35 (1H, s), 8.74 (1H, d, J=5.2 Hz), 9.01 (1H, s). [M+H] Calc'd for C$_{18}$H$_{12}$ClN$_7$, 362; Found, 362.

Example 14

4-[2-[1-[(2,3-dichlorophenyl)methyl]imidazol-4-yl]pyridin-4-yl]-1H-triazole-5-carbonitrile

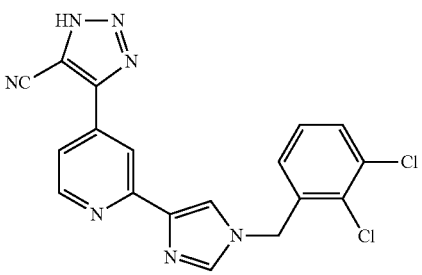 [SMILES: N#Cc1[nH]nnc1-c1ccnc(-c2cn(Cc3cccc(Cl)c3Cl)cn2)c1]

The title compound was prepared in 3% overall yield according to the procedure of Example 13 starting from 2-[1-[(2,3-dichlorophenyl)methyl]imidazol-4-yl]pyridine-4-carbonitrile. $^1$H NMR (300 MHz, DMSO): δ 5.43 (2H, s), 7.12-7.15 (1H, m), 7.37-7.43 (1H, m), 7.60-7.93 (4H, m), 8.41-8.49 (2H, m). [M+H] Calc'd for C$_{18}$H$_{11}$Cl$_2$N$_7$, 396; Found, 396.

Example 15

4-[2-[1-(1,2,3,4-tetrahydronaphthalen-1-ylmethyl)imidazol-4-yl]pyridin-4-yl]-1H-triazole-5-carbonitrile

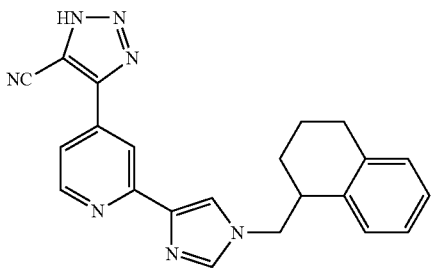 [SMILES: N#Cc1[nH]nnc1-c1ccnc(-c2cn(CC3CCCc4ccccc43)cn2)c1]

The title compound was prepared in 2% overall yield according to the procedure of Example 13 starting from 2-[1-(1,2,3,4-tetrahydronaphthalen-1-ylmethyl)imidazol-4-yl]pyridin-4-carbonitrile. $^1$H NMR (400 MHz, CD$_3$OD): δ 1.77-1.95 (4H, m), 2.84-2.86 (2H, m), 3.10-3.11 (1H, m), 4.49-4.60 (2H, m), 7.13-7.20 (4H, m), 8.06 (1H, d, J=4.8 Hz), 8.41 (1H, s), 8.46 (1H, s), 8.90 (1H, d, J=5.2 Hz), 9.01 (1H, s). [M+H] Calc'd for C$_{22}$H$_{19}$N$_7$, 382; Found, 382.

Example 16

4-[2-[1-(2-naphthalen-1-ylethyl)imidazol-4-yl]pyridin-4-yl]-1H-triazole-5-carbonitrile

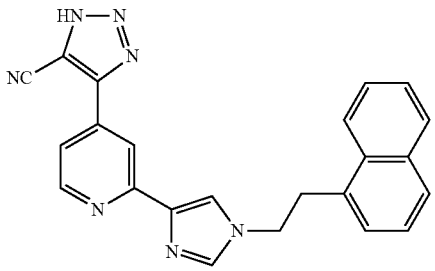 [SMILES: N#Cc1[nH]nnc1-c1ccnc(-c2cn(CCc3cccc4ccccc34)cn2)c1]

The title compound was prepared in 2% overall yield according to the procedure of Example 13 starting from 2-[1-(2-naphthalen-1-ylethyl)imidazol-4-yl]pyridin-4-carbonitrile. $^1$H NMR (300 MHz, CD$_3$OD): δ 3.75-3.77 (2H, m), 4.70-4.72 (2H, m), 7.31-7.57 (4H, m), 7.82-8.14 (4H, m), 8.27 (1H, s), 8.35 (1H, s), 8.72 (1H, s), 8.85 (1H, s). [M+H] Calc'd for C$_{23}$H$_{17}$N$_7$, 392; Found, 392.

Preparation 17a 2-(2-phenylmethoxyphenyl)ethanol

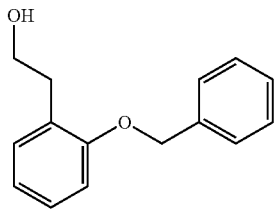 [SMILES: OCCc1ccccc1OCc1ccccc1]

A mixture of 2-(2-hydroxyethyl)phenol (1 g, 7.2 mmol), bromomethylbenzene (1.35 g, 7.92 mmol) and K$_2$CO$_3$ (2 g, 14.5 mmol) was stirred overnight at 90° C. H$_2$O was added, extracted with ethylacetate, purified by flash column chromatography on silica gel (PE/EA=1/1) to afford the title compound (1.48 g, 90%). [M+H] Calc'd for C$_{15}$H$_{16}$O$_2$, 229; Found, 229.

Preparation 17b 2-(2-phenylmethoxyphenyl)ethyl methanesulfonate

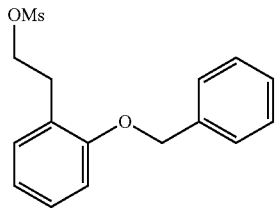 [SMILES: CS(=O)(=O)OCCc1ccccc1OCc1ccccc1]

To a solution of 2-(2-phenylmethoxyphenyl)ethanol (1.48 g, 6.48 mmol) and triethylamine (1.31 g, 13 mmol) in CH$_2$Cl$_2$ (20 mL) was added MsCl (1.11 g, 9.7 mmol) at 0° C., then stirred for 2 hr at rt, washed by H$_2$O, dried, concentrated to give the title compound (1.6 g, 81%) which was used directly for next step. [M+H] Calc'd for C$_{16}$H$_{18}$O$_4$S, 307; Found, 307.

Example 17

2-[1-[2-(2-phenylmethoxyphenyl)ethyl]imidazol-4-yl]-4-(1H-triazol-4-yl)pyridine

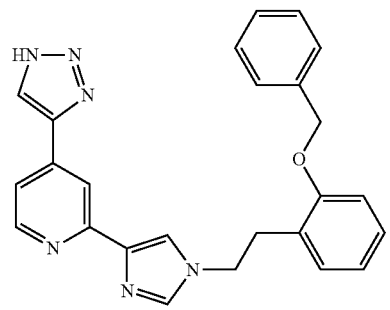 [SMILES: c1ccc(COc2ccccc2CCn2cnc(-c3cc(-c4c[nH]nn4)ccn3)c2)cc1]

The title compound was prepared in 4% overall yield according to the procedure of Example 9 starting from 2-(2-phenylmethoxyphenyl)ethyl methanesulfonate and 2-(1H-imidazol-4-yl)pyridine-4-carboxamide. $^1$H NMR (300 MHz, DMSO): δ 3.11 (2H, t, J=6.9 Hz), 4.26 (2H, t, J=6.9 Hz), 5.16 (2H, s), 6.83-7.74 (12H, m), 8.30 (1H, s), 8.54-8.64 (2H, m). [M+H] Calc'd for C$_{25}$H$_{22}$N$_6$O, 423; Found, 423.

Preparation 18a 2-(2-phenoxyphenyl)ethanol

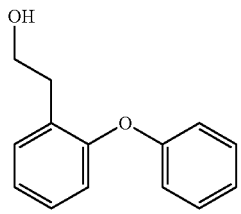 [SMILES: OCCc1ccccc1Oc1ccccc1]

A mixture of 2-(2-hydroxyethyl)phenol (1 g, 7.2 mmol), bromobenzene (1.70 g, 10.8 mmol), 1-pyridin-2-yl-propan-2-one (194 mg, 1.44 mmol), CuBr (103 mg, 0.72 mmol) and $Cs_2CO_3$ (4.73 g, 14.5 mmol) in DMSO (20 mL) was stirred overnight at 80° C., $H_2O$ was added, extracted with EtOAc, purified by flash column chromatography on silica gel (PE/EA=1/1) to afford the title compound (850 mg, 54%). [M+H] Calc'd for $C_{14}H_{14}O_2$, 215; Found, 215.

Preparation 18b 2-(2-phenoxyphenyl)ethyl methanesulfonate

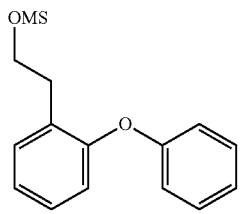

The title compound was prepared in 100% yield according to the procedure of Preparation 17b. [M+H] Calc'd for $C_{15}H_{16}O_4S$, 293; Found, 293.

Example 18

2-[1-[2-(2-phenoxyphenyl)ethyl]imidazol-4-yl]-4-(1H-triazol-4-yl)pyridine

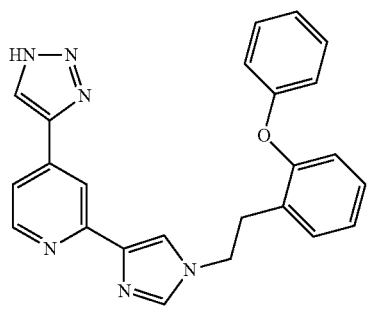 [SMILES: c1ccc(Oc2ccccc2CCn2cnc(-c3cc(-c4c[nH]nn4)ccn3)c2)cc1]

The title compound was prepared in 8% overall yield according to the procedure of Example 9 starting from 2-(2-phenoxyphenyl)ethyl methanesulfonate and 2-(1H-imidazol-4-yl)pyridine-4-carboxamide. $^1$H NMR (300 MHz, DMSO): δ 3.10 (2H, t, J=6.9 Hz), 4.29 (2H, t, J=6.9 Hz), 6.83-7.34 (9H, m), 7.59 (1H, s), 7.63 (1H, d, J=5.1 Hz), 7.72 (1H, s), 8.30 (1H, s), 8.52 (1H, d, J=5.1 Hz), 8.64 (1H, s). [M+H] Calc'd for $C_{24}H_{20}N_6O$, 409; Found, 409.

Preparation 19A

2-[1-[(2,3-dichlorophenyl)methyl]imidazol-4-yl]pyridine-4-carbaldehyde

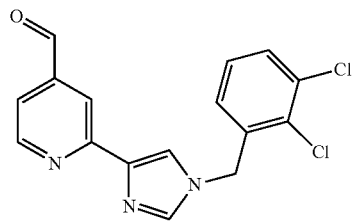 [SMILES: O=Cc1ccnc(-c2cn(Cc3cccc(Cl)c3Cl)cn2)c1]

The title compound was prepared in 19% overall yield according to the procedures of Preparation 13A-13C starting from 2-[1-[(2,3-dichlorophenyl)methyl]imidazol-4-yl]pyridine-4-carboxamide. [M+H] Calc'd for $C_{16}H_{11}Cl_2N_3O$, 332; Found, 332.

Preparation 19B

2-[1-[(2,3-dichlorophenyl)methyl]imidazol-4-yl]-4-ethynylpyridine

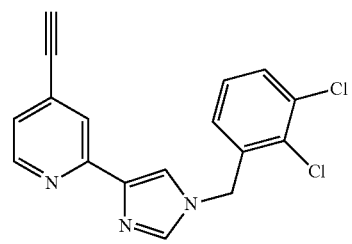 [SMILES: C#Cc1ccnc(-c2cn(Cc3cccc(Cl)c3Cl)cn2)c1]

A mixture of 2-[1-[(2,3-dichlorophenyl)methyl]imidazol-4-yl]pyridine-4-carbaldehyde (330 mg, 1.0 mmol) and $K_2CO_3$ (276 mg, 2.0 mmol) in MeOH (20 mL) was stirred for 15 min at rt, then (1-diazo-2-oxo-propyl)-phosphonic acid dimethyl ester (470 mg, 2.4 mmol) was added and stirred for 2 hr at rt. LC/MS showed the reaction was completed, concentrated and purified by flash column chromatography on silica gel ($CH_2Cl_2$/MeOH=20/1) to afford the title compound (260 mg, 79%). [M+H] Calc'd for $C_{17}H_{11}Cl_2N_3$, 328; Found, 328.

Preparation 19C

2-[1-[(2,3-dichlorophenyl)methyl]imidazol-4-yl]-4-
[5-iodo-1-[(4-methoxyphenyl)methyl]triazol-4-yl]
pyridine

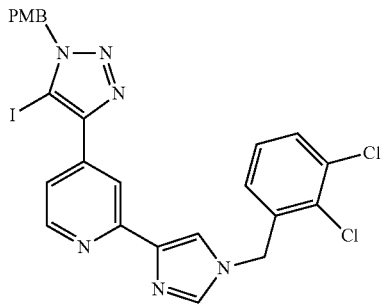

A mixture of 1-(azidomethyl)-4-methoxybenzene (310 mg, 1.86 mmol), KI (617 mg, 3.72 mmol) and Cu(ClO$_4$)$_2$·6H$_2$O (1.376 g, 3.72 mmol) in THF was stirred for 5 min at rt. Then triethylamine (375 mg, 3.72 mmol) and 2-[1-[(2,3-dichlorophenyl)methyl]imidazol-4-yl]-4-ethynylpyridine (610 mg, 1.86 mmol) were added sequentially and stirred for 1 h at rt. LC/MS showed the reaction was completed, diluted with EtOAc, washed by 25% NH$_3$·H$_2$O, dried and concentrated to give the title compound (916 mg, 80%). [M+H] Calc'd for C$_{25}$H$_{19}$Cl$_2$IN$_6$O, 617; Found, 617.

Example 19

2-[1-[(2,3-dichlorophenyl)methyl]imidazol-4-yl]-4-
(5-iodo-1H-triazol-4-yl)pyridine

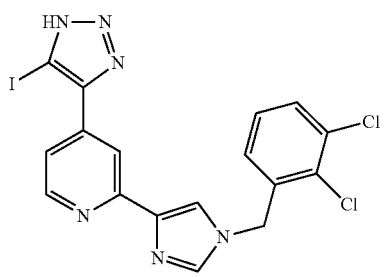

A solution of 2-[1-[(2,3-dichlorophenyl)methyl]imidazol-4-yl]-4-[5-iodo-1-[(4-methoxyphenyl)methyl]triazol-4-yl] pyridine (50 mg, 0.08 mmol) in TFA (3 ml) was stirred for 5 hr at 65° C. LC/MS showed the reaction was completed, concentrated and purified by prep-HPLC to give the title compound (10 mg, 25%). $^1$H NMR (400 MHz, CD$_3$OD): δ 5.62 (2H, s), 7.40-7.42 (2H, m), 7.63-7.66 (1H, m), 8.14-8.16 (1H, m), 8.23 (1H, s), 8.57 (1H, s), 8.69-8.72 (2H, m). [M+H] Calc'd for C$_{17}$H$_{11}$Cl$_2$IN$_6$, 497; Found, 497.

Preparation 20A

2-[1-[(2,3-dichlorophenyl)methyl]imidazol-4-yl]-4-
[5-fluoro-1-[(4-methoxyphenyl)methyl]triazol-4-yl]
pyridine

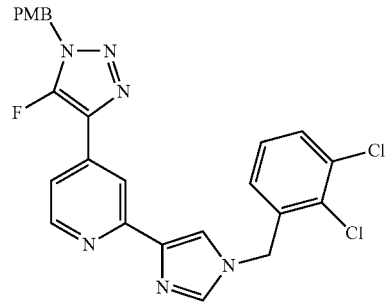

A mixture of 2-[1-[(2,3-dichlorophenyl)methyl]imidazol-4-yl]-4-[5-iodo-1-[(4-methoxyphenyl)methyl]triazol-4-yl] pyridine (70 mg, 0.11 mmol, Preparation 19C) and KF (33 mg, 0.55 mmol) in ACN/H$_2$O (2 ml/2 ml) was stirred for 10 min at 160° C. in a microwave oven. LC/MS showed the reaction was completed, H$_2$O was added, extracted with EtOAc, dried to give the title compound (46 mg, 80%) as a yellow solid. [M+H] Calc'd for C$_{25}$H$_{19}$Cl$_2$FN$_6$O, 509; Found, 509.

Example 20

2-[1-[(2,3-dichlorophenyl)methyl]imidazol-4-yl]-4-
(5-fluoro-1H-triazol-4-yl)pyridine

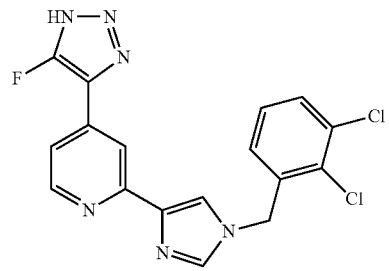 [SMILES: Fc1[nH]nnc1-c1ccnc(-c2cn(Cc3cccc(Cl)c3Cl)cn2)c1]

The title compound was prepared in 13% yield according to the procedure of last step of Example 19. $^1$H NMR (300 MHz, CD$_3$OD): δ 5.58 (2H, s), 7.36-7.41 (2H, m), 7.60-7.62 (1H, m), 7.81-7.82 (1H, m), 8.18-8.25 (2H, m), 8.39 (1H, s), 8.41 (1H, s). [M+H] Calc'd for C$_{17}$H$_{11}$Cl$_2$FN$_6$, 389; Found, 389.

Preparation 21A 2-(1H-imidazol-4-yl)pyridine-4-carbonitrile

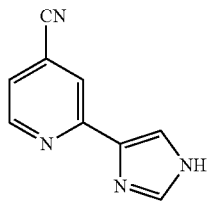 [SMILES: N#Cc1ccnc(-c2c[nH]cn2)c1]

A mixture of 2-chloro-4-pyridinenitrile (661 mg, 4.77 mmol), 4-(tributylstannyl)-1-tritylimidazole (3 g, 5 mmol) and Pd(PPh$_3$)$_4$ (276 mg, 0.24 mmol) in toluene (20 mL) was heated in a microwave oven for 2 hr at 120° C. The mixture was concentrated and purified by flash column chromatography on silica gel (EtOAc/hexane) to give the trityl protected product. It was then treated with HOAc/TFA (4 mL/5 mL) for 2 hrs. Purification by flash column chromatography gave the title compound (800 mg, 98%). [M+H] Calc'd for C$_9$H$_6$N$_4$, 171; Found, 171.

Example 21

2-[1-[(2,3-dichlorophenyl)methyl]imidazol-4-yl]-4-(1H-triazol-4-yl)pyridine

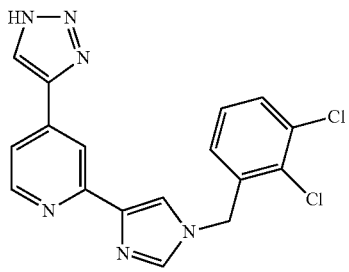

The title compound was prepared in 40% yield starting from 2-(1H-imidazol-4-yl)pyridine-4-carbonitrile (Preparation 21A) according to the procedure of Example 2. $^1$H NMR (400 MHz, DMSO-d6): δ 5.45 (2H, s), 7.13 (1H, d, J=6.7 Hz), 7.40 (1H, t, J=7.9 Hz), 7.63 (1H, br s), 7.65 (1H, d, J=8 Hz), 7.82 (1H, s), 7.93 (1H, s), 8.63 (1H, d, J=5.1 Hz), 8.96 (1H, br s). [M+H] Calc'd for C$_{17}$H$_{12}$Cl$_2$N$_6$, 371; Found, 371.

Example 22

2-[1-[[2-chloro-3-(trifluoromethyl)phenyl]methyl]imidazol-4-yl]-4-(1H-triazol-4-yl)pyridine

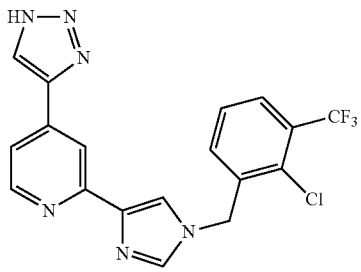 [SMILES: FC(F)(F)c1cccc(Cn2cnc(-c3cc(-c4c[nH]nn4)ccn3)c2)c1Cl]

The title compound was prepared in 4% yield starting from 2-(1H-imidazol-4-yl)pyridine-4-carbonitrile (Preparation 21A) according to the procedure of Example 2. $^1$H NMR (400 MHz, DMSO-d6): δ 5.52 (2H, s), 7.43 (1H, d, J=8.0 Hz), 7.59 (1H, t, J=7.9 Hz), 7.65 (1H, d, J=3.4 Hz), 7.86 (1H, d, J=6.7 Hz), 7.95 (1H, s), 8.35 (1H, s), 8.53 (2H, d, J=5.0 Hz). [M+H] Calc'd for C$_{18}$H$_{12}$ClF$_3$N$_6$, 405; Found, 405.

Example 23

2-[1-(2-naphthalen-1-ylethyl)imidazol-4-yl]-4-(1H-triazol-4-yl)pyridine

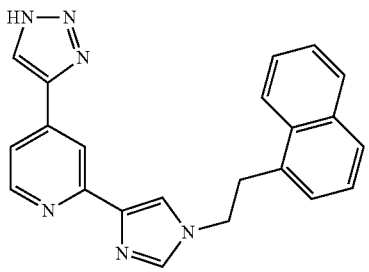 [SMILES: c1ccc2c(CCn3cnc(-c4cc(-c5c[nH]nn5)ccn4)c3)cccc2c1]

The title compound was prepared in 11% yield starting from 2-(1H-imidazol-4-yl)pyridine-4-carbonitrile (Preparation 21A) according to the procedure of Example 6. $^1$H NMR (400 MHz, DMSO-d6): δ 3.60 (2H, t, J=6.8 Hz), 4.39 (2H, t, J=6.9 Hz), 7.36 (1H, d, J=7.0 Hz), 7.42 (1H, t, J=7.0 Hz), 7.53-7.64 (3H, m), 7.69 (1H, s), 7.82 (1H, d, J=8.3 Hz), 7.91 (1H, s), 7.94 (1H, d, J=7.8 Hz), 8.24 (1H, d, J=8.4 Hz), 8.31 (1H, s), 8.53 (1H, d, J=4.9 Hz), 8.62 (1H, s). [M+H] Calc'd for C$_{22}$H$_{18}$N$_6$, 367; Found, 367.

Example 24

2-[5-(4-fluoro-3-methoxyphenyl)-1-methylimidazol-4-yl]-4-(1H-triazol-4-yl)pyridine

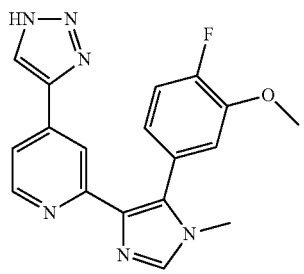 [SMILES: COc1cc(-c2c(-c3cc(-c4c[nH]nn4)ccn3)ncn2C)ccc1F]

The title compound was prepared in 20% yield according to the procedure of Example 3 starting from 2-(5-bromo-1-methylimidazol-4-yl)pyridine-4-carbonitrile (Preparation 3A). $^1$H NMR (400 MHz, DMSO-d6): δ 3.53 (3H, s), 3.82 (3H, s), 6.98-7.01 (1H, m), 7.23-7.30 (2H, m), 7.56 (1H, dd, J=5.0 and 1.6 Hz), 7.86 (1H, s), 8.18 (1H, s), 8.32 (1H, d, J=5.1 Hz), 8.35 (1H, s), 8.56 (1H, s). [M+H] Calc'd for C$_{18}$H$_{15}$FN$_6$O, 351; Found, 351.

Example 25

2-[5-(3-ethoxy-4-fluorophenyl)-1-methylimidazol-4-yl]-4-(1H-triazol-4-yl)pyridine

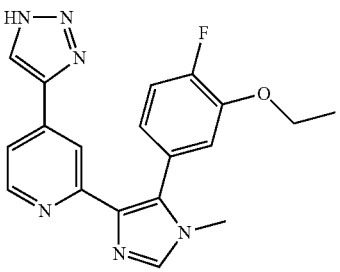 [SMILES: CCOc1cc(-c2c(-c3cc(-c4c[nH]nn4)ccn3)ncn2C)ccc1F]

The title compound was prepared in 16% yield according to the procedure of Example 3 starting from 2-(5-bromo-1-methylimidazol-4-yl)pyridine-4-carbonitrile (Preparation 3A). $^1$H NMR (400 MHz, DMSO-d6): δ 1.32 (3H, t, J=7.0 Hz), 3.50 (3H, s), 4.08 (2H, q, J=6.9 Hz), 6.96-7.00 (1H, m), 7.23-7.28 (2H, m), 7.56 (1H, dd, J=5.1 and 1.7 Hz), 7.86 (1H, s), 8.18 (1H, s), 8.32 (1H, d, J=5.1 Hz), 8.34 (1H, s), 8.56 (1H, s). [M+H] Calc'd for $C_{19}H_{17}FN_6O$, 365; Found, 365.

Example 26

2-[1-[[2-fluoro-3-(trifluoromethoxy)phenyl]methyl]imidazol-44-yl]-4-(1H-triazol-4-yl)pyridine

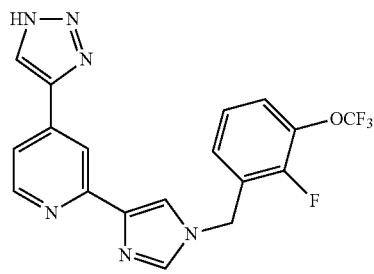 [SMILES: Fc1c(Cn2cnc(-c3cc(-c4c[nH]nn4)ccn3)c2)cccc1OC(F)(F)F]

The title compound was prepared in 17% yield starting from 2-(1H-imidazol-4-yl)pyridine-4-carbonitrile (Preparation 21A) according to the procedure of Example 2. $^1$H NMR (400 MHz, DMSO-d6): δ 5.45 (2H, s), 7.34-7.36 (2H, m), 7.55-7.57 (1H, m), 7.64-7.66 (1H, m), 7.81 (1H, s), 7.92 (1H, s), 8.25 (1H, s), 8.33 (1H, s), 8.52 (1H, d, J=5.1 Hz), 8.61 (1H, br s). [M+H] Calc'd for $C_{18}H_{12}F_4N_6O$, 405; Found, 405.

Example 27

2-[1-[2-(2-phenylphenyl)ethyl]imidazol-4-yl]-4-(1H-triazol-4-yl)pyridine

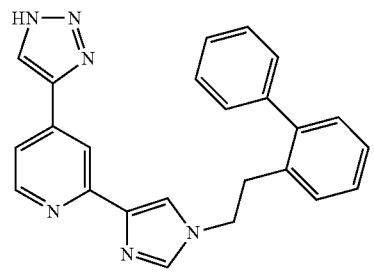 [SMILES: c1ccc(-c2ccccc2CCn2cnc(-c3cc(-c4c[nH]nn4)ccn3)c2)cc1]

The title compound was prepared in 4% overall yield according to the procedure of Example 6 starting from 2-(1H-imidazol-4-yl)pyridine-4-carbonitrile (Preparation 21A). $^1$H NMR (400 MHz, DMSO-d6): δ 3.04 (2H, t, J=7.3 Hz), 4.13 (2H, t, J=7.2 Hz), 7.20 (1H, m), 7.21-7.31 (5H, m), 7.33-7.47 (4H, m), 7.54 (1H, dd, J=5.4 and 1.6 Hz), 7.62 (1H, dd, J=5.1 and 1.6 Hz), 8.27 (1H, s), 8.32 (1H, s), 8.59 (1H, s). [M+H] Calc'd for $C_{24}H_{20}N_6$, 393; Found, 393.

Example 28

2-[1-[(2-fluoro-3-methylphenyl)methyl]imidazol-4-yl]-4-(1H-triazol-4-yl)pyridin

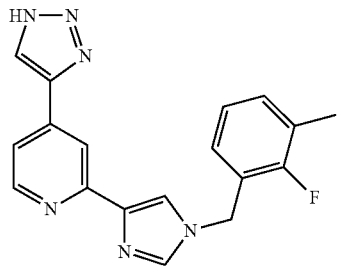 [SMILES: Cc1cccc(Cn2cnc(-c3cc(-c4c[nH]nn4)ccn3)c2)c1F]

The title compound was prepared in 7% yield starting from 2-(1H-imidazol-4-yl)pyridine-4-carbonitrile (Preparation 21A) according to the procedure of Example 2. $^1$H NMR (400 MHz, DMSO-d6): δ 2.14 (3H, s), 5.41 (2H, s), 7.11 (1H, t, J=7.8 Hz), 7.18 (1H, m), 7.28 (1H, m), 7.63 (1H, m), 7.74 (1H, s), 7.87 (1H, s), 8.32 (1H, s), 8.52 (1H, d, J=7.3 Hz). [M+H] Calc'd for $C_{18}H_{15}FN_6$, 335; Found, 335.

Example 29

2-[1-[(3-chloro-2-fluorophenyl)methyl]imidazol-4-yl]-4-(1H-triazol-4-yl)pyridine

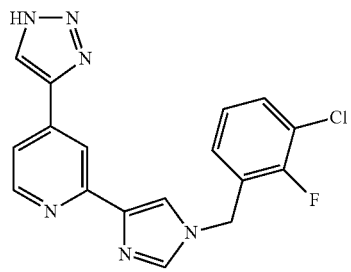 [SMILES: Fc1c(Cl)cccc1Cn1cnc(-c2cc(-c3c[nH]nn3)ccn2)c1]

The title compound was prepared in 5% yield starting from 2-(1H-imidazol-4-yl)pyridine-4-carbonitrile (Preparation 21A) according to the procedure of Example 2. $^1$H NMR (400 MHz, DMSO-d6): δ 5.41 (2H, s), 7.24-7.33 (2H, m), 7.59 (1H, m), 7.65 (1H, dd, J=5.1 and 1.7 Hz), 7.79 (1H, s), 7.91 (1H, s), 8.32 (1H, s), 8.52 (1H, d, J=5.1 Hz). [M+H] Calc'd for $C_{17}H_{12}ClFN_6$, 355; Found, 355.

Example 30

2-[1-[(2-fluoro-3-methoxyphenyl)methyl]imidazol-4-yl]-4-(1H-triazol-4-yl)pyridine

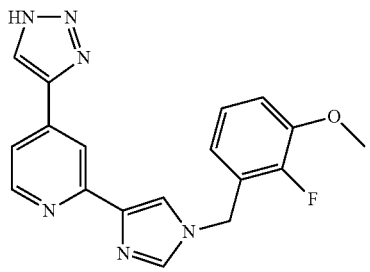 [SMILES: COc1cccc(Cn2cnc(-c3cc(-c4c[nH]nn4)ccn3)c2)c1F]

The title compound was prepared in 6% yield starting from 2-(1H-imidazol-4-yl)pyridine-4-carbonitrile (Preparation 21A) according to the procedure of Example 2. $^1$H NMR (400 MHz, DMSO-d6): δ 3.84 (3H, s), 5.34 (2H, s), 6.90 (1H, m), 7.15 (2H, 2s), 7.64 (1H, d, J=5.0 Hz), 7.74 (1H, s), 7.87 (1H, s), 8.32 (1H, s), 8.53 (1H, d, J=5.2 Hz), 8.63 (1H, br s). [M+H] Calc'd for $C_{18}H_{15}FN_6O$, 351; Found, 351.

Example 31

4-(1H-triazol-4-yl)-2-[1-[2-[2-(trifluoromethyl)phenyl]ethyl]imidazol-4-yl]pyridine

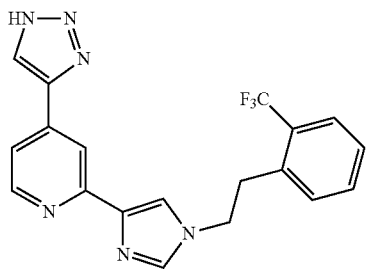

The title compound was prepared in 3% overall yield according to the procedure of Example 6 starting from 2-(1H-imidazol-4-yl)pyridine-4-carbonitrile (Preparation 21A). $^1$H NMR (400 MHz, DMSO-d6): δ 3.27 (2H, t, J=6.4 Hz), 4.32 (2H, t, J=7.8 Hz), 7.46 (2H, m), 7.60-7.81 (6H, m), 8.47-8.63 (2H, m). [M+H] Calc'd for $C_{19}H_{15}F_3N_6$, 385; Found, 385.

Example 32

2-[1-[2-(2-chlorophenyl)-2-methylpropyl]imidazol-4-yl]-4-(1H-triazol-4-yl)pyridine

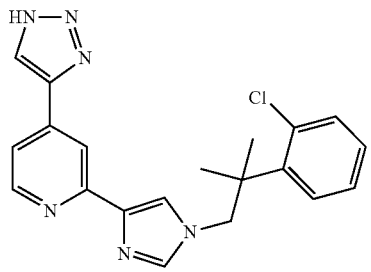 [SMILES: CC(C)(Cn1cnc(-c2cc(-c3c[nH]nn3)ccn2)c1)c1ccccc1Cl]

The title compound was prepared in 7% overall yield according to the procedure of Example 6 starting from 2-(1H-imidazol-4-yl)pyridine-4-carbonitrile (Preparation 21A). $^1$H NMR (400 MHz, DMSO-d6): δ 1.51 (6H, s), 4.61 (2H, s), 7.23-7.37 (5H, m), 7.53 (1H, d, J=7.5 Hz), 8.22 (1H, s), 8.42 (1H, s), 8.52 (1H, m). [M+H] Calc'd for $C_{20}H_{19}ClN_6$, 379; Found, 379.

Example 33

2-[1-(1-phenylpropan-2-yl)imidazol-4-yl]-4-(1H-triazol-4-yl)pyridine

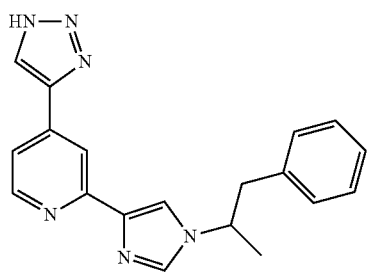 [SMILES: CC(Cc1ccccc1)n1cnc(-c2cc(-c3c[nH]nn3)ccn2)c1]

The title compound was prepared in 1% overall yield according to the procedure of Example 6 starting from 2-(1H-imidazol-4-yl)pyridine-4-carbonitrile (Preparation 21A). $^1$H NMR (400 MHz, DMSO-d6): δ 0.86 (3H, t, J=7.2 Hz), 2.33 (2H, m), 5.31 (1H, m), 7.33 (1H, d, J=7.3 Hz), 7.38 (1H, t, J=7.2 Hz), 7.46 (1H, s), 7.48 (1H, s), 7.73 (1H, dd, J=5.0 and 1.6 Hz), 7.93 (1H, s), 7.98 (1H, s), 8.47 (1H, s), 8.54 (1H, d), 8.60 (1H, s). [M+H] Calc'd for $C_{19}H_{18}N_6$, 331; Found, 331.

Example 34

4-(1H-triazol-4-yl)-2-[1-[2-[2-(trifluoromethoxy)phenyl]ethyl]imidazol-4-yl]pyridine

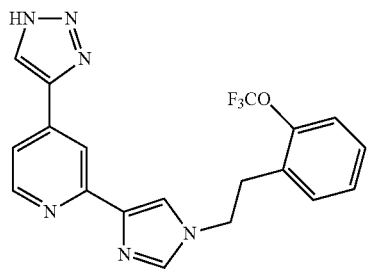

The title compound was prepared in 5% overall yield according to the procedure of Example 6 starting from 2-(1H-imidazol-4-yl)pyridine-4-carbonitrile (Preparation 21A). $^1$H NMR (400 MHz, DMSO-d6): δ 3.18 (2H, t, J=7.0 Hz), 4.32 (2H, t, J=7.2 Hz), 7.20 (1H, d, J=8.3 Hz), 7.27 (1H, s), 7.62 (1H, dd, J=5.1 and 1.6 Hz), 7.64 (1H, d, J=4.5 Hz), 7.83 (1H, d, J=4.5 Hz), 8.28 (1H, s), 8.56 (1H, d, J=5.2 Hz), 8.58 (1H, d, J=5.2 Hz). [M+H] Calc'd for $C_{19}H_{15}F_3N_6O$, 401; Found, 401.

Preparation 35A 4-ethynyl-2-[1-(2-naphthalen-1-ylethyl)imidazol-4-yl]pyridine

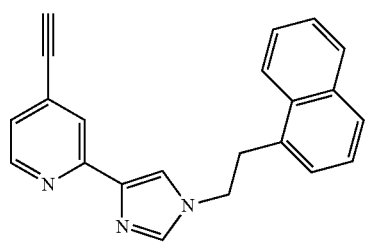 [SMILES: C#Cc1ccnc(-c2cn(CCc3cccc4ccccc34)cn2)c1]

A mixture of 2-[1-(2-naphthalen-1-ylethyl)imidazol-4-yl]pyridine-4-carbaldehyde (1.08 g, 3.32 mmol) and $K_2CO_3$ (0.92 g, 6.64 mmol) in MeOH (20 mL) was stirred for 15 min at rt, then (1-diazo-2-oxo-propyl)-phosphonic acid dimethyl ester (2.4 eq) was added and stirred for 2 hr at rt. LC/MS showed the reaction was completed, concentrated and purified by flash column chromatography on silica gel (DCM/MeOH=20/1) to afford the title compound (0.8 g, 75%). [M+H] Calc'd for $C_{22}H_{17}N_3$, 324; Found, 324.

Preparation 35B

4-[5-iodo-1-[(4-methoxyphenyl)methyl]triazol-4-yl]-2-[1-(2-naphthalen-1-ylethyl)imidazol-4-yl]pyridine

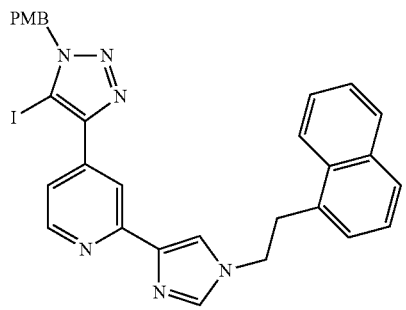

A mixture of 1-(azidomethyl)-4-methoxybenzene (310 mg, 1.86 mmol), KI (617 mg, 3.72 mmol) and $Cu(ClO_4)_2 \cdot 6H_2O$ (1.376 g, 3.72 mmol) in THF was stirred for 5 min at rt. Then TEA (375 mg, 3.72 mmol) and 4-ethynyl-2-[1-(2-naphthalen-1-ylethyl)imidazol-4-yl]pyridine (600 mg, 1.86 mmol) were added sequentially and stirred for 1 h at rt. LC/MS showed the reaction was completed, diluted with EtOAc, washed by 25% $NH_3 \cdot H_2O$, dried, concentrated to give the title compound (1.1 g, 97%). [M+H] Calc'd for $C_{30}H_{25}IN_6O$, 613; Found, 613.

Preparation 35C

4-[5-fluoro-1-[(4-methoxyphenyl)methyl]triazol-4-yl]-2-[1-(2-naphthalen-1-ylethyl)imidazol-4-yl]pyridine

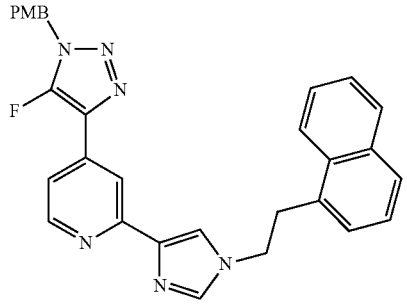

A mixture of 4-[5-iodo-1-[(4-methoxyphenyl)methyl]triazol-4-yl]-2-[1-(2-naphthalen-1-ylethyl)imidazol-4-yl]pyridine (100 mg, 0.25 mmol) and KF (77 mg, 1.23 mmol) in $ACN/H_2O$ (2 ml/2 ml) was stirred for 10 min at 160° C. in a microwave oven. LC/MS showed the reaction was completed, $H_2O$ was added, extracted with EtOAc, dried to give the title compound (100 mg, 80%) as a yellow solid. [M+H] Calc'd for $C_{30}H_{25}FN_6O$, 505; Found, 505.

Example 35

4-(5-fluoro-1H-triazol-4-yl)-2-[1-(2-naphthalen-1-ylethyl)imidazol-4-yl]pyridine

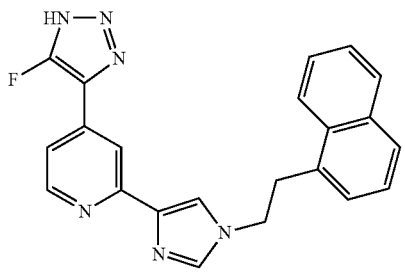 [SMILES: Fc1[nH]nnc1-c1ccnc(-c2cn(CCc3cccc4ccccc34)cn2)c1]

A solution of 4-[5-fluoro-1-[(4-methoxyphenyl)methyl]triazol-4-yl]-2-[1-(2-naphthalen-1-ylethyl)imidazol-4-yl]pyridine (100 mg) in TFA (3 mL) was stirred for 5 hr at 65° C. LC/MS showed the reaction was completed. The reaction mixture was concentrated and purified by prep-HPLC to give the title compound (23 mg, 30%). $^1$H NMR (400 MHz, CD$_3$OD): δ 3.75 (2H, m), 4.95 (2H, m), 7.30-7.58 (4H, m), 7.82-7.93 (3H, m), 8.10-8.25 (3H, m), 8.71 (1H, m), 8.73 (1H, m). [M+H] Calc'd for $C_{22}H_{17}FN_6$, 385; Found, 385.

Preparation 36A

4-[5-chloro-1-[(4-methoxyphenyl)methyl]triazol-4-yl]-2-[1-(2-naphthalen-1-ylethyl)imidazol-4-yl]pyridine

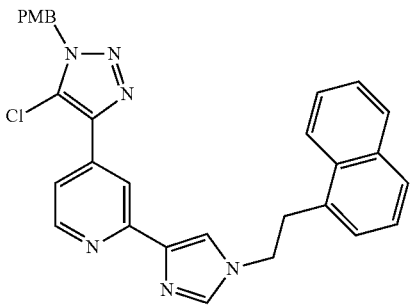

The title compound was prepared in 70% yield according to the procedure of Preparation 35C using KCl. [M+H] Calc'd for $C_{30}H_{25}ClN_6O$, 521; Found, 521.

Example 36

4-(5-chloro-1H-triazol-4-yl)-2-[1-(2-naphthalen-1-ylethyl)imidazol-4-yl]pyridine

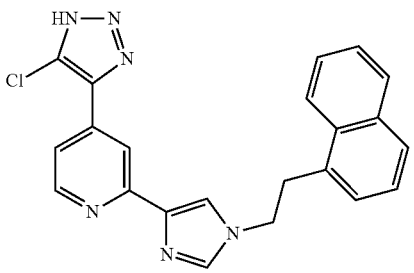 [SMILES: Clc1[nH]nnc1-c1ccnc(-c2cn(CCc3cccc4ccccc34)cn2)c1]

The title compound was prepared in 10% yield according to the general procedure for the preparation of Example 35. $^1$H NMR (400 MHz, CD$_3$OD): δ 3.62-3.64 (2H, m), 4.55-4.57 (2H, m), 7.15-7.44 (4H, m), 7.70-8.25 (6H, m), 8.45-8.47 (1H, m), 8.61-8.63 (1H, m). [M+H] Calc'd for $C_{22}H_{17}ClN_6$, 401; Found, 401.

Preparation 37A

4-[1-[(4-methoxyphenyl)methyl]-5-(trifluoromethyl)triazol-4-yl]-2-[1-(2-naphthalen-1-ylethyl)imidazol-4-yl]pyridine

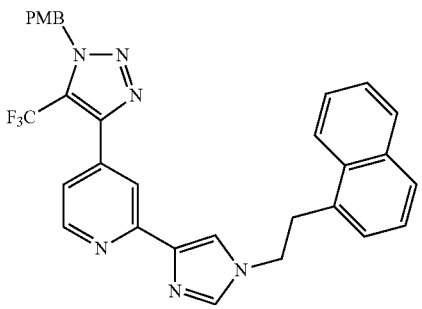

To a mixture of 4-[5-iodo-1-[(4-methoxyphenyl)methyl]triazol-4-yl]-2-[1-(2-naphthalen-1-ylethyl)imidazol-4-yl]pyridine (100 mg, 0.26 mmol), CuI (50 mg, 0.26 mmol), KF (45 mg, 0.78 mmol), Ag$_2$CO$_3$ (144 mg, 0.52 mmol) and 1,10-phenanthroline in DMF was added TMSCF$_3$ (111 mg, 0.78 mmol) at rt. The reaction mixture was stirred for 2 hr at 100° C. in a sealed tube. It was then filtered and separated between water and CH$_2$Cl$_2$, dried and concentrated to give the crude compound (97 mg, 70%). [M+H] Calc'd for $C_{31}H_{25}F_3N_6O$, 555; Found, 555.

Example 37

2-[1-(2-naphthalen-1-ylethyl)imidazol-4-yl]-4-[5-(trifluoromethyl)-1H-triazol-4-yl]pyridine

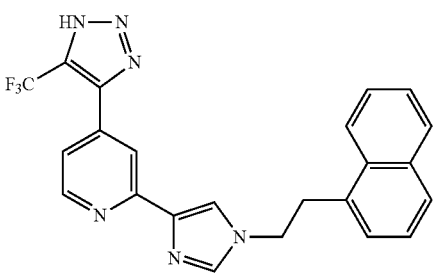 [SMILES: FC(F)(F)c1[nH]nnc1-c1ccnc(-c2cn(CCc3cccc4ccccc34)cn2)c1]

The title compound was prepared in 3% yield according to the general procedure for the preparation of Example 35. $^1$H NMR (400 MHz, CD$_3$OD): δ 3.65 (2H, t, J=6.8 Hz), 4.59 (2H, t, J=6.8 Hz), 7.18-7.48 (4H, m), 7.62-7.64 (1H, m), 7.72 (1H, d, J=8.0 Hz), 7.81 (1H, d, J=8.0 Hz), 7.89-8.02 (2H, m), 8.10 (1H, s), 8.58 (1H, s), 8.69 (1H, d, J=4.8 Hz). [M+H] Calc'd for $C_{23}H_{17}F_3N_6$, 435; Found, 435.

Example 38

4-(5-iodo-1H-triazol-4-yl)-2-[1-(2-naphthalen-1-ylethyl)imidazol-4-yl]pyridine

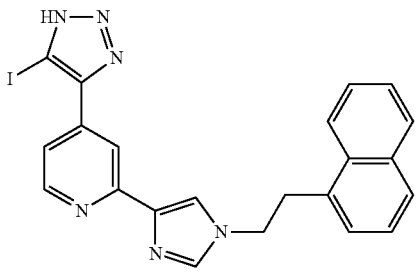 [SMILES: Ic1[nH]nnc1-c1ccnc(-c2cn(CCc3cccc4ccccc34)cn2)c1]

The title compound was prepared in 30% yield according to the general procedure for the preparation of Example 35 using 4-[5-iodo-1-[(4-methoxyphenyl)methyl]triazol-4-yl]-2-[1-(2-naphthalen-1-ylethyl)imidazol-4-yl]pyridine. $^1$H NMR (400 MHz, CD$_3$OD): δ 3.77 (2H, t, J=6.8 Hz), 4.68 (2H, t, J=6.8 Hz), 7.32-7.59 (4H, m), 7.84 (1H, d, J=8.0 Hz), 7.93 (1H, d, J=8.0 Hz), 8.11-8.16 (2H, m), 8.20 (1H, s), 8.42 (1H, s), 8.53 (1H, s), 8.75 (1H, d, J=4.2 Hz). [M+H] Calc'd for C$_{22}$H$_{17}$IN$_6$, 493; Found, 493.

Preparation 39A

2-[5-[2-(cyclopropylmethoxy)-4-fluorophenyl]-1-methylimidazol-4-yl]pyridine-4-carboxylic acid

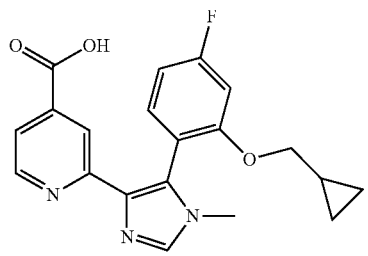 [SMILES: Cn1cnc(-c2cc(C(=O)O)ccn2)c1-c1ccc(F)cc1OCC1CC1]

A mixture of 2-[5-[2-(cyclopropylmethoxy)-4-fluorophenyl]-1-methylimidazol-4-yl]-4-(1H-triazol-4-yl)pyridine (348 mg, 1 mmol, Preparation 4A) and NaOH (1 mL, 5 mmol) in EtOH (10 mL) was refluxed overnight. LC/MS showed the reaction was completed, cooled to rt and acidified to pH=3-4 by 1N HCl, the solid was filtered and dried to give the title compound (256 mg, 70%). [M+H] Calc'd for C$_{20}$H$_{18}$FN$_3$O$_3$, 368; Found, 368.

Preparation 39B

[2-[5-[2-(cyclopropylmethoxy)-4-fluorophenyl]-1-methylimidazol-4-yl]pyridin-4-yl]methanol

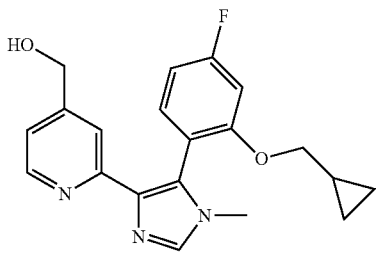 [SMILES: Cn1cnc(-c2cc(CO)ccn2)c1-c1ccc(F)cc1OCC1CC1]

To a solution of 2-[5-[2-(cyclopropylmethoxy)-4-fluorophenyl]-1-methylimidazol-4-yl]pyridine-4-carboxylic acid (256 mg, 0.7 mmol) in THF was added a solution of LiAlH$_4$ in THF (0.96 mL, 2.31 mmol, 2.4 M) at 0° C., then stirred for 2 hr at rt. LC/MS showed the reaction was completed, 0.1 mL H$_2$O, 0.1 mL NaOH, and 0.3 mL H$_2$O were added, filtered, concentrated and purified by flash column chromatography on silica gel (DCM/MeOH=20/1) to give the title compound (123 mg, 50%). [M+H] Calc'd for C$_{20}$H$_{20}$FN$_3$O$_2$, 354; Found, 354.

Preparation 39C

2-[5-[2-(cyclopropylmethoxy)-4-fluorophenyl]-1-methylimidazol-4-yl]pyridine-4-carbaldehyde

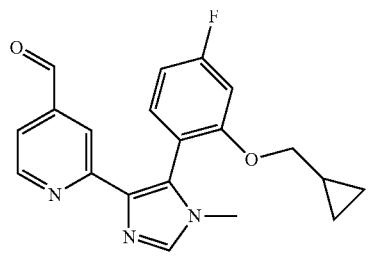 [SMILES: Cn1cnc(-c2cc(C=O)ccn2)c1-c1ccc(F)cc1OCC1CC1]

To a solution of Dess-Martin reagent (221 mg, 0.52 mmol) in THF (10 mL) was added a solution of [2-[5-[2-(cyclopropylmethoxy)-4-fluorophenyl]-1-methylimidazol-4-yl]pyridin-4-yl]methanol (123 mg, 0.35 mmol) at 0° C., then stirred for 2 hr at rt. LC/MS showed the reaction was completed. NaOH (14.7 mL, 14.7 mmol, 1M) was added to quench the reaction. The reaction mixture was extracted by EtOAc, dried and concentrated to give the crude compound (165 mg, 90%). [M+H] Calc'd for C$_{20}$H$_{18}$FN$_3$O$_2$, 352; Found, 352.

Preparation 39D 2-(benzenesulfonyl)-3-[2-[5-[2-(cyclopropylmethoxy)-4-fluorophenyl]-1-methylimidazol-4-yl]pyridin-4-yl]prop-2-enenitrile

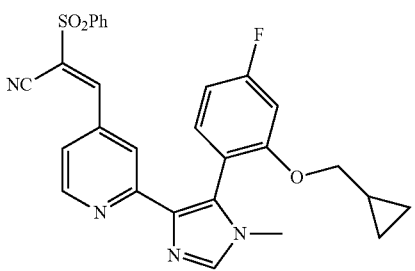

A mixture of 2-[5-[2-(cyclopropylmethoxy)-4-fluorophenyl]-1-methylimidazol-4-yl]pyridine-4-carbaldehyde (165 mg, 0.47 mmol), 2-(benzenesulfonyl)acetonitrile (85 mg, 0.47 mmol) and NaHCO$_3$ (2.35 mL, 0.58 mmol, 0.25 M) in EtOH (10 mL) was stirred overnight at rt. LC/MS showed the reaction was completed, concentrated and purified by

Example 39

4-[2-[5-[2-(cyclopropylmethoxy)-4-fluorophenyl]-1-methylimidazol-4-yl]pyridin-4-yl]-1H-triazole-5-carbonitrile

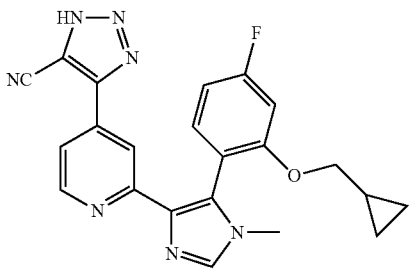 [SMILES: Cn1cnc(-c2cc(-c3nn[nH]c3C#N)ccn2)c1-c1ccc(F)cc1OCC1CC1]

A mixture of 2-(benzenesulfonyl)-3-[2-[5-[2-(cyclopropylmethoxy)-4-fluorophenyl]-1-methylimidazol-4-yl]pyridin-4-yl]prop-2-enenitrile (170 mg, 0.33 mmol) and NaN$_3$ (22 mg, 0.33 mmol) in DMF (10 mL) was stirred for 2 h at 100° C. LC/MS showed the reaction was completed, acidified to pH=3-4 by 1N HCl, and stirred for 30 min, then adjusted to pH=7-8 by 1N NaOH, concentrated and purified by HPLC to give the title compound (28 mg, 20%). $^1$H NMR (300 MHz, DMSO): δ 0.04-0.35 (4H, m), 0.92-0.93 (1H, m), 3.55 (3H, s), 3.74-3.92 (2H, m), 6.94-6.95 (1H, m), 7.15 (1H, d, J=10.2 Hz), 7.48 (1H, t, J=7.5 Hz), 7.80 (1H, d, J=5.4 Hz), 7.87 (1H, s), 8.73 (1H, d, J=5.4 Hz), 8.85 (1H, s). [M+H] Calc'd for C$_{22}$H$_{18}$FN$_7$O, 416; Found, 416.

Preparation 40A

2-[5-[2-(cyclopropylmethoxy)-4-fluorophenyl]-1-methylimidazol-4-yl]-4-ethynylpyridine

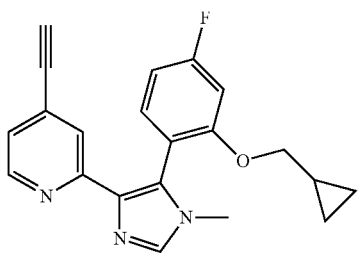 [SMILES: C#Cc1ccnc(-c2ncn(C)c2-c2ccc(F)cc2OCC2CC2)c1]

A mixture of 2-[5-[2-(cyclopropylmethoxy)-4-fluorophenyl]-1-methylimidazol-4-yl]pyridine-4-carbaldehyde (1.18 g, 3.32 mmol, Preparation 39C) and K$_2$CO$_3$ (0.92 g, 6.64 mmol) in MeOH (20 mL) was stirred for 15 min at rt, then (1-diazo-2-oxo-propyl)-phosphonic acid dimethyl ester (2.4 eq) was added and stirred for 2 hr at rt. LC/MS showed the reaction was completed, concentrated and purified by flash column chromatography on silica gel (DCM/MeOH=20/1) to afford the title compound (617 mg, 75%). [M+H] Calc'd for C$_{21}$H$_{18}$FN$_3$O, 348; Found, 348.

prep-TLC (DCM/MeOH=20/1) to give the title compound (170 mg, 70%). [M+H] Calc'd for C$_{28}$H$_{23}$FN$_4$O$_3$S, 515; Found, 515.

Preparation 40B

2-[5-[2-(cyclopropylmethoxy)-4-fluorophenyl]-1-methylimidazol-4-yl]-4-[5-iodo-1-[(4-methoxyphenyl)methyl]triazol-4-yl]pyridine

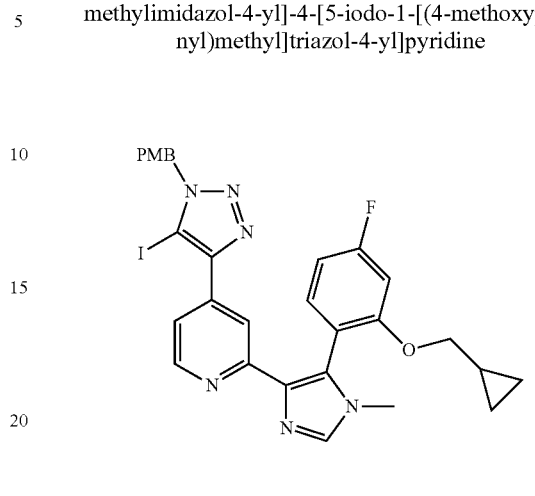

To a mixture of 1-(azidomethyl)-4-methoxybenzene (415 mg, 2.49 mmol), KI (826 mg, 4.98 mmol) and Cu(ClO$_4$)$_2$·6H$_2$O (1.842 g, 4.98 mmol) in THF which was stirred for 5 min at rt, added TEA (503 mg, 4.98 mmol) and 2-[5-[2-(cyclopropylmethoxy)-4-fluorophenyl]-1-methylimidazol-4-yl]-4-ethynylpyridine (617 mg, 2.49 mmol) sequentially. The reaction mixture was stirred for 1 h at rt. LC/MS showed the reaction was completed. It was diluted with EtOAc, washed by 25% NH$_3$·H$_2$O, dried, and concentrated to give the title compound (1.1 g, 70%). [M+H] Calc'd for C$_{29}$H$_{26}$FIN$_6$O$_2$, 637; Found, 637.

Preparation 40C

4-[5-chloro-1-[(4-methoxyphenyl)methyl]triazol-4-yl]-2-[5-[2-(cyclopropylmethoxy)-4-fluorophenyl]-1-methylimidazol-4-yl]pyridine

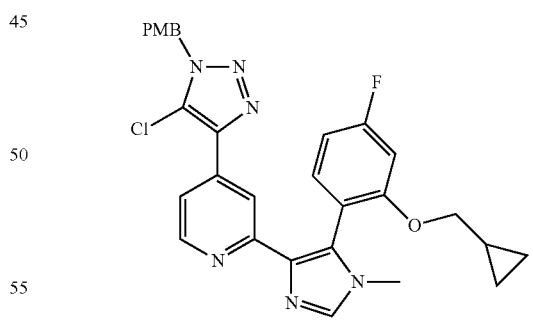

A mixture of 2-[5-[2-(cyclopropylmethoxy)-4-fluorophenyl]-1-methylimidazol-4-yl]-4-[5-iodo-1-[(4-methoxyphenyl)methyl]triazol-4-yl]pyridine (230 mg, 0.35 mmol) and KCl (130 mg, 1.75 mmol) in ACN/H$_2$O (2 ml/2 ml) was stirred for 10 min at 160° C. in a microwave oven. LC/MS showed the reaction was completed, H$_2$O was added, extracted with EtOAc, dried to give the title compound (128 mg, 67%) as a yellow solid. [M+H] Calc'd for C$_{29}$H$_{26}$ClFN$_6$O$_2$, 545; Found, 545.

Example 40

4-(5-chloro-1H-triazol-4-yl)-2-[5-[2-(cyclopropyl-methoxy)-4-fluorophenyl]-1-methylimidazol-4-yl]pyridine

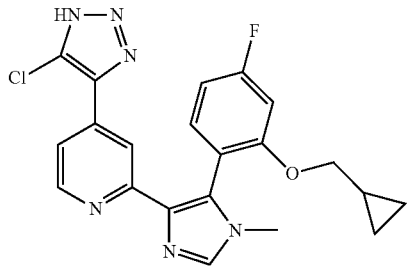

A solution of 4-[5-chloro-1-[(4-methoxyphenyl)methyl]triazol-4-yl]-2-[5-[2-(cyclopropylmethoxy)-4-fluorophenyl]-1-methylimidazol-4-yl]pyridine (128 mg, 0.235 mmol) in TFA (3 ml) was stirred for 5 h at 65° C. LC/MS showed the reaction was completed, concentrated, purified by HPLC to give the title compound (7 mg, 7%). $^1$H NMR (400 MHz, CD$_3$OD): δ 0.02-0.34 (4H, m), 0.94-0.97 (1H, m), 3.54 (3H, s), 3.77-3.87 (2H, m), 6.88-6.93 (1H, m), 7.06 (1H, d, J=12.8 Hz), 7.44 (1H, t, J=8.0 Hz), 7.78 (1H, s), 7.91 (1H, d, J=4.2 Hz), 8.69 (1H, d, J=4.2 Hz), 8.94 (1H, s). [M+H] Calc'd for C$_{21}$H$_{18}$ClFN$_6$O, 425; Found, 425.

Preparation 41A

2-[5-[2-(cyclopropylmethoxy)-4-fluorophenyl]-1-methylimidazol-4-yl]-4-[5-fluoro-1-[(4-methoxyphenyl)methyl]triazol-4-yl]pyridine

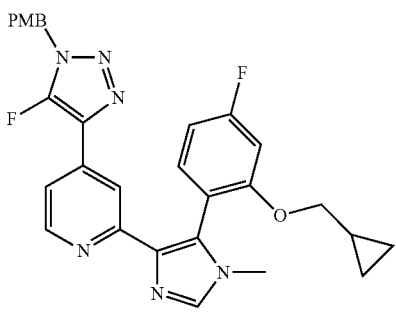

The title compound was prepared in 70% yield according to the procedure of Preparation 35C. [M+H] Calc'd for C$_{29}$H$_{26}$F$_2$N$_6$O$_2$, 529; Found, 529.

Example 41

2-[5-[2-(cyclopropylmethoxy)-4-fluorophenyl]-1-methylimidazol-4-yl]-4-(5-fluoro-1H-triazol-4-yl)pyridine

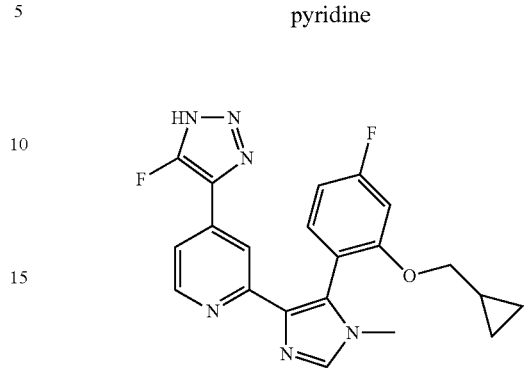

The title compound was prepared in 10% yield according to the general procedure for the preparation of Example 35. $^1$H NMR (400 MHz, CD$_3$OD): δ 0.04-0.28 (4H, m), 0.83-0.87 (1H, m), 3.43-3.80 (5H, m), 6.81-7.01 (2H, m), 7.34-7.68 (3H, m), 7.98-8.98 (2H, m). [M+H] Calc'd for C$_{21}$H$_{18}$F$_2$N$_6$O, 409; Found, 409.

Example 42

1-(cyclopropylmethyl)-4-{1H-[1,2,3]triazolo[4,5-c]pyridin-6-yl}-1H-imidazole

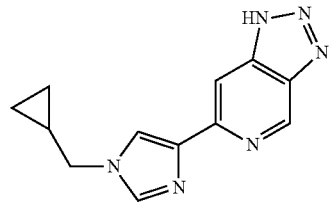 [SMILES: c1nc(-c2cn(CC3CC3)cn2)cc2[nH]nnc12]

To a solution of 6-chloro-3,4-pyridinediamine (12.5 g, 87 mmol) in HCl (Conc, 100 mL) was added NaNO$_2$ (6.6 g, 96 mmol) in water (20 mL) dropwise at 0° C. for 1 h. Upon completion, the pH was adjusted to 10 with Na$_2$CO$_3$ solution. The slurry was filtered, the solid was washed with PE and dried in vacuo to afford 6-chloro-1H-[1,2,3]triazolo[4,5-c]pyridine (10.0 g, 75%) as a yellow solid. [M+H] Calc'd for C$_5$H$_3$ClN$_4$, 155; Found, 155.

To a mixture of 6-chloro-1H-[1,2,3]triazolo[4,5-c]pyridine (4.62 g, 30 mmol), DIEA (7.8 g, 60 mmol), in DMF (50 mL) was added SEMCl (6.0 g, 36 mmol) at 0° C. and the reaction was stirred at ambient temperature for 16 hours. The mixture was concentrated in vacuo and purified by chromatography (ethyl acetate) to afford 6-chloro-1-{[2-(trimethylsilyl)ethoxy]methyl}-1H-[1,2,3]triazolo[4,5-c]pyridine (5.1 g, 61%) as a yellow solid. [M+H] Calc'd for C$_{11}$H$_{17}$ClN$_4$OSi, 285; Found, 285.

To a solution of compound 6-chloro-1-{[2-(trimethylsilyl)ethoxy]methyl}-1H-[1,2,3]triazolo[4,5-c]pyridine (6.2 g, 2.2 mmol) in MeOH (200 mL), was added DPPP (943 mg, 2.2 mmol), Et$_3$N (4.4 g, 44 mmol), and Pd(OAc)$_2$ (490 mg, 2.2 mmol) at room temperature. The mixture was heated at 100° C. for 48 h under 5 MPa carbon monoxide. The reaction was filtered, and the filtrate concentrated in vacuo.

The residue was purified by column chromatography (EA/PE=1/1) to afford methyl 1-{[2-(trimethylsilyl)ethoxy]methyl}-1H-[1,2,3]triazolo[4,5-c]pyridine-6-carboxylate (2.8 g, 41%) as a yellow solid. [M+H] Calc'd for $C_{13}H_{20}N_4O_3Si$, 309; Found, 309.

To a solution of methyl 1-{[2-(trimethylsilyl)ethoxy]methyl}-1H-[1,2,3]triazolo[4,5-c]pyridine-6-carboxylate (2.8 g, 9 mmol) in MeOH (30 mL) was added NaBH$_4$ (1.4 g, 36 mmol) at 0° C. The mixture was stirred at ambient temperature overnight. Upon completion, the reaction was concentrated in vacuo and purified by chromatograph (EA/PE=2/1) to afford (1-{[2-(trimethylsilyl)ethoxy]methyl}-1H-[1,2,3]triazolo[4,5-c]pyridin-6-yl)methanol (2.4 g, 95%) as a yellow oil. [M+H] Calc'd for $C_{12}H_{20}N_4O_2Si$, 281; Found, 281.

To a solution of (1-{[2-(trimethylsilyl)ethoxy]methyl}-1H-[1,2,3]triazolo[4,5-c]pyridin-6-yl)methanol (2.4 g, 8.6 mmol) in DCM (100 mL) was added MnO$_2$ (4.6 g, 36 mmol) at 0° C. The mixture was stirred at ambient temperature overnight. Upon completion, the reaction was concentrated in vacuo and the residue purified by column chromatography (EA/PE=1/1) to afford 1-{[2-(trimethylsilyl)ethoxy]methyl}-1H-[1,2,3]triazolo[4,5-c]pyridine-6-carbaldehyde (1.0 g, 40%) as a yellow oil. [M+H] Calc'd for $C_{12}H_{18}N_4O_2Si$, 279; Found, 279.

To a solution of 1-{[2-(trimethylsilyl)ethoxy]methyl}-1H-[1,2,3]triazolo[4,5-c]pyridine-6-carbaldehyde (0.9 g, 3.2 mmol) and TosMic (0.6 g, 3.2 mmol) in EtOH (50 mL) was added KCN (30 mg, 3.2 mmol) at ambient temperature. The reaction was allowed to stir for 20 min. Upon completion, the mixture was concentrated in vacuo and a solution of NH$_3$ in MeOH (1 g/20 mL) was added. The reaction was stirred for 16 h at 125° C. The reaction was concentrated in vacuo and the residue purified by column chromatography (EA=100) to give 4-(1-{[2-(trimethylsilyl)ethoxy]methyl}-1H-[1,2,3]triazolo[4,5-c]pyridin-6-yl)-1H-imidazole (350 mg, 34.5%). [M+H] Calc'd for $C_{14}H_{20}N_6OSi$, 317; Found, 317.

A mixture of 4-(1-{[2-(trimethylsilyl)ethoxy]methyl}-1H-[1,2,3]triazolo[4,5-c]pyridin-6-yl)-1H-imidazole (100 mg, 0.3 mmol), 1-(bromomethyl)cyclopropane (81 mg, 0.6 mmol) and K$_2$CO$_3$ (85 mg, 0.6 mmol) in DMF (10 mL) was allowed to stir overnight at 70° C. The reaction mixture was filtered and the filtrate concentrated in vacuo. The residue was purified by column chromatography (EA/PE=1/1) to give 1-(cyclopropylmethyl)-4-(1-{[2-(trimethylsilyl)ethoxy]methyl}-1H-[1,2,3]triazolo[4,5-c]pyridin-6-yl)-1H-imidazole as a yellow solid in good yield (80 mg, 72%): [M+H] Calc'd for $C_{18}H_{26}N_6OSi$, 371; Found, 371.

To a vial charged with 1-(cyclopropylmethyl)-4-(1-{[2-(trimethylsilyl)ethoxy]methyl}-1H-[1,2,3]triazolo[4,5-c]pyridin-6-yl)-1H-imidazole (60 mg, 0.16 mmol) in DCM (5 mL) was added TFA (1 mL) and allowed to stir at ambient temperature for 2 h. The reaction mixture was concentrated in vacuo and the residue purified by prep-HPLC to afford 1-(cyclopropylmethyl)-4-{1H-[1,2,3]triazolo[4,5-c]pyridin-6-yl}-1H-imidazole (17 mg, 44%): $^1$H NMR (400 MHz, CD$_3$OD): δ 0.59-0.61 (2H, m), 0.81-0.83 (2H, m), 1.47-1.49 (1H, m), 4.20 (2H, d, J=7.6 Hz), 8.36-8.39 (2H, m), 9.06 (1H, s), 9.49 (1H, s). LCMS (mobile phase: 5%-95% Acetonitrile-Water-0.02% NH$_4$Ac): purity is >95%, Rt=2.694 min. [M+H] Calc'd for $C_{12}H_{12}N_6$, 241; Found, 241.

Example 43

4-{1H-[1,2,3]triazolo[4,5-c]pyridin-6-yl}-1-(2,2,2-trifluoroethyl)-1H-imidazole

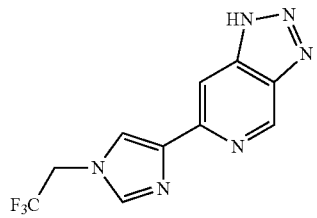 [SMILES: FC(F)(F)Cn1cnc(-c2cc3[nH]nnc3cn2)c1]

The title compound was prepared in 50% yield according to the procedure for example 42. $^1$H NMR (400 MHz, CD$_3$OD): δ 5.15-5.17 (2H, m), 8.20 (1H, s), 8.36 (1H, s), 8.51 (1H, s), 9.49 (1H, s). LCMS (mobile phase: 5%-95% Acetonitrile-Water-0.02% NH$_4$Ac): purity is >95%, Rt=2.639 min. [M+H] Calc'd for $C_{10}H_7F_3N_6$, 267; Found, 267.

Example 44

1-benzyl-4-{1H-[1,2,3]triazolo[4,5-c]pyridin-6-yl}-1H-imidazole

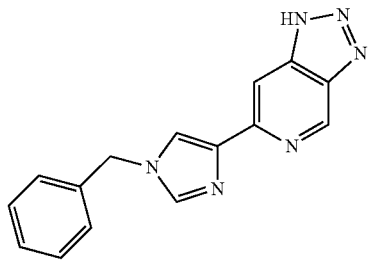 [SMILES: c1ccc(Cn2cnc(-c3cc4[nH]nnc4cn3)c2)cc1]

The title compound was prepared in 44% yield according to the procedure for example 42. $^1$H NMR (400 MHz, CD$_3$OD): δ 5.47 (2H, s), 7.43-7.49 (5H, m), 8.16 (1H, s), 8.28 (1H, s), 8.79 (1H, s), 9.43 (1H, s). LCMS (mobile phase: 5%-95% Acetonitrile-Water-0.02% NH$_4$Ac): purity is >95%, Rt=2.439 min. [M+H] Calc'd for $C_{15}H_{12}N_6$, 277; Found, 277.

Example 45

1-[(2-chlorophenyl)methyl]-4-{1H-[1,2,3]triazolo[4,5-c]pyridin-6-yl}-1H-imidazole

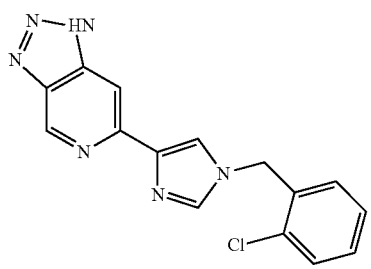 [SMILES: Clc1ccccc1Cn1cnc(-c2cc3[nH]nnc3cn2)c1]

The title compound was prepared in 43% yield according to the procedure for example 42. $^1$H NMR (400 MHz, DMSO-$d_6$): δ 5.46 (2H, s), 7.37-7.45 (3H, m), 7.51-7.56 (1H, m), 8.06 (1H, s), 8.26 (1H, s), 8.55 (1H, s), 9.44 (1H, s). LCMS (mobile phase: 5%-95% Acetonitrile-Water-0.02% NH$_4$Ac): purity is >95%, Rt=2.718 min. [M+H] Calc'd for C$_{15}$H$_{11}$ClN$_6$, 311; Found, 311.

Example 46

1-[(3-chlorophenyl)methyl]-4-{1H-[1,2,3]triazolo[4,5-c]pyridin-6-yl}-1H-imidazole

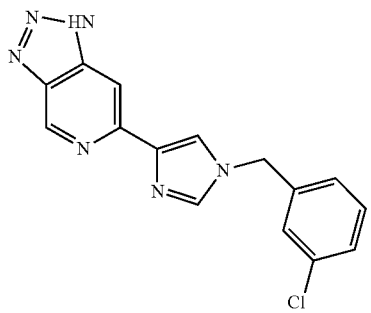 [SMILES: Clc1cccc(Cn2cnc(-c3cc4[nH]nnc4cn3)c2)c1]

The title compound was prepared in 52% yield according to the procedure for example 42. $^1$H NMR (400 MHz, DMSO-$d_6$): δ 5.49 (2H, s), 7.42-7.46 (3H, m), 7.54 (1H, s), 8.21 (1H, s), 8.30 (1H, s), 8.87 (1H, s), 9.44 (1H, s). LCMS (mobile phase: 5%-95% Acetonitrile-Water-0.02% NH$_4$Ac): purity is >95%, Rt=2.815 min. [M+H] Calc'd for C$_{15}$H$_{11}$ClN$_6$, 311; Found, 311.

Example 47

1-[(4-chlorophenyl)methyl]-4-{1H-[1,2,3]triazolo[4,5-c]pyridin-6-yl}-1H-imidazole

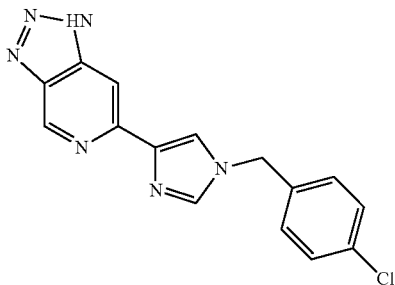 [SMILES: Clc1ccc(Cn2cnc(-c3cc4[nH]nnc4cn3)c2)cc1]

The title compound was prepared in 48% yield according to the procedure for example 42. $^1$H NMR (400 MHz, DMSO-$d_6$): δ 5.39 (2H, s), 7.46-7.51 (4H, m), 8.19 (1H, s), 8.27 (1H, s), 8.71 (1H, s), 9.47 (1H, s). LCMS (mobile phase: 5%-95% Acetonitrile-Water-0.02% NH$_4$Ac): purity is >95%, Rt=2.682 min. [M+H] Calc'd for C$_{15}$H$_{11}$ClN$_6$, 311; Found, 311.

Example 48

1-[(3,4-dichlorophenyl)methyl]-4-{1H-[1,2,3]triazolo[4,5-c]pyridin-6-yl}-1H-imidazole

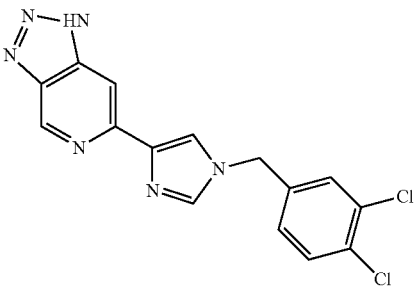 [SMILES: Clc1ccc(Cn2cnc(-c3cc4[nH]nnc4cn3)c2)cc1Cl]

The title compound was prepared in 48% yield according to the procedure for example 42. $^1$H NMR (400 MHz, DMSO-$d_6$): δ 5.53 (2H, s), 7.45 (1H, J=8.0 Hz, d), 7.65 (1H, J=8.0 Hz, d), 7.74 (1H, s), 8.31 (1H, s), 8.33 (1H, s), 9.11 (1H, s), 9.47 (1H, s). LCMS (mobile phase: 5%-95% Acetonitrile-Water-0.02% NH$_4$Ac): purity is >95%, Rt=2.682 min. [M+H] Calc'd for C$_{15}$H$_{10}$Cl$_2$N$_6$, 346; Found, 346.

Example 49

1-(4-chlorophenyl)-4-{1H-[1,2,3]triazolo[4,5-c]pyridin-6-yl}-1H-imidazole

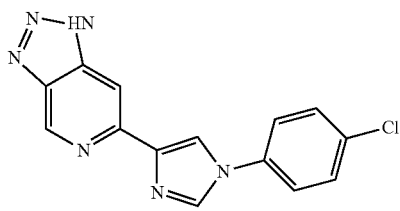 [SMILES: Clc1ccc(-n2cnc(-c3cc4[nH]nnc4cn3)c2)cc1]

A mixture of compound 4-(1-{[2-(trimethylsilyl)ethoxy]methyl}-1H-[1,2,3]triazolo[4,5-c]pyridin-6-yl)-1H-imidazole (100 mg, 0.3 mmol), 4-chlorophenylboronic acid (56 mg, 0.6 mmol), Cu(OAc)$_2$ (82 mg), pyridine (0.2 mL) in DCM (10 mL) was allow to stir overnight at ambient temperature. Upon completion, the reaction was filtered and concentrated in vacuo and the residue purified by column chromatography (EA/PE=1/1) to give crude 4-(1-{[2-(trimethylsilyl)ethoxy]methyl}-1H-[1,2,3]triazolo[4,5-c]pyridin-6-yl)-1H-imidazole. To a mixture of the crude intermediate in DCM (5 mL) was added TFA (1 mL) and stirred at room temperature for 2 hours. The mixture was concentrated in vacuo and purified by prep-HPLC to afford title compound (4 mg, 10%). $^1$H NMR (300 MHz, DMSO-$d_6$): δ 7.60-7.63 (2H, d, J=9.0 Hz), 7.84-7.87 (2H, d, J=9.0 Hz), 8.19 (1H, s), 8.38 (1H, s), 8.46 (1H, s), 9.43 (1H, s). LCMS (mobile phase: 5%-95% Acetonitrile-Water-0.02% NH$_4$Ac): purity is >95%, Rt=2.972 min. [M+H] Calc'd for C$_{14}$H$_9$ClN$_6$, 297; Found, 297.

Example 50

1-(2-chlorophenyl)-4-{1H-[1,2,3]triazolo[4,5-c]pyridin-6-yl}-1H-imidazole

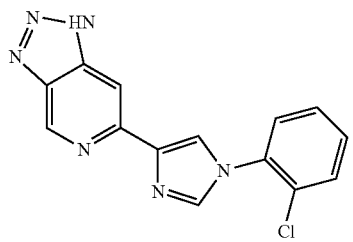 [SMILES: Clc1ccccc1-n1cnc(-c2cc3[nH]nnc3cn2)c1]

The title compound was prepared in 6% yield according to the procedure for example 49. $^1$H NMR (300 MHz, CD$_3$OD): δ 7.61-7.69 (2H, m), 7.74-7.79 (2H, m), 8.49 (1H, s), 8.53 (1H, s), 9.15 (1H, s), 9.58 (1H, s). LCMS (mobile phase: 5%-95% Acetonitrile-Water-0.02% NH$_4$Ac): purity is >95%, Rt=2.982 min. [M+H] Calc'd for C$_{14}$H$_9$ClN$_6$, 297; Found, 297.

Example 51

1-(3-chlorophenyl)-4-{1H-[1,2,3]triazolo[4,5-c]pyridin-6-yl}-1H-imidazole

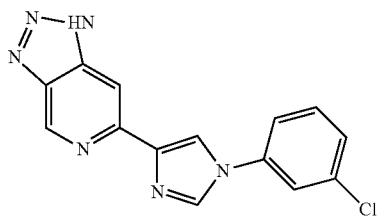 [SMILES: Clc1cccc(-n2cnc(-c3cc4[nH]nnc4cn3)c2)c1]

The title compound was prepared in 8% yield according to the procedure for example 49. $^1$H NMR (300 MHz, DMSO-d$_6$): δ 7.45-7.61 (2H, m), 7.79-7.84 (1H, m), 8.04 (1H, s), 8.20-8.23 (1H, m), 8.48-8.51 (1H, m), 8.59-861 (1H, m), 9.45-9.46 (1H, s).

LCMS (mobile phase: 5%-95%Acetonitrile-Water-0.02% NH4Ac): purity is >95%, Rt=3.105 min. [M+H] Calc'd for C$_{14}$H$_9$ClN$_6$, 297; Found, 297.

Example 52

1-(3,5-dichlorophenyl)-4-{1H-[1,2,3]triazolo[4,5-c]pyridin-6-yl}-1H-imidazole

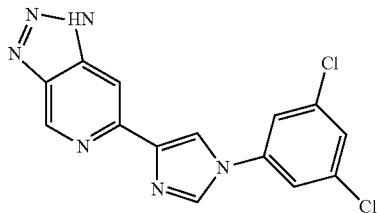 [SMILES: Clc1cc(Cl)cc(-n2cnc(-c3cc4[nH]nnc4cn3)c2)c1]

The title compound was prepared in 6% yield according to the procedure for example 49. $^1$H NMR (400 MHz, DMSO-d$_6$): δ 7.63 (1H, s), 8.05 (2H, s), 8.19 (1H, s), 8.52-8.59 (2H, m), 9.45 (1H, br). LCMS (mobile phase: 5%-95% Acetonitrile-Water-0.02% NH$_4$Ac): purity is >95%, Rt=2.682 min. [M+H] Calc'd for C$_{14}$H$_8$Cl$_2$N$_6$, 331; Found, 331.

Example 53

5-(4-fluorophenyl)-1-methyl-4-{1H-[1,2,3]triazolo[4,5-c]pyridin-6-yl}-1H-imidazole

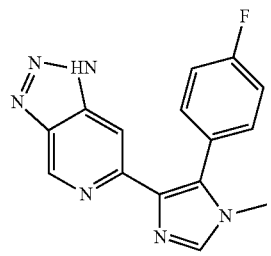 [SMILES: Cn1cnc(-c2cc3[nH]nnc3cn2)c1-c1ccc(F)cc1]

A mixture of 6-chloro-1-{[2-(trimethylsilyl)ethoxy]methyl}-1H-[1,2,3]triazolo[4,5-c]pyridine (1.4 g, 5.0 mmol), 1-methyl-4-(tributylstannyl)-1H-imidazole (2.5 g, 5.0 mmol), and Pd(PPh$_3$)$_4$ (530 mg, 0.5 mmol) in DMF (20 mL) was heated at 130° C. for 5 h. Upon completion, the reaction mixture was concentrated in vacuo and the residue purified by column chromatography (DCM/MeOH=10/1) to give 1-methyl-4-(1-{[2-(trimethylsilyl)ethoxy]methyl}-1H-[1,2,3]triazolo[4,5-c]pyridin-6-yl)-1H-imidazole (1.5 g, 90% yield).

A round-bottom flask charged with 1-methyl-4-(1-{[2-(trimethylsilyl)ethoxy]methyl}-1H-[1,2,3]triazolo[4,5-c]pyridin-6-yl)-1H-imidazole (660 mg, 2.0 mmol), and NBS (356 mg, 2.1 mmol) in DCM (10 mL) was allow to stir for 2 h at ambient temperature. Upon completion, water was added and the aqueous layer extracted by DCM. The combined organic layers were successively washed with brine, dried over Na$_2$SO$_4$ and concentrated in vacuo. The resulting crude 5-bromo-1-methyl-4-(1-{[2-(trimethylsilyl)ethoxy]methyl}-1H-[1,2,3]triazolo[4,5-c]pyridin-6-yl)-1H-imidazole (700 mg) was used in the next step without further purification.

A mixture of 5-bromo-1-methyl-4-(1-{[2-(trimethylsilyl)ethoxy]methyl}-1H-[1,2,3]triazolo[4,5-c]pyridin-6-yl)-1H-imidazole (0.5 mmol), 4-fluorophenylboronic acid (140 mg, 1.0 mmol), Pd(dppf)Cl$_2$ (37 mg, 0.05 mmol) and 2M Na$_2$CO$_3$ (1.0 mmol, 2.0 eq) in 5 mL dioxane was kept at 130° C. overnight. Upon completion, the reaction mixture was concentrated in vacuo and the residue was purified by column chromatography (DCM/MeOH=50/1) to afford the title compound (50 mg, 30%). $^1$H NMR (300 MHz, DMSO-d$_6$): δ 9.17 (1H, s), 7.90 (1H, s), 7.80 (1H, s), 7.44-7.48 (2H, m), 7.25 (t, J=8.7 Hz, 2H), 3.61 (3H, s). LCMS (mobile phase: 5%-95% Acetonitrile-Water-0.1% TFA) purity is >95%, Rt=2.427 min. [M+H] Calc'd for C$_{15}$H$_{11}$FN$_6$, 295; Found, 295.

Example 54

5-[2-(cyclopropylmethoxy)-4-fluorophenyl]-1-methyl-4-{1H-[1,2,3]triazolo[4,5-c]pyridin-6-yl}-1H-imidazole

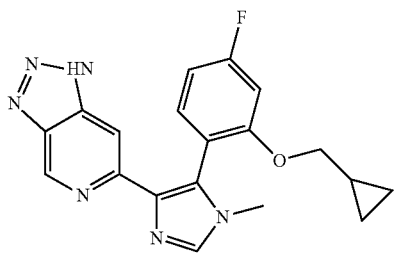 [SMILES: Cn1cnc(-c2cc3[nH]nnc3cn2)c1-c1ccc(F)cc1OCC1CC1]

The title compound was prepared in 28% yield according to the procedure for example 53. $^1$H NMR (300 MHz, CD$_3$OD): δ 9.47 (1H, s), 9.18 (1H, s), 7.52-7.57 (1H, m), 7.49 (1H, s), 7.14-7.18 (1H, m), 6.96-7.02 (1H, m), 3.89-3.94 (m, 2H), 3.82 (s, 3H), 1.02-1.07 (m, 1H), 0.06-0.43 (m, 4H). LCMS (mobile phase: 5%-95% Acetonitrile-Water-0.1% NH$_4$Ac): purity is >95%, Rt=2.855 min. [M+H] Calc'd for C$_{19}$H$_{17}$FN$_6$O, 365; Found, 365.

Preparation 55A 2-(5-bromo-1-(2-chlorobenzyl)-1H-imidazol-4-yl) isonicotinonitrile

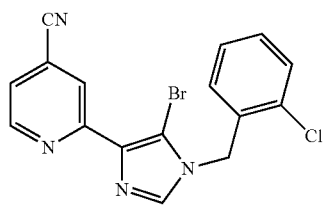 [SMILES: N#Cc1ccnc(-c2ncn(Cc3ccccc3Cl)c2Br)c1]

The title compound was prepared according to the procedure of Preparation 3A starting from 2-[1-[(2-chlorophenyl)methyl]imidazol-4-yl]pyridine-4-carbonitrile. [M+H] Calc'd for C$_{16}$H$_{10}$BrClN$_4$, 373; Found, 373.

Example 55

2-(5-bromo-1-(2-chlorobenzyl)-1H-imidazol-4-yl)-4-(2H-1,2,3-triazol-4-yl)pyridine

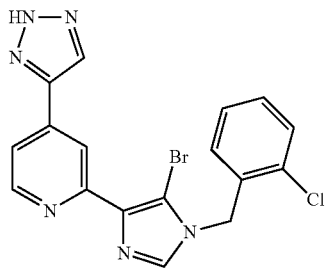

The title compound was prepared in 12% yield according to the procedure of Example 1. $^1$H NMR (400 MHz, DMSO-d$_6$): δ 5.43 (2H, s), 6.75 (1H, dd, J=7.0 and 2.0 Hz), 7.34-7.40 (2H, m), 7.55 (1H, dd, J=7.8 and 1.8 Hz), 7.73 (1H, dd, J=5.1 and 1.6 Hz), 8.16 (1H, s), 8.46 (1H, s), 8.63-8.68 (2H, m). [M+H] Calc'd for C$_{17}$H$_{12}$BrClN$_6$, 417; Found, 417.

Example 56

2-[1-[(2,3-Dichlorophenyl)methyl]imidazol-4-yl]-4-(5-trifluoromethyl-1H-triazol-4-yl)pyridine

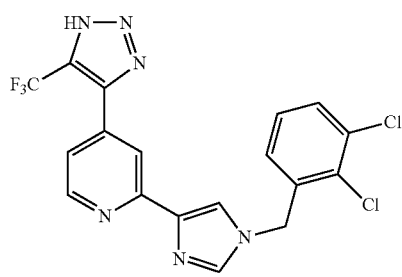

The title compound was prepared in 1% yield according to the procedure of Example 37. $^1$H NMR (400 MHz, CD$_3$OD): δ 5.60 (2H, s), 7.39-7.41 (2H, m), 7.61-7.68 (2H, m), 8.16-8.28 (2H, m), 8.72-8.77 (2H, m). [M+H] Calc'd for C$_{18}$H$_{11}$Cl$_2$F$_3$N$_6$, 439; Found, 439.

II. Biological Evaluation

Example 1

In Vitro Enzyme Inhibition Assay

This assay determines the ability of a test compound to inhibit FBXL11, FBXL10, and PHF8 demethylase activity. Baculovirus expressed FBXL11 (GenBank Accession #NM_012308, AA1-1162) was purchased from BPS Bioscience (Cat#50102). Baculovirus expressed FBXL10 (GenBank Accession #NM_032590, AA 1-650) was purchased from BPS Bioscience (Cat #50120). Baculovirus expressed PHF8 (GenBank Accession NP_055922.1) was purchased from Active Motif (Cat#31435).

FBXL11 Assay

The ability of test compounds to inhibit the activity of FBXL11 was determined in 384-well plate format under the following reaction conditions: 0.15 nM FBXL11, 30 nM H3K36me2-biotin labeled peptide (Anaspec cat #64442), 0.2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, 5 μM ammonium iron(II) sulfate. Reaction product is determined quantitatively by AlphaScreen detection after the addition of detection reagents anti-H3K36me1 antibody, AlphaScreen® Streptavidin-coated Donor beads, and AlphaScreen® Protein A Acceptor beads in 50 mM HEPES, pH7.3, 10 mM NaCl, 0.005% Brij35, 5 mM EDTA, 2 mg/ml BSA to final 10 μg/ml beads.

The assay reaction was initiated by the following: 3 μl of the mixture of 90 nM H3K36me2-biotin labeled peptide and 0.6 μM alpha-ketoglutaric acid with 3 μl of 11-point serial diluted inhibitor in 3% DMSO are added to each well of 384 well Proxiplate (Perkin Elmer), followed by the addition of 3 µl of 0.45 nM FBXL11 to initiate the reaction. The reaction mixture is incubated at room temperature for 1 hour, and terminated by the addition of 3 µl of appropriate dilution of anti H3K36me1 antibody in 50 mM HEPES, pH7.3, 10 mM NaCl, 0.005% Brij35, 5 mM EDTA, 2 mg/ml BSA. Plates will then incubated at room temperature for 40 minutes, followed by addition of 3 ul of 50 µg/ml AlphaScreen® Streptavidin-coated Donor beads and AlphaScreen® Protein A Acceptor beads in 50 mM HEPES, pH7.3, 10 mM NaCl, 0.005% Brij35, 5 mM EDTA, 2 mg/ml BSA. Plates will then be read by EnVision Multilabel Reader in AlphaScreen mode after minimum 2 hour incubation at room temperature. The AlphaScreen signal for each well is used to determine inhibition constant ($IC_{50}$).

FBXL10 Assay

The ability of test compounds to inhibit the activity of FBXL10 was determined in 384-well plate format under the following reaction conditions: 0.3 nM FBXL10, 30 nM H3K36me2-biotin labeled peptide (Anaspec cat #64442), 0.2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, 5 µM ammonium iron(II) sulfate. Reaction product is determined quantitatively by AlphaScreen detection after the addition of detection reagents anti-H3K36me1 antibody, AlphaScreen® Streptavidin-coated Donor beads, and AlphaScreen® Protein A Acceptor beads in 50 mM HEPES, pH7.3, 10 mM NaCl, 0.005% Brij35, 5 mM EDTA, 2 mg/ml BSA to final 10 µg/ml beads.

The assay reaction was initiated by the following: 3 µl of the mixture of 90 nM H3K36me2-biotin labeled peptide and 0.6 µM alpha-ketoglutaric acid with 3 µl of 11-point serial diluted inhibitor in 3% DMSO are added to each well of 384 well Proxiplate (Perkin Elmer), followed by the addition of 3 µl of 0.9 nM FBXL10 to initiate the reaction. The reaction mixture is incubated at room temperature for 1 hour, and terminated by the addition of 3 µl of appropriate dilution of anti H3K36me1 antibody in 50 mM HEPES, pH7.3, 10 mM NaCl, 0.005% Brij35, 5 mM EDTA, 2 mg/ml BSA. Plates will then incubated at room temperature for 40 minutes, followed by addition of 3 ul of 50 µg/ml AlphaScreen® Streptavidin-coated Donor beads and AlphaScreen® Protein A Acceptor beads in 50 mM HEPES, pH7.3, 10 mM NaCl, 0.005% Brij35, 5 mM EDTA, 2 mg/ml BSA. Plates will then be read by EnVision Multilabel Reader in AlphaScreen mode after minimum 2 hour incubation at room temperature. The AlphaScreen signal for each well is used to determine inhibition constant ($IC_{50}$).

PHF8 Assay

The ability of test compounds to inhibit the activity of PHF8 was determined in 384-well plate format under the following reaction conditions: 3 nM PHF8, 200 nM H3K9me1-biotin labeled peptide (Anaspec cat #64358), 0.5 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 5 µM ammonium iron(II) sulfate. Reaction product was determined quantitatively by TR-FRET after the addition of detection reagent Phycolink Streptavidin-allophycocyanin (Prozyme) and Europium-anti-unmodified-histone H3 lysine 9/lysine27 (H3K9/K27) antibody (PerkinElmer) in the presence of 5 mM EDTA in LANCE detection buffer (PerkinElmer) at a final concentration of 25 nM and 0.5 nM, respectively.

The assay reaction was initiated by the following: 2 µl of the mixture of 600 nM H3K9me1-biotin labeled peptide and 1.5 µM alpha-ketoglutaric acid with 2 µl of 11-point serial diluted inhibitor in 3% DMSO were added to each well of the plate, followed by the addition of 2 µl of 9 nM PHF8 to initiate the reaction. The reaction mixture was incubated at room temperature for 15 minutes, and terminated by the addition of 6 µl of 5 mM EDTA in LANCE detection buffer containing 50 nM Phycolink Streptavidin-allophycocyanin and 1 nM Europium-anti-unmodified H3K9/K27 antibody. Plates were read by EnVision Multilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

The ability of the compounds disclosed herein to inhibit demethylase activity was quantified and the respective $IC_{50}$ value was determined. Table 3 provides the $IC_{50}$ values of various compounds disclosed herein.

TABLE 3

| Chemical Synthesis Example | Name | FBXL10 $IC_{50}$ (µM) | FBXL11 $IC_{50}$ (µM) | PHF8 $IC_{50}$ (µM) |
|---|---|---|---|---|
| 1 | 2-(1-methylimidazol-4-yl)-4-(1H-triazol-4-yl)pyridine | B | | B |
| 2 | 2-[1-[(2-chlorophenyl)methyl]imidazol-4-yl]-4-(1H-triazol-4-yl)pyridine | A | B | B |
| 3 | 2-[5-(4-fluorophenyl)-1-methylimidazol-4-yl]-4-(1H-triazol-4-yl)pyridine | A | | B |
| 4 | 2-[5-[2-(cyclopropylmethoxy)-4-fluorophenyl]-1-methylimidazol-4-yl]-4-(1H-triazol-4-yl)pyridine | A | A | C |
| 5 | 2-[1-(1-phenylethyl)imidazol-4-yl]-4-(1H-triazol-4-yl)pyridine | A | A | B |
| 6 | 2-[1-[2-(2-chlorophenyl)ethyl]imidazol-4-yl]-4-(1H-triazol-4-yl)pyridine | A | A | A |
| 7 | 2-[1-[2-(2-methoxyphenyl)ethyl]imidazol-4-yl]-4-(1H-triazol-4-yl)pyridine | A | A | B |
| 8 | 2-[1-(1,2,3,4-tetrahydronaphthalen-1-ylmethyl)imidazol-4-yl]-4-(1H-triazol-4-yl)pyridine | A | A | B |
| 9 | 2-[1-[2-(2-ethoxyphenyl)ethyl]imidazol-4-yl]-4-(1H-triazol-4-yl)pyridine | A | A | B |
| 10 | 4-(1H-triazol-4-yl)-2-[1-[2-[2-(2,2,2-trifluoroethoxy)phenyl]ethyl]imidazol-4-yl]pyridine | A | | B |

TABLE 3-continued

| Chemical Synthesis Example | Name | FBXL10 IC$_{50}$ (μM) | FBXL11 IC$_{50}$ (μM) | PHF8 IC$_{50}$ (μM) |
|---|---|---|---|---|
| 11 | 2-[1-[2-[2-(cyclopropylmethoxy)phenyl]ethyl]imidazol-4-yl]-4-(1H-triazol-4-yl)pyridine | A | | B |
| 12 | 2-[1-(3,4-dihydro-2H-chromen-4-ylmethyl)imidazol-4-yl]-4-(1H-triazol-4-yl)pyridine | A | | A |
| 13 | 4-[2-[1-[(2-chlorophenyl)methyl]imidazol-4-yl]pyridin-4-yl]-1H-triazole-5-carbonitrile | A | | C |
| 14 | 4-[2-[1-[(2,3-dichlorophenyl)methyl]imidazol-4-yl]pyridin-4-yl]-1H-triazole-5-carbonitrile | A | | C |
| 15 | 4-[2-[1-(1,2,3,4-tetrahydronaphthalen-1-ylmethyl)imidazol-4-yl]pyridin-4-yl]-1H-triazole-5-carbonitrile | A | | B |
| 16 | 4-[2-[1-(2-naphthalen-1-ylethyl)imidazol-4-yl]pyridin-4-yl]-1H-triazole-5-carbonitrile | A | | B |
| 17 | 2-[1-[2-(2-phenylmethoxyphenyl)ethyl]imidazol-4-yl]-4-(1H-triazol-4-yl)pyridine | A | | C |
| 18 | 2-[1-[2-(2-phenoxyphenyl)ethyl]imidazol-4-yl]-4-(1H-triazol-4-yl)pyridine | A | | C |
| 19 | 2-[1-[(2,3-dichlorophenyl)methyl]imidazol-4-yl]-4-(5-iodo-1H-triazol-4-yl)pyridine | A | | B |
| 20 | 2-[1-[(2,3-dichlorophenyl)methyl]imidazol-4-yl]-4-(5-fluoro-1H-triazol-4-yl)pyridine | A | | B |
| 21 | 2-[1-[(2,3-dichlorophenyl)methyl]imidazol-4-yl]-4-(1H-triazol-4-yl)pyridine | A | A | B |
| 22 | 2-[1-[[2-chloro-3-(trifluoromethyl)phenyl]methyl]imidazol-4-yl]-4-(1H-triazol-4-yl)pyridine | A | A | B |
| 23 | 2-[1-(2-naphthalen-1-ylethyl)imidazol-4-yl]-4-(1H-triazol-4-yl)pyridine | A | A | B |
| 24 | 2-[5-(4-fluoro-3-methoxyphenyl)-1-methylimidazol-4-yl]-4-(1H-triazol-4-yl)pyridine | A | | B |
| 25 | 2-[5-(3-ethoxy-4-fluorophenyl)-1-methylimidazol-4-yl]-4-(1H-triazol-4-yl)pyridine | A | B | C |
| 26 | 2-[1-[[2-fluoro-3-(trifluoromethoxy)phenyl]methyl]imidazol-4-yl]-4-(1H-triazol-4-yl)pyridine | B | | C |
| 27 | 2-[1-[2-(2-phenylphenyl)ethyl]imidazol-4-yl]-4-(1H-triazol-4-yl)pyridine | B | | C |
| 28 | 2-[1-[(2-fluoro-3-methylphenyl)methyl]imidazol-4-yl]-4-(1H-triazol-4-yl)pyridin | A | | B |
| 29 | 2-[1-[(3-chloro-2-fluorophenyl)methyl]imidazol-4-yl]-4-(1H-triazol-4-yl)pyridine | A | | A |
| 30 | 2-[1-[(2-fluoro-3-methoxyphenyl)methyl]imidazol-4-yl]-4-(1H-triazol-4-yl)pyridine | A | | B |
| 31 | 4-(1H-triazol-4-yl)-2-[1-[2-[2-(trifluoromethyl)phenyl]ethyl]imidazol-4-yl]pyridine | A | | B |
| 32 | 2-[1-[2-(2-chlorophenyl)-2-methylpropyl]imidazol-4-yl]-4-(1H-triazol-4-yl)pyridine | A | | B |
| 33 | 2-[1-(1-phenylpropan-2-yl)imidazol-4-yl]-4-(1H-triazol-4-yl)pyridine | B | | C |
| 34 | 4-(1H-triazol-4-yl)-2-[1-[2-[2-(trifluoromethoxy)phenyl]ethyl]imidazol-4-yl]pyridine | A | | B |
| 35 | 4-(5-fluoro-1H-triazol-4-yl)-2-[1-(2-naphthalen-1-ylethyl)imidazol-4-yl]pyridine | A | | B |
| 36 | 4-(5-chloro-1H-triazol-4-yl)-2-[1-(2-naphthalen-1-ylethyl)imidazol-4-yl]pyridine | A | | C |

TABLE 3-continued

| Chemical Synthesis Example | Name | FBXL10 IC$_{50}$ (μM) | FBXL11 IC$_{50}$ (μM) | PHF8 IC$_{50}$ (μM) |
|---|---|---|---|---|
| 37 | 2-[1-(2-naphthalen-1-ylethyl)imidazol-4-yl]-4-[5-(trifluoromethyl)-1H-triazol-4-yl]pyridine | A | | D |
| 38 | 4-(5-iodo-1H-triazol-4-yl)-2-[1-(2-naphthalen-1-ylethyl)imidazol-4-yl]pyridine | A | | D |
| 39 | 4-[2-[5-[2-(cyclopropylmethoxy)-4-fluorophenyl]-1-methylimidazol-4-yl]pyridin-4-yl]-1H-triazole-5-carbonitrile | A | | C |
| 40 | 4-(5-chloro-1H-triazol-4-yl)-2-[5-[2-(cyclopropylmethoxy)-4-fluorophenyl]-1-methylimidazol-4-yl]pyridine | A | | D |
| 41 | 2-[5-[2-(cyclopropylmethoxy)-4-fluorophenyl]-1-methylimidazol-4-yl]-4-(5-fluoro-1H-triazol-4-yl)pyridine | A | | C |
| 42 | 1-(cyclopropylmethyl)-4-{1H-[1,2,3]triazolo[4,5-c]pyridin-6-yl}-1H-imidazole | A | | C |
| 43 | 4-{1H-[1,2,3]triazolo[4,5-c]pyridin-6-yl}-1-(2,2,2-trifluoroethyl)-1H-imidazole | B | | C |
| 44 | 1-benzyl-4-{1H-[1,2,3]triazolo[4,5-c]pyridin-6-yl}-1H-imidazole | A | A | B |
| 45 | 1-[(2-chlorophenyl)methyl]-4-{1H-[1,2,3]triazolo[4,5-c]pyridin-6-yl}-1H-imidazole | A | A | C |
| 46 | 1-[(3-chlorophenyl)methyl]-4-{1H-[1,2,3]triazolo[4,5-c]pyridin-6-yl}-1H-imidazole | A | A | C |
| 47 | 1-[(4-chlorophenyl)methyl]-4-{1H-[1,2,3]triazolo[4,5-c]pyridin-6-yl}-1H-imidazole | A | A | C |
| 48 | 1-[(3,4-dichlorophenyl)methyl]-4-{1H-[1,2,3]triazolo[4,5-c]pyridin-6-yl}-1H-imidazole | A | A | C |
| 49 | 1-(4-chlorophenyl)-4-{1H-[1,2,3]triazolo[4,5-c]pyridin-6-yl}-1H-imidazole | A | A | C |
| 50 | 1-(2-chlorophenyl)-4-{1H-[1,2,3]triazolo[4,5-c]pyridin-6-yl}-1H-imidazole | A | A | C |
| 51 | 1-(3-chlorophenyl)-4-{1H-[1,2,3]triazolo[4,5-c]pyridin-6-yl}-1H-imidazole | B | B | C |
| 52 | 1-(3,5-dichlorophenyl)-4-{1H-[1,2,3]triazolo[4,5-c]pyridin-6-yl}-1H-imidazole | B | | C |
| 53 | 5-(4-fluorophenyl)-1-methyl-4-{1H-[1,2,3]triazolo[4,5-c]pyridin-6-yl}-1H-imidazole | B | | C |
| 54 | 5-[2-(cyclopropylmethoxy)-4-fluorophenyl]-1-methyl-4-{1H-[1,2,3]triazolo[4,5-c]pyridin-6-yl}-1H-imidazole | B | | C |
| 55 | 2-(5-bromo-1-(2-chlorobenzyl)-1H-imidazol-4-yl)-4-(2H-1,2,3-triazol-4-yl)pyridine | A | | B |

Note:
Biochemical assay IC$_{50}$ data are designated within the following ranges:
A: ≤0.10 μM
B: >0.10 μM to ≤1.0 μM
C: >1.0 μM to ≤10 μM
D: >10 μM

Example 2

In Vitro Cell-Based Assay

Mia Paca-2 Pancreatic Cell Line Expression Assay for KDM2B-Related Genes

Gene expression assay to assess the ability of KDM2B small molecule inhibitors to activate the expression of KDM2B-bound genes of the established Mia Paca-2 cancer cell line.

Assay Background

The KDM2B protein has been shown to regulate the proliferation of AML, pancreatic and breast cancer. To demonstrate the specificity of small molecules for KDM2B's enzymatic activity, an assay to measure the relief of suppression caused by KDM2B in the established pancreatic cancer cell line model Mia Paca-2 was employed.

Assay Principle

This gene expression assay is a real-time PCR assay which quantifies the amount of messenger RNA from genes that are normally repressed by KDM2B interacting with EZH2 compared with a control GAPDH gene whose expression is not regulated by KDM2B. The amount of gene expression is correlated to the amount of small molecule inhibition of KDM2B's enzymatic activity.

Assay Method

The established cancer cell line Mia Paca-2 was purchased from American Type Culture Collection (ATCC) and routinely passaged according to ATCC published protocols. Cells were seeded at a density of 40,000 per 96-well. 24 hours after plating, cells received final concentrations of 20 nM, 40 nM, 80 nM and 320 nM of test compound. Time-matched control wells of 0.1% DMSO treatment were also included. Cells were incubated with test compound for 3, 6, 24 and 48 hrs at 37° C., 5% $CO_2$. At the end of each of the compound incubation period, media was removed and cells were trypsinized according to the ATCC published protocol. mRNA was then harvested from the cell samples using a RNeasy kit (Qiagen). mRNA was quantified and qualified using a Nanodrop machine (Thermo Scientific). mRNA was converted to cDNA using the High-Capacity cDNA Reverse Transcription Kit (Applied Biosystems). Equal amounts of cDNA were subjected to real-time PCR using Taqman Universal Master Mix (Thermo Scientific). The following Taqman gene expression assays were used for detection on a Viaa7 Real-time PCR system: Hs00224960_m1, Hs00164982_m1, Hs00907496_m1 and Hs02758991_g1 (Thermo Scientific). Data was analyzed using the delta-delta Ct method to calculate fold enrichment over DMSO sample gene expression.

Table 4 provides the cellular $IC_{50}$ values of various substituted heterocyclic compounds disclosed herein.

TABLE 4

| Chemical Synthesis Example | Name | Cellular $IC_{50}$ (µM) |
|---|---|---|
| 37 | 2-[1-(2-naphthalen-1-ylethyl)imidazol-4-yl]-4-[5-(trifluoromethyl)-1H-triazol-4-yl]pyridine | B |
| 41 | 2-[5-[2-(cyclopropylmethoxy)-4-fluorophenyl]-1-methylimidazol-4-yl]-4-(5-fluoro-1H-triazol-4-yl)pyridine | C |

Note:
Cellular assay $IC_{50}$ data are designated within the following ranges:
A: ≤0.10 µM
B: >0.10 µM to ≤1.0 µM
C: >1.0 µM to ≤10 µM
D: >10 µM III. Preparation of Pharmaceutical Dosage Forms Example 1

Oral Tablet

A tablet is prepared by mixing 48% by weight of a compound of Formula (I) or (III), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A method for inhibiting a histone demethylase enzyme comprising contacting a histone demethylase enzyme with a compound of Formula (Ic),

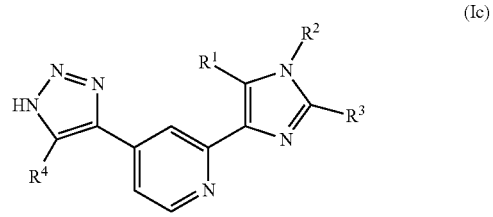

(Ic)

wherein the compound of Formula (Ic) includes pharmaceutically acceptable salts thereof, wherein:

$R^1$ is hydrogen, halogen, or substituted phenyl, wherein a substituent is at least one halogen, haloalkyl, $C_1$-$C_5$ alkyl, $C_1$-$C_5$ alkoxy, alkylaminoalkoxy, or alkoxyalkoxy;

$R^2$ is hydrogen, $C_1$-$C_5$ alkyl, mono- or bi-cyclic $C_7$-$C_{12}$ carbocyclylalkyl, or substituted arylalkyl, wherein a substituent is at least one halogen, haloalkyl, haloalkoxy, haloaryl, alkoxy, aryl, or aryloxy;

$R^3$ is hydrogen;

$R^4$ is hydrogen, halogen, —CN, or $C_1$-$C_4$ alkyl, wherein when $R^4$ is $C_1$-$C_4$ alkyl, said $C_1$-$C_4$ alkyl is optionally substituted with at least one halogen.

2. The method of claim 1, wherein $R^2$ is mono- or bi-cyclic $C_7$-$C_{12}$ carbocyclylalkyl.

3. The method of claim 1, wherein $R^2$ is optionally substituted naphthylalkyl or dihydroindylalkyl.

4. The method of claim 3, wherein the naphthylalkyl is naphthylmethyl, naphthylethyl, tetrahydronaphthylmethyl, tetrahydronaphthylethyl, chloronaphthylmethyl, fluoronaphthylmethyl, chloronaphthylethyl, fluoronaphthylethyl, propylnaphthylmethyl, or propylnaphthylethyl.

5. The method of claim 3, wherein the dihydroindyl of the dihydroindylalkyl is substituted with halogen or $C_1$-$C_4$ alkyl.

6. The method of claim 1, wherein $R^2$ is substituted arylalkyl, wherein a substituent is at least one halogen, haloalkyl, $C_1$-$C_5$ alkyl, $C_1$-$C_5$ alkoxy, alkylaminoalkoxy, or alkoxyalkoxy.

7. The method of claim 6, wherein the halogen is chloro or fluoro.

8. The method of claim 6, wherein the substituted arylalkyl is substituted phenylalkyl.

9. The method of claim 8, wherein the substituted phenylalkyl is chlorophenylmethyl, chlorophenylethyl, chlorophenylmethylpropyl, dichlorophenylmethyl, dichlorophenylethyl, chloro-fluorophenylmethyl, (fluoro)methylphenylmethyl, trifluoromethylphenylethyl, (trifluoromethyl)chlorophenylmethyl, (trifluoromethyl)fluorophenylmethyl, fluoro(methoxy)phenylmethyl, trifluoromethoxyphenylethyl, phenylphenylethyl, phenylmethylpropyl, methoxyphenylethyl, ethoxyphenylethyl, cylcopropylmethoxyphenylethyl, phenylmethoxyphenylethyl, or phenyloxyphenylethyl.

10. The method of claim 1, wherein $R^1$ is hydrogen.

11. The method of claim 1, wherein $R^4$ is hydrogen.

12. The method of claim 1, wherein $R^4$ is $C_1$-$C_4$ alkyl, and the alkyl is substituted with at least one halogen.

13. The method of claim 12, wherein the halogen is fluoro, and $R^4$ is $CH_2F$, $CHF_2$, or $CF_3$.

14. The method of claim 13, wherein $R^4$ is $CF_3$.

15. A method of treating pancreatic cancer in a subject comprising administering a therapeutically effective dose of a compound of Formula (Ic)

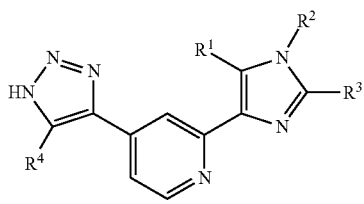

(Ic)

wherein the compound of Formula (Ic) includes pharmaceutically acceptable salts thereof, wherein
- $R^1$ is hydrogen, halogen, or substituted phenyl, wherein a substituent is at least one halogen, haloalkyl, $C_1$-$C_5$ alkyl, $C_1$-$C_5$ alkoxy, alkylaminoalkoxy, or alkoxyalkoxy;
- $R^2$ is hydrogen, $C_1$-$C_5$ alkyl, mono- or bi-cyclic $C_7$-$C_{12}$ carbocyclylalkyl, or substituted arylalkyl, wherein a substituent is at least one halogen, haloalkyl, haloalkoxy, haloaryl, alkoxy, aryl, or aryloxy;
- $R^3$ is hydrogen;
- $R^4$ is hydrogen, halogen, —CN, or $C_1$-$C_4$ alkyl, wherein when $R^4$ is $C_1$-$C_4$ alkyl, said $C_1$-$C_4$ alkyl is optionally substituted with at least one halogen.

16. The method of claim 15, wherein $R^2$ is mono- or bi-cyclic $C_7$-$C_{12}$ carbocyclylalkyl.

17. The method of claim 15, wherein $R^2$ is optionally substituted naphthylalkyl or dihydroindylalkyl.

18. The method of claim 17, wherein the naphthylalkyl is naphthylmethyl, naphthylethyl, tetrahydronaphthylmethyl, tetrahydronaphthylethyl, chloronaphthylmethyl, fluoronaphthylmethyl, chloronaphthylethyl, fluoronaphthylethyl, propylnaphthylmethyl, or propylnaphthylethyl.

19. The method of claim 17, wherein the dihydroindyl of the dihydroindylalkyl is substituted with halogen or $C_1$-$C_4$ alkyl.

20. The method of claim 15, wherein $R^2$ is substituted arylalkyl, wherein a substituent is at least one halogen, haloalkyl, $C_1$-$C_5$ alkyl, $C_1$-$C_5$ alkoxy, alkylaminoalkoxy, or alkoxyalkoxy.

21. The method of claim 20, wherein the halogen is chloro or fluoro.

22. The method of claim 20, wherein the substituted arylalkyl is substituted phenylalkyl.

23. The method of claim 22, wherein the substituted phenylalkyl is chlorophenylmethyl, chlorophenylethyl, chlorophenylmethylpropyl, dichlorophenylmethyl, dichlorophenylethyl, chloro-fluorophenylmethyl, (fluoro)methylphenylmethyl, trifluoromethylphenylethyl, (trifluoromethyl)chlorophenylmethyl, (trifluoromethyl)fluorophenylmethyl, fluoro(methoxy)phenylmethyl, trifluoromethoxyphenylethyl, phenylphenylethyl, phenylmethylpropyl, methoxyphenylethyl, ethoxyphenylethyl, cylcopropylmethoxyphenylethyl, phenylmethoxyphenylethyl, or phenyloxyphenylethyl.

24. The method of claim 15, wherein $R^1$ is hydrogen.

25. The method of claim 15, wherein $R^4$ is hydrogen.

26. The method of claim 15, wherein $R^4$ is $C_1$-$C_4$ alkyl, and the alkyl is substituted with at least one halogen.

27. The method of claim 26, wherein the halogen is fluoro, and $R^4$ is $CH_2F$, $CHF_2$, or $CF_3$.

28. The method of claim 27, wherein $R^4$ is $CF_3$.

* * * * *